(12) United States Patent
Mench et al.

(10) Patent No.: US 10,722,680 B1
(45) Date of Patent: Jul. 28, 2020

(54) APPARATUSES, SYSTEMS, AND METHODS FOR DETECTION OF TAMPERING

(71) Applicant: University of Tennessee Research Foundation, Knoxville, TN (US)

(72) Inventors: Matthew M. Mench, Knoxville, TN (US); Matthew A. Young, Rockford, TN (US); Chad Duty, Loudon, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 16/596,479

(22) Filed: Oct. 8, 2019

Related U.S. Application Data

(63) Continuation of application No. 16/456,337, filed on Jun. 28, 2019, which is a continuation-in-part of application No. 15/492,704, filed on Apr. 20, 2017.

(60) Provisional application No. 62/384,887, filed on Sep. 8, 2016, provisional application No. 62/325,305, filed on Apr. 20, 2016.

(51) Int. Cl.
| | |
|---|---|
| *A61M 25/00* | (2006.01) |
| *B65D 55/02* | (2006.01) |
| *E05B 73/00* | (2006.01) |
| *A61M 5/00* | (2006.01) |
| *A61M 39/02* | (2006.01) |
| *A61M 5/50* | (2006.01) |
| *B65D 75/32* | (2006.01) |

(52) U.S. Cl.
CPC ......... *A61M 25/002* (2013.01); *B65D 55/024* (2013.01); *A61M 5/002* (2013.01); *A61M 5/5086* (2013.01); *A61M 39/02* (2013.01); *B65D 75/322* (2013.01); *E05B 73/0023* (2013.01); *Y10T 70/5004* (2015.04); *Y10T 70/5031* (2015.04)

(58) Field of Classification Search
CPC .... A61M 25/002; A61M 5/002; A61M 39/02; A61M 5/5086; B65D 55/024; B65D 75/322; Y10T 70/5031; Y10T 70/5004; E05B 73/0023
See application file for complete search history.

(56) References Cited

U.S. PATENT DOCUMENTS

| | | | | |
|---|---|---|---|---|
| 4,782,977 A | * | 11/1988 | Watanabe ............ | B65D 55/024 220/324 |
| 5,893,475 A | * | 4/1999 | May ...................... | B65D 55/06 215/252 |
| 6,065,408 A | * | 5/2000 | Tillim ..................... | E05G 1/005 109/25 |

(Continued)

OTHER PUBLICATIONS

Notice of allowance corresponding to U.S. Appl. No. 15/492,704 dated Feb. 5, 2020.

(Continued)

*Primary Examiner* — Nimeshkumar D Patel
*Assistant Examiner* — Tania Courson
(74) *Attorney, Agent, or Firm* — Jenkins, Wilson, Taylor & Hunt, P.A.

(57) ABSTRACT

Methods, apparatuses and systems for detecting tampering are disclosed. The methods, apparatuses and systems for detecting tampering can involve positioning at least a portion of one or more ingress/egress line having a first end and a second end in a clamping box configured to provide detection of tampering; and detecting tampering by observing the clamping box.

26 Claims, 36 Drawing Sheets

(56) References Cited

U.S. PATENT DOCUMENTS

| | | | |
|---|---|---|---|
| 6,328,355 B1* | 12/2001 | Bortz | G09F 3/0323 |
| | | | 292/307 R |
| 6,553,930 B1 | 4/2003 | Johnston | |
| 6,926,165 B2* | 8/2005 | Conti | B65D 25/2888 |
| | | | 215/216 |
| 7,451,627 B2* | 11/2008 | Horngren | E05B 73/0023 |
| | | | 206/1.5 |
| 7,963,131 B2* | 6/2011 | Zhang | E05B 73/0023 |
| | | | 206/1.5 |
| 8,408,929 B2 | 4/2013 | Solon | |
| 8,556,859 B2 | 10/2013 | Nilson | |
| 9,907,907 B1 | 3/2018 | Salazar | |
| 9,944,436 B2* | 4/2018 | Kalmanides | B65D 43/0237 |
| 10,532,869 B2 | 1/2020 | Lorio | |
| 2008/0035035 A1* | 2/2008 | Stone | E05G 1/00 |
| | | | 109/1 R |
| 2008/0171981 A1 | 7/2008 | Khan | |
| 2010/0255704 A1* | 10/2010 | Gardner | G01G 23/017 |
| | | | 439/301 |
| 2011/0215683 A1* | 9/2011 | Nakasuji | E05B 73/0023 |
| | | | 312/107 |
| 2014/0100533 A1 | 4/2014 | Lyons | |
| 2014/0303595 A1 | 10/2014 | Justus et al. | |
| 2015/0060455 A1* | 3/2015 | Chou | B65D 77/2016 |
| | | | 220/270 |
| 2017/0049954 A1 | 2/2017 | Edwards | |
| 2017/0165437 A1 | 6/2017 | Lopansri | |
| 2019/0127134 A1 | 5/2019 | Lorio | |
| 2019/0275263 A1* | 9/2019 | Lopansri | A61M 5/5086 |

OTHER PUBLICATIONS

Interview Summary corresponding to U.S. Appl. No. 15/492,704 dated Oct. 29, 2019.

Office Action (Restriction Requirement) corresponding to U.S. Appl. No. 15/492,704 dated Sep. 12, 2019.

* cited by examiner

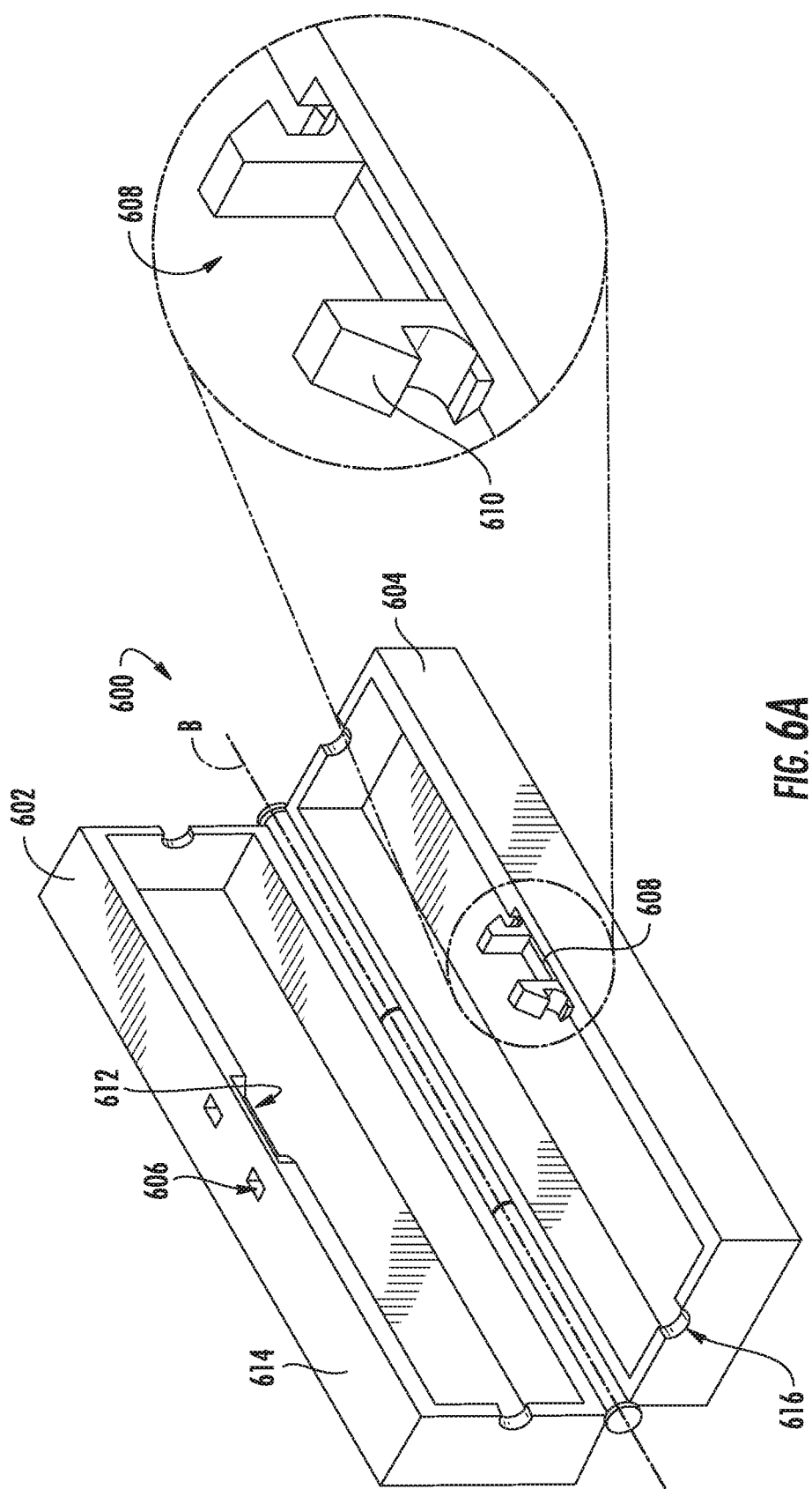

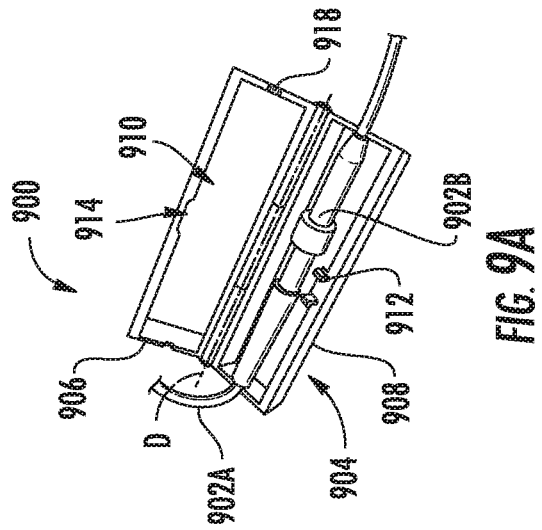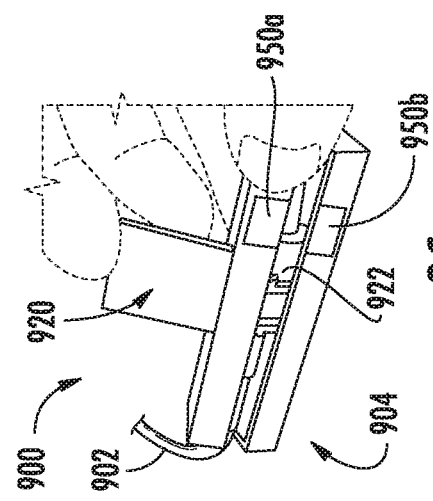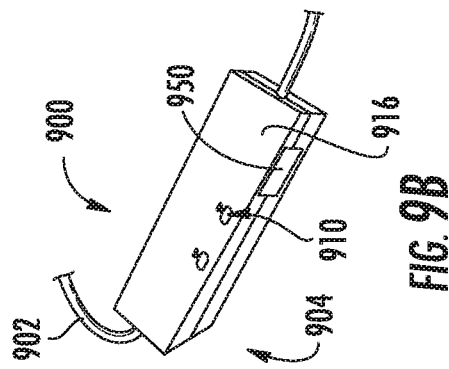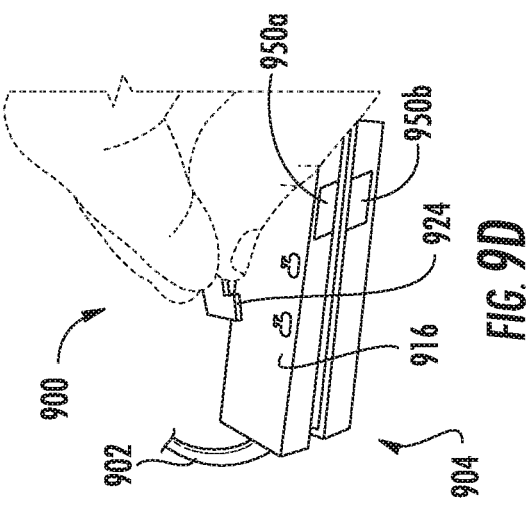
FIG. 9A
FIG. 9B
FIG. 9C
FIG. 9D

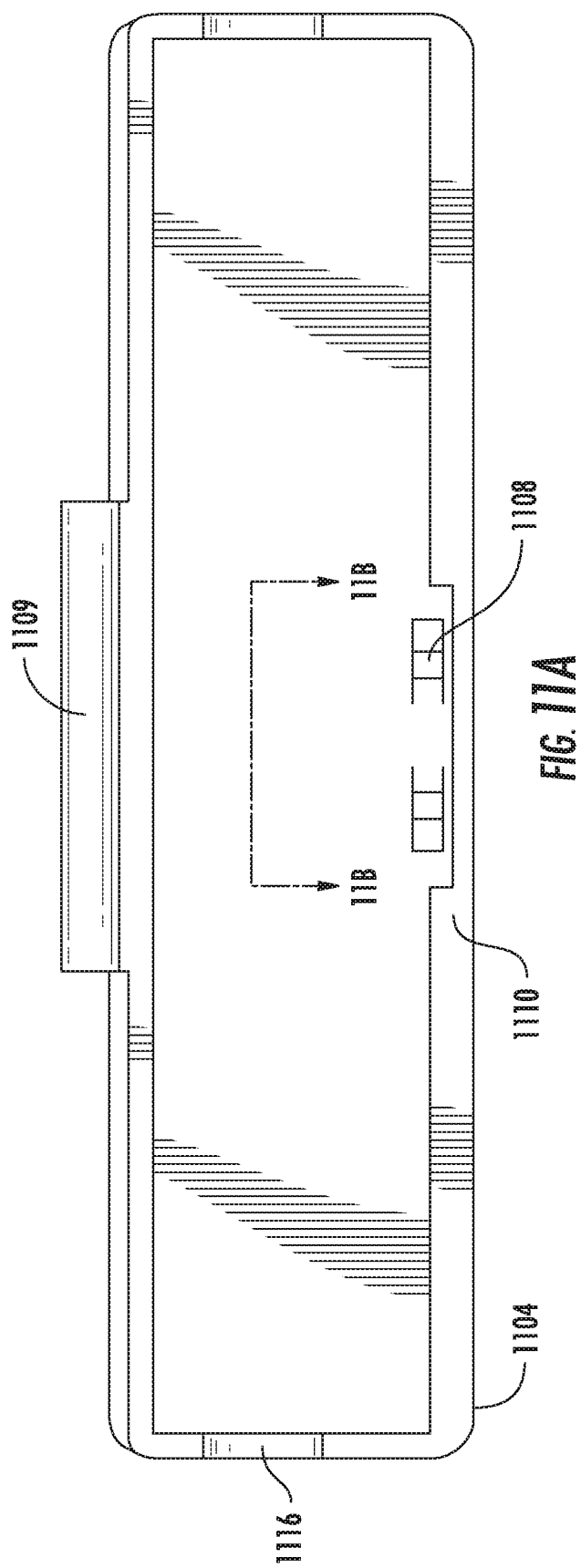

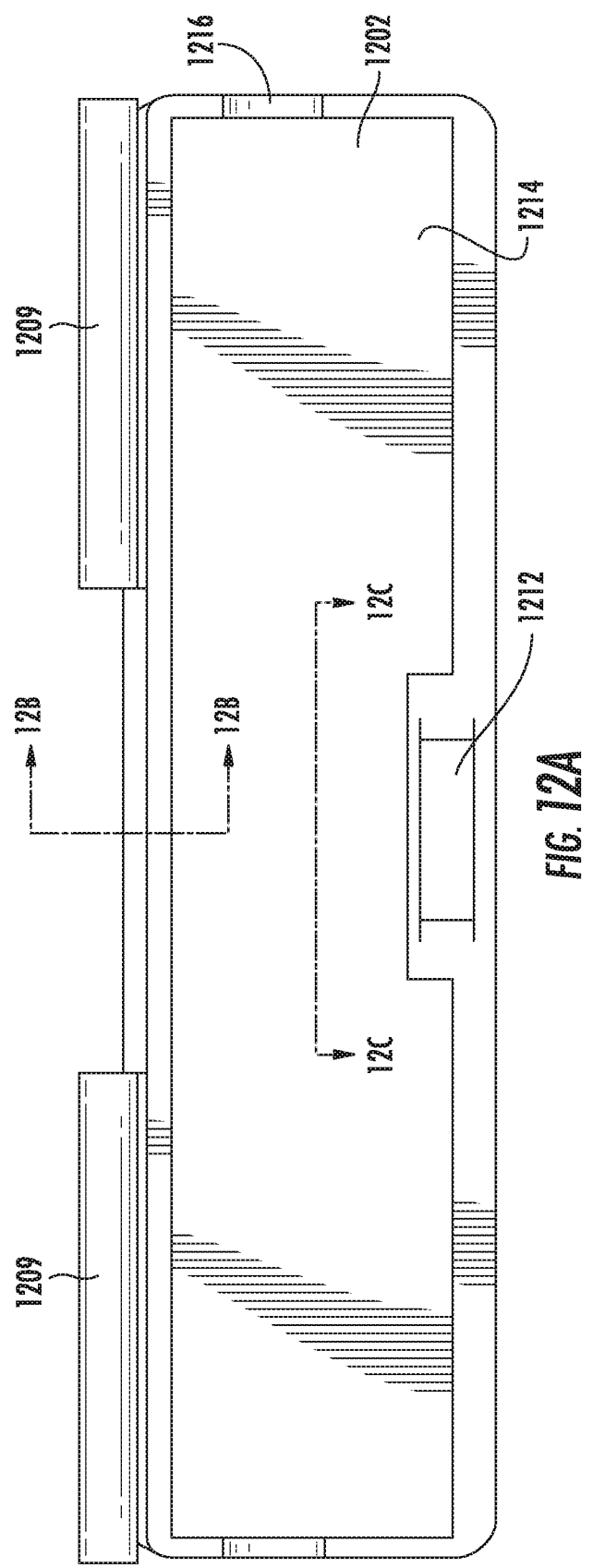

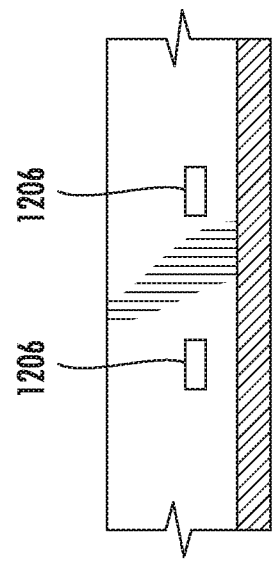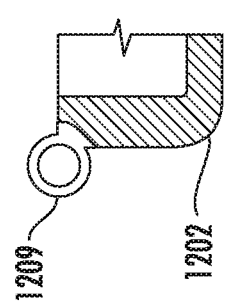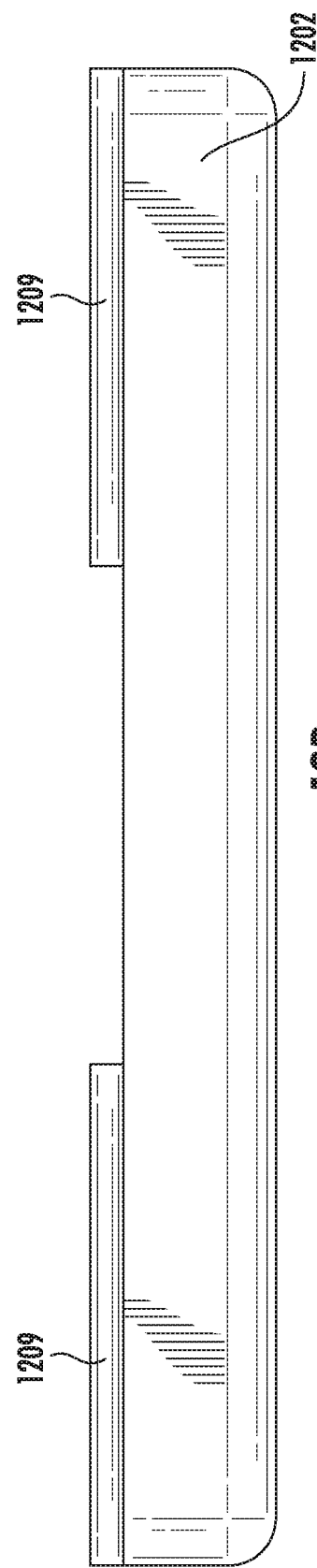

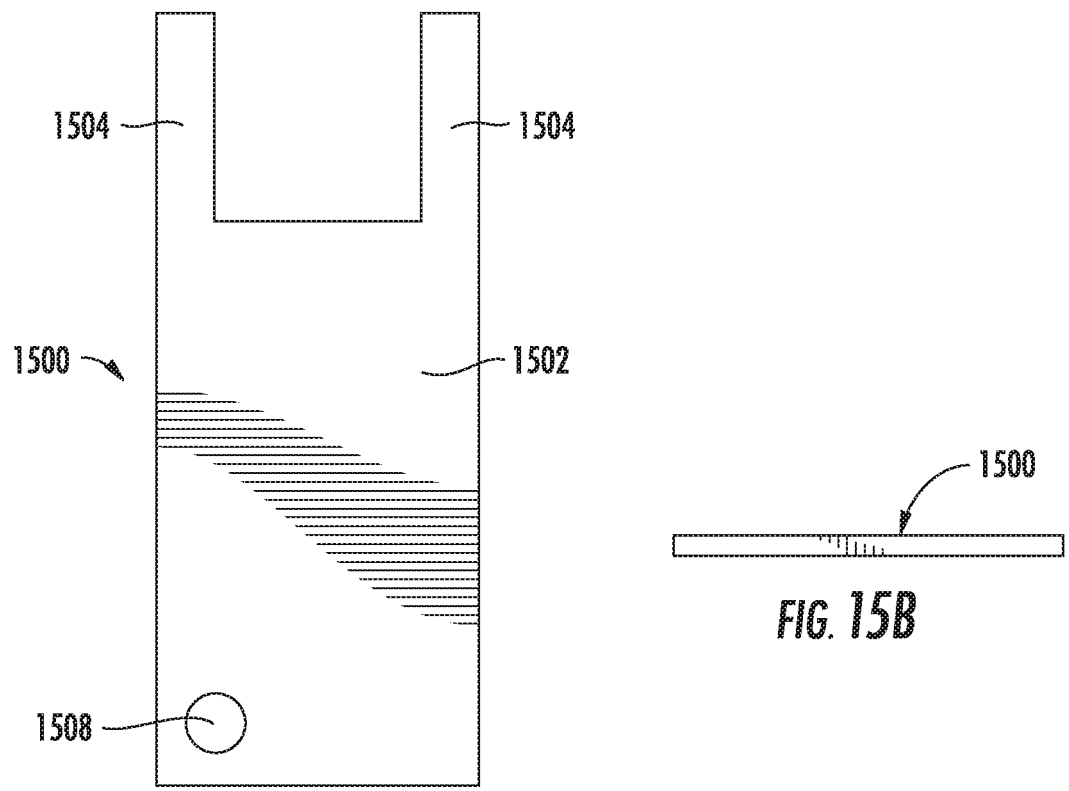
FIG. 15A
FIG. 15B
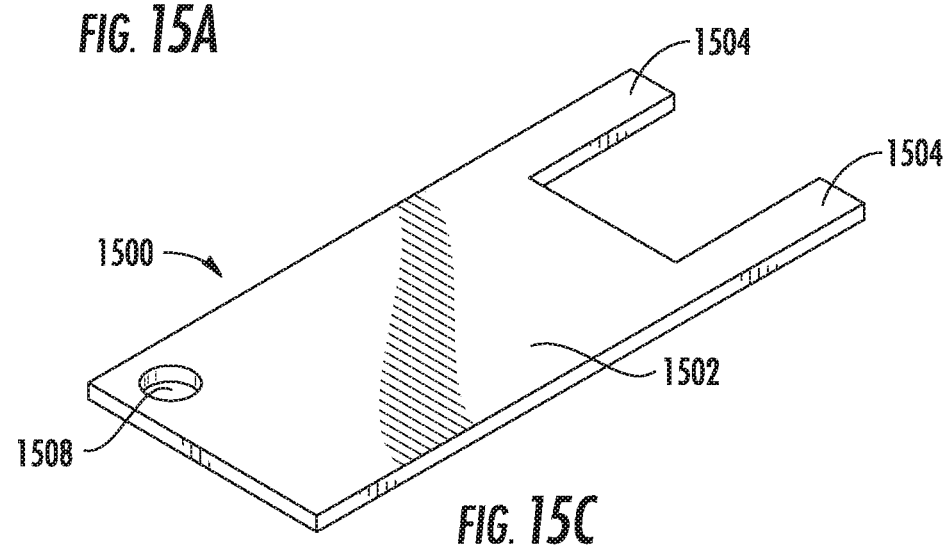
FIG. 15C

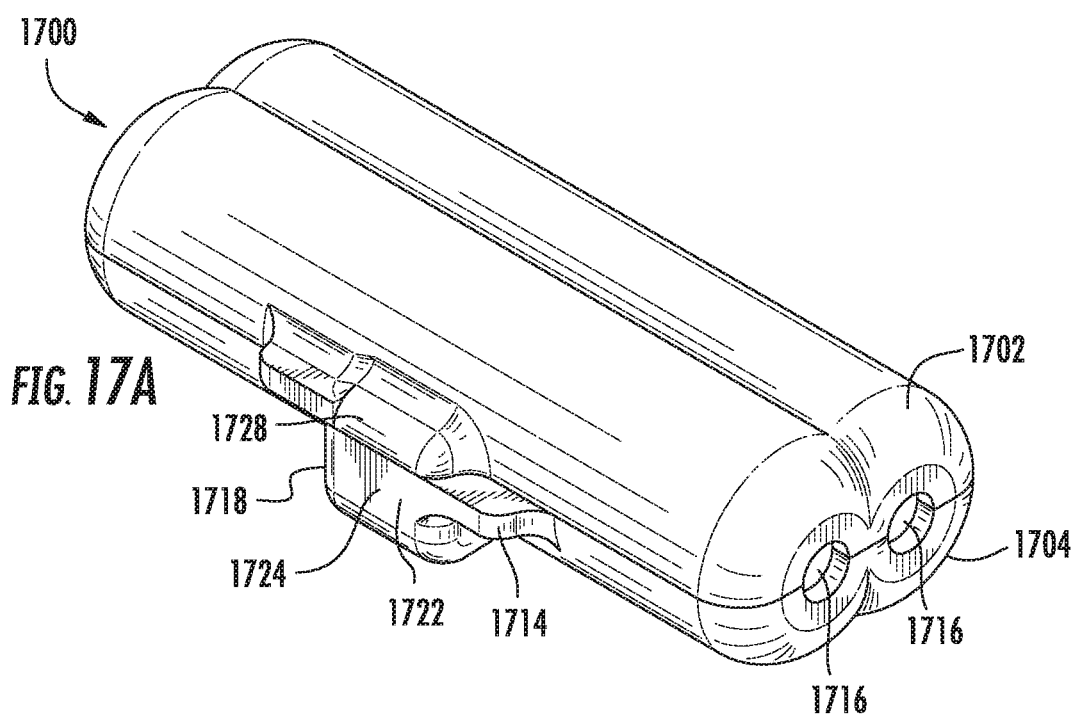
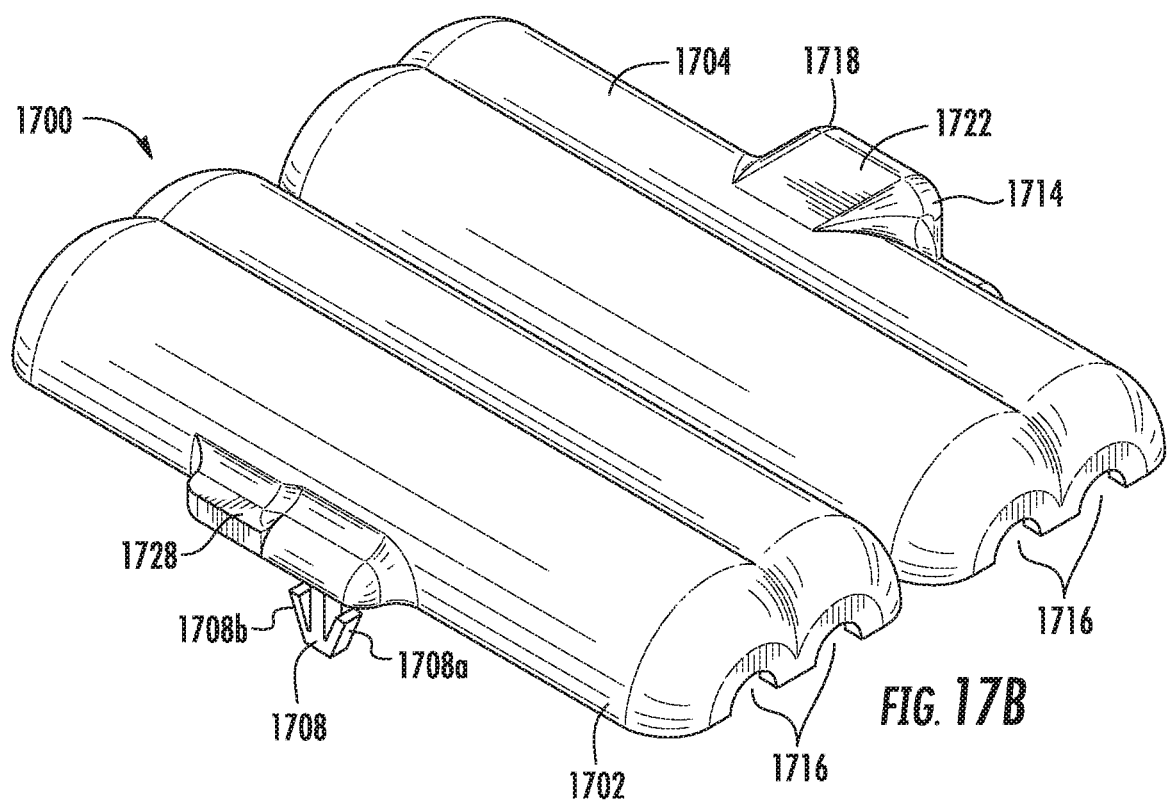

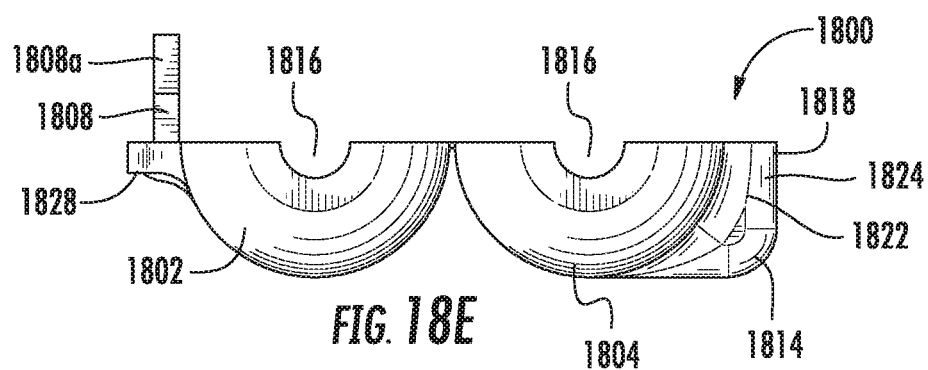
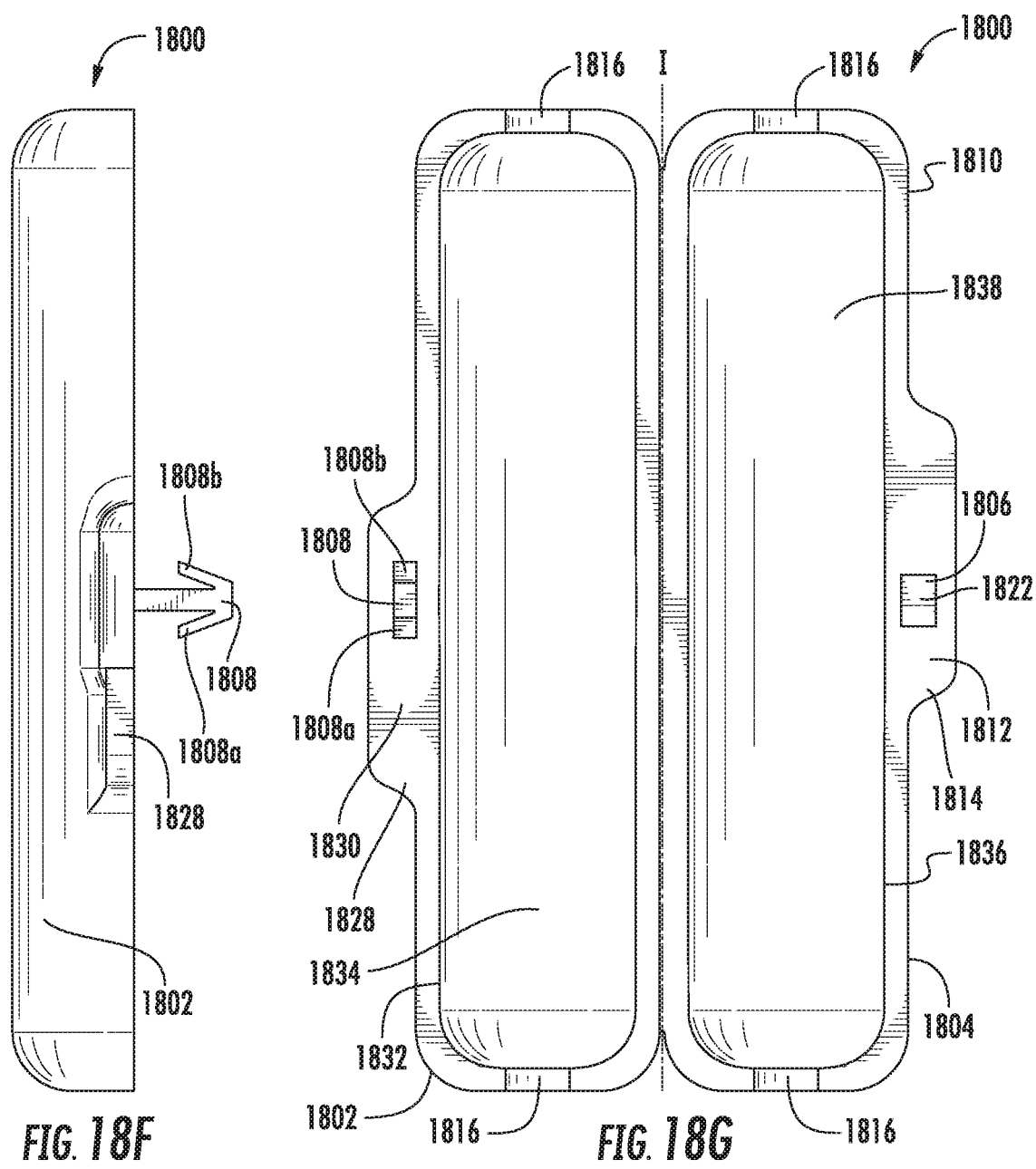

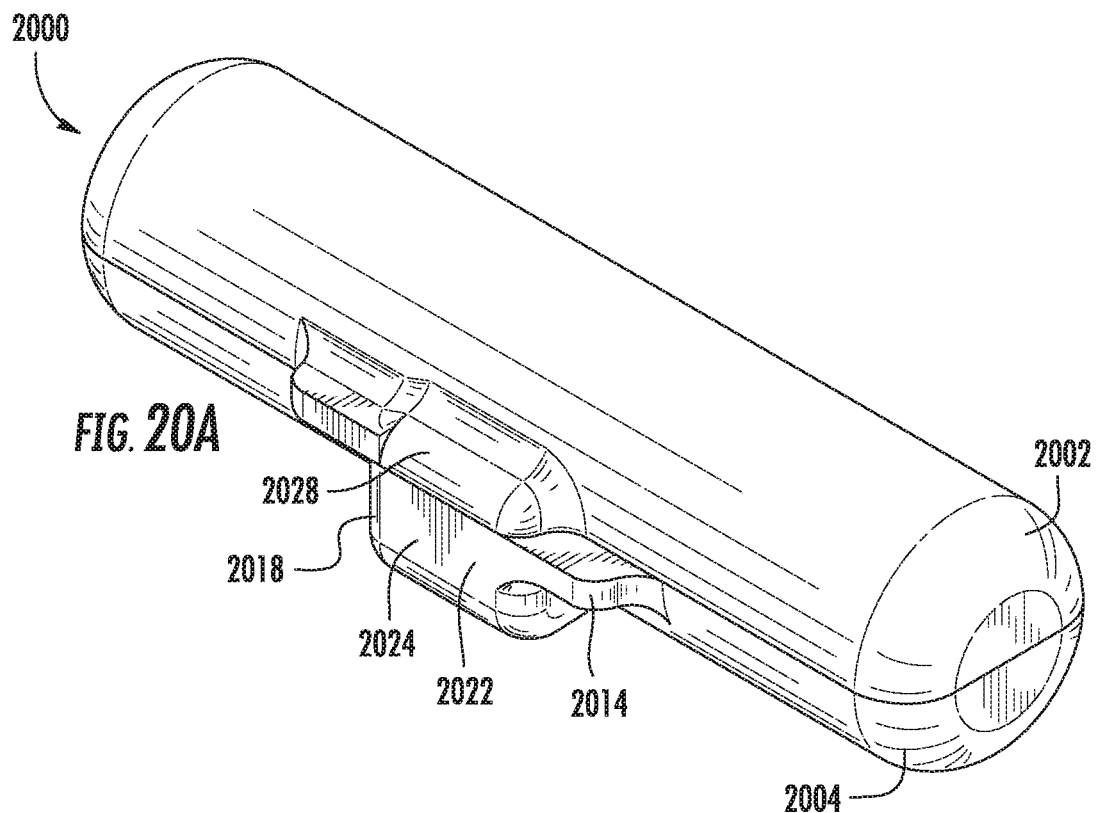
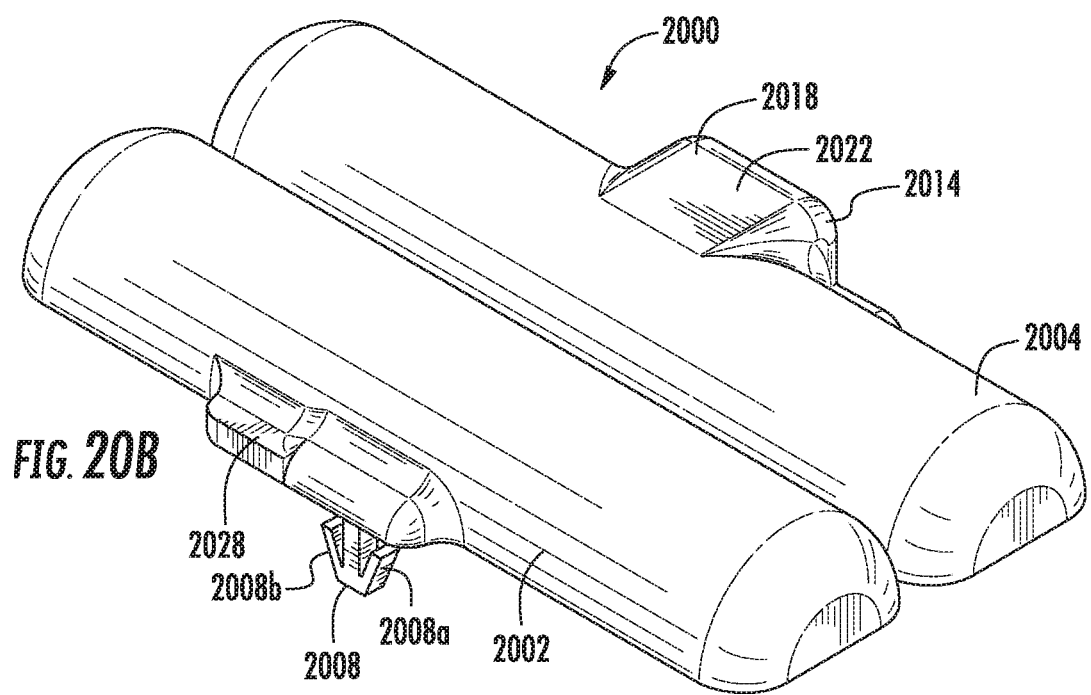

APPARATUSES, SYSTEMS, AND METHODS FOR DETECTION OF TAMPERING

CROSS-REFERENCE TO RELATED APPLICATIONS

This application is a continuation of U.S. patent application Ser. No. 16/456,337, filed Jun. 28, 2019, which is a continuation-in-part of U.S. patent application Ser. No. 15/492,704, filed Apr. 20, 2017, which claims priority to U.S. Provisional Application Ser. No. 62/325,305, filed Apr. 20, 2016, and U.S. Provisional Application Ser. No. 62/384,887, filed Sep. 8, 2016, the disclosures of each of which are herein incorporated by reference in their entireties.

TECHNICAL FIELD

The presently disclosed subject matter relates to methods and apparatuses for detection of tampering, such as with an ingress/egress line, a loaded syringe, and the like. In some embodiments, the ingress/egress line comprises a peripherally inserted central catheter (PICC) line, a midline catheter line, or a regular catheter line.

BACKGROUND

A catheter line, such as, for example, a peripherally inserted central catheter (PICC) line, a midline catheter line or a regular catheter line, is a commonly used form of intravenous access for medical patients, which provides access to the blood stream for various long-term needs (e.g., chemotherapy regimens, extended antibiotic therapy, etc.). One of the main types of risks involved in its use is patient infection, which can be deadly. To decrease the risk of infection, particularly a blood stream infection, those involved in the management of the catheter line or other vessel line must adhere to strict infection control procedures. With certain patients, such as those that are addicted to drugs, the easy-access the inserted line presents is tempting. By merely unscrewing the connections that connect the catheter to the external line, the patient can have direct access to his or her blood stream. In some documented cases, the patients have friends or family, or themselves, directly inject drugs via this line. However, such tampering may result in lack of adequate sanitation and a breach of the strict infection control procedures. With other patients, such as those who are receive catheter or vessel line therapeutic injections as outpatients, the risk of infection is also high due to the lack of adequate sanitation present outside of the hospital environment. Accordingly, for whatever reason, the lack of adequate sanitation inherent with the installation of blood vessel lines may often cause patients to suffer from in-line infections, prolonged hospital stays, and/or death.

As a result, a need exists for a catheter line or other blood vessel line enclosure apparatuses, systems, and methods that may be simple, inexpensive, and quick to use, as well as provide a layer of protection to prevent tampering by a patient and/or any other user. Additionally, a need exists for a catheter line or other blood vessel line enclosure apparatuses, systems, and methods that provide an ability of detection in order to rapidly identify tampering, so that a medical care provider is provided with legal protection from blame for infection and with rapid identification of potential issues before infection is deadly.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a tamper detection apparatus. In some embodiments, the apparatus comprises a clamping box configured for enclosing at least a portion of an object in a manner that provides detection of tampering. In some embodiments, the apparatus comprises a locking mechanism for the clamping box, wherein the apparatus is configured for opening or removal from at least a portion of an object by breaking the clamping box and/or the locking mechanism, or by unlocking the locking mechanism, wherein the opening or removal of the clamping box and/or unlocking of the clamping box is detectable. In some embodiments, the clamping box comprises a first part and a second part attachable to one another, wherein the locking mechanism is configured to maintain the first part of the clamping box and the second part of the clamping box in a closed position.

In some embodiments, the locking mechanism comprises one or more protrusion configured to be inserted in one or more hole disposed on the first part and/or one or more hole disposed on the second part. In some embodiments, the locking mechanism comprises one or more protrusion disposed on the second part configured to engage a recess disposed on the first part. In some embodiments, the apparatus comprises an unlocking mechanism configured to unlock the locking mechanism of the clamping box. In some embodiments, the unlocking mechanism is configured to be inserted in one or more hole disposed on the first part or the second part in order to unlock the clamping box when the first part and the second part of the clamping box are in a closed position.

In some embodiments, the one or more hole disposed on the first part is configured to be aligned with the one or more hole disposed on the second part. In some embodiments, the recess disposed on the first part is configured to be aligned with the one or more protrusion disposed on the second part.

In some embodiments, one or more protrusion is configured to break upon application of force onto one or more protrusion when the first part and the second part of the clamping box are in a closed position, wherein the first part or the second part comprises a compartment adapted to receive the one or more protrusion. In some embodiments, the first part or the second part is configured to provide visual access to the compartment, whereby tampering can be detected upon observation of the one or more protrusion in the compartment. In some embodiments, the first part or the second part is configured such that tampering can be detected upon auditory observation of one or more protrusion in the compartment.

In some embodiments, the one or more protrusion is configured to deform away from the recess upon application of force onto the one or more protrusion when the first part and the second part of the clamping box are in a closed position. In some embodiments, the one or more protrusion is configured to break upon application of force onto the one or more protrusion when the first part and the second part of the clamping box are in a closed position.

In some embodiments, the clamping box is configured for enclosing at least a portion of one or more ingress/egress line in a manner that provides detection of tampering. In some embodiments, the clamping box comprises one or ingress/egress line openings disposed on one or more side surfaces.

In some embodiments, the apparatus further comprises a sticker configured to be applied onto a surface of the clamping box when the clamping box is in the closed position, wherein the sticker is configured to tear upon force.

In some embodiments, the presently disclosed subject matter provides tampering detection system. In some embodiments, the tampering detection system comprises an object; and a clamping box configured for enclosing at least a portion of the object in a manner that provides detection of tampering. In some embodiments, the system comprises a locking mechanism for the clamping box, wherein the apparatus is configured for opening or removal from at least a portion of an object by breaking the clamping box and/or the locking mechanism, or by unlocking the locking mechanism, wherein the opening or removal of the clamping box and/or unlocking of the clamping box is detectable. In some embodiments, the clamping box comprises a first part and a second part attachable to one another, wherein the locking mechanism is configured to maintain the first part of the clamping box and the second part of the clamping box in a closed position. In some embodiments, the locking mechanism comprises one or more protrusion configured to be inserted in one or more hole disposed on the first part and/or one or more hole disposed on the second part. In some embodiments, the locking mechanism comprises one or more protrusion disposed on the second part configured to engage a recess disposed on the first part.

In some embodiments, the system comprises an unlocking mechanism configured to unlock the locking mechanism of the clamping box. In some embodiments, the unlocking mechanism is configured to be inserted in one or more hole disposed on the first part or the second part in order to unlock the clamping box when the first part and the second part of the clamping box are in a closed position.

In some embodiments, the one or more hole disposed on the first part is configured to be aligned with the one or more hole disposed on the second part. In some embodiments, the recess disposed on the first part is configured to be aligned with the one or more protrusion disposed on the second part.

In some embodiments, the one or more protrusion is configured to break upon application of force onto the one or more protrusion when the first part and the second part of the clamping box are in a closed position, wherein the first part or the second part comprises a compartment adapted to receive the one or more protrusion. In some embodiments, the first part or the second part is configured to provide visual access to the compartment, whereby tampering with the apparatus can be detected upon observation of the one or more protrusion in the compartment. In some embodiments, the first part or the second part is configured such that tampering with the apparatus can be detected upon auditory observation of the one or more protrusion in the compartment.

In some embodiments, the one or more protrusion is configured to deform away from the recess upon application of force onto the one or more protrusion when the first part and the second part of the clamping box are in a closed position. In some embodiments, the one or more protrusion is configured to break upon application of force onto the one or more protrusion when the first part and the second part of the clamping box are in a closed position.

In some embodiments, the object is one or more ingress/egress line comprising a first end and a second end and the clamping box is configured for enclosing at least a portion of the one or more ingress/egress line. In some embodiments, the clamping box comprises one or ingress/egress line opening disposed on one or more side surfaces. In some embodiments, a lumen attached to the ingress/egress line is configured to be positioned within the clamping box. In some embodiments, the one or more ingress/egress line comprises two ingress/egress lines, such that the clamping box is configured to enclose at least a portion of each of the two ingress/egress lines therein. In some embodiments, the one or more ingress/egress line comprises a central venous line. In some embodiments, the one or more ingress/egress line comprises one or more peripherally inserted central catheter (PICC) line. In some embodiments, the one or more ingress/egress line comprises one or more midline catheter line. In some embodiments, the one or more ingress/egress line comprises one or more intravenous line.

In some embodiments, the system further comprises a sticker configured to be applied onto a surface of the clamping box when the clamping box is in the closed position, wherein the sticker is configured to tear upon force.

In some embodiments, the presently disclosed subject matter provides a method for detecting tampering with an object. In some embodiments the method comprises positioning an object in a tampering detection apparatus comprising a clamping box configured to provide detection of tampering; and detecting tampering with the object by observing the clamping box. In some embodiments, the tampering detection apparatus comprises a locking mechanism for the clamping box, wherein the apparatus is configured for opening or removal from the at least a portion of an object by breaking the clamping box and/or the locking mechanism, or by unlocking the locking mechanism, wherein the opening or removal of the clamping box and/or unlocking of the clamping box is detectable. In some embodiments, the clamping box comprises a first part and a second part attachable to one another, wherein the locking mechanism is configured to maintain the first part of the clamping box and the second part of the clamping box in a closed position. In some embodiments, the locking mechanism comprises one or more protrusions configured to be inserted in one or more hole disposed on the first part and/or one or more hole disposed on the second part. In some embodiments, the locking mechanism comprises one or more protrusion disposed on the second part configured to engage a recess disposed on the first part.

In some embodiments, the apparatus comprises an unlocking mechanism configured to unlock the locking mechanism of the clamping box. In some embodiments, the unlocking mechanism is configured to be inserted in one or more hole disposed on the first part or the second part in order to unlock the clamping box when the first part and the second part of the clamping box are in a closed position.

In some embodiments, the one or more hole disposed on the first part is configured to be aligned with the one or more hole disposed on the second part. In some embodiments, the recess disposed on the first part is configured to be aligned with the one or more protrusion disposed on the second part.

In some embodiments, the one or more protrusion is configured to break upon application of force onto the one or more protrusion when the first part and the second part of the clamping box are in a closed position, wherein the first part or the second part comprises a compartment adapted to receive the one or more protrusion. In some embodiments, the first part or the second part is configured to provide visual access to the compartment, whereby tampering with the apparatus can be detected upon observation of the one or more protrusion in the compartment. In some embodiments, the first part or the second part is configured such that tampering with the apparatus can be detected upon auditory observation of the one or more protrusion in the compartment.

In some embodiments, the one or more protrusion is configured to deform away from the recess upon application of force onto the one or more protrusion when the first part and the second part of the clamping box are in a closed position. In some embodiments, the one or more protrusion is configured to break upon application of force onto the one or more protrusion when the first part and the second part of the clamping box are in a closed position.

In some embodiments, the object is one or more ingress/egress line comprising a first end and a second end and the clamping box is configured for enclosing at least a portion of the one or more ingress/egress line. In some embodiments, the clamping box comprises one or ingress/egress line opening disposed on one or more side surfaces. In some embodiments, a lumen attached to the ingress/egress line is configured to be positioned within the clamping box. In some embodiments, the one or more ingress/egress line comprises two ingress/egress lines, such that the clamping box is configured to enclose at least a portion of each of the two ingress/egress lines therein. In some embodiments, the one or more ingress/egress line is a central venous line. In some embodiments, the one or more ingress/egress line comprises one or more peripherally inserted central catheter (PICC) line. In some embodiments, the one or more ingress/egress line comprises one or more midline catheter line. In some embodiments, the one or more ingress/egress line comprises one or more intravenous line. In some embodiments, the method comprises inserting the first end of the portion of the one or more ingress/egress line into a patient and connecting the second end of the portion of the one or more ingress/egress line to a supply of fluid.

In some embodiments, detecting tampering comprises observing a broken clamping box or a missing clamping box. In some embodiments, detecting tampering comprises observing a broken clamping box and/or locking mechanism or a missing clamping box. In some embodiments, the clamping box comprises a sticker applied onto a surface of the clamping box when the clamping box is in the closed position, wherein the sticker is configured to tear upon force, and detecting tampering comprises observing a torn sticker.

In some embodiments, the presently disclosed subject matter provides a tamper detection apparatus comprising a clamping box configured for enclosing at least a portion of an object in a manner that provides detection of tampering, wherein the clamping box comprises a first part and a second part attachable to one another; a locking mechanism for the clamping box configured to maintain the first part of the clamping box and the second part of the clamping box in a closed position, wherein the apparatus is configured for opening or removal from the object by breaking the clamping box and/or the locking mechanism; and a compartment in the first part or the second part of the clamping box, wherein the compartment is configured to receive at least a portion of the locking mechanism when the locking mechanism is broken; wherein opening or removal of the clamping box is detectable.

In some embodiments, the locking mechanism comprises one or more protrusions configured to be inserted in one or more hole disposed on the first part and/or one or more hole disposed on the second part. In some embodiments, the locking mechanism comprises one or more protrusion disposed on the second part configured to engage a recess disposed on the first part.

In some embodiments, the apparatus comprises an unlocking mechanism configured to break the locking mechanism of the clamping box. In some embodiments, the unlocking mechanism is configured to be inserted in one or more hole disposed on the first part or the second part.

In some embodiments, the one or more hole disposed on the first part is configured to be aligned with the one or more hole disposed on the second part. In some embodiments, the recess disposed on the first part is configured to be aligned with the one or more protrusion disposed on the second part.

In some embodiments, the first part or the second part is configured to provide visual access to the compartment, whereby tampering with the apparatus can be detected upon observation of the at least a portion of the locking mechanism in the compartment. In some embodiments, the first part or the second part is configured such that tampering with the apparatus can be detected upon auditory observation of the at least a portion of the locking mechanism in the compartment.

In some embodiments, the clamping box is configured for enclosing at least a portion of one or more ingress/egress line in a manner that provides detection of tampering with the apparatus. In some embodiments, the clamping box comprises one or more ingress/egress line openings disposed on one or more side surfaces.

In some embodiments, the apparatus further comprises a sticker configured to be applied onto a surface of the clamping box when the clamping box is in the closed position, wherein the sticker is configured to tear upon force.

In some embodiments, the clamping box comprises one or more openings disposed on one or more side surfaces. In some embodiments, the clamping box comprises an opening disposed on a side surface and wherein the clamping box is closed on an opposite side surface. In some embodiments, the clamping box comprises an opening disposed on a side surface and an opening on an opposite side surface, wherein the openings are not coaxial with respect to each other.

In some embodiments, the locking mechanism comprises one or more protrusion disposed on the second part configured to engage a hole disposed on the first part. In some embodiments, the hole disposed on the first part is configured to be aligned with the one or more protrusion disposed on the second part. In some embodiments, the locking mechanism comprises one or more protrusions configured to be inserted in one or more hole disposed on the first part and/or one or more hole disposed on the second part. In some embodiments, the one or more hole disposed on the first part is configured to be aligned with the one or more hole disposed on the second part.

In some embodiments, the first part and the second part of the clamping box have a periphery that defines an interior of the first part and the second part and the compartment is outside the periphery. In some embodiments, the first part and the second part of the clamping box have a periphery that defines an interior of the first part and the second part and the compartment is inside the periphery. In some embodiments, the first part or the second part is configured to provide visual access to the compartment, whereby tampering with the apparatus can be detected upon observation of the at least a portion of the locking mechanism in the compartment. In some embodiments, the first part or the second part is configured such that tampering with the apparatus can be detected upon auditory observation of the at least a portion of the locking mechanism in the compartment. In some embodiments, the compartment is hidden from a user's view.

In some embodiments, a tampering detection system is provided. In some embodiments, the system comprises an object; and a tamper detection apparatus comprising: a clamping box configured for enclosing at least a portion of an object in a manner that provides detection of tampering, wherein the clamping box comprises a first part and a second part attachable to one another; a locking mechanism for the clamping box configured to maintain the first part of the clamping box and the second part of the clamping box in a closed position, wherein the apparatus is configured for opening or removal from the object by breaking the clamping box and/or the locking mechanism; and a compartment in the first part or the second part of the clamping box, wherein the compartment is configured to receive at least a portion of the locking mechanism when the locking mechanism is broken; wherein opening or removal of the clamping box is detectable.

In some embodiments, the system comprises one or more ingress/egress line comprising a first end and a second end and the clamping box is configured for enclosing at least a portion of the one or more ingress/egress line. In some embodiments, a lumen of the ingress/egress line is configured to be positioned within the clamping box.

In some embodiments, the clamping box comprises one or openings disposed on one or more side surfaces. In some embodiments, the clamping box comprises an opening disposed on a side surface and wherein the clamping box is closed on an opposite side surface. In some embodiments, the clamping box comprises an opening disposed on a side surface and an opening on an opposite side surface, wherein the openings are not coaxial with respect to each other.

In some embodiments, the locking mechanism comprises one or more protrusion disposed on the second part configured to engage a hole disposed on the first part. In some embodiments, the hole disposed on the first part is configured to be aligned with the one or more protrusion disposed on the second part. In some embodiments, the locking mechanism comprises one or more protrusions configured to be inserted in one or more hole disposed on the first part and/or one or more hole disposed on the second part. In some embodiments, the one or more hole disposed on the first part is configured to be aligned with the one or more hole disposed on the second part.

In some embodiments, the first part and the second part of the clamping box have a periphery that defines an interior of the first part and the second part and the compartment is outside the periphery. In some embodiments, the first part and the second part of the clamping box have a periphery that defines an interior of the first part and the second part and the compartment is inside the periphery. In some embodiments, the first part or the second part is configured to provide visual access to the compartment, whereby tampering with the apparatus can be detected upon observation of the at least a portion of the locking mechanism in the compartment. In some embodiments, the first part or the second part is configured such that tampering with the apparatus can be detected upon auditory observation of the at least a portion of the locking mechanism in the compartment. In some embodiments, the compartment is hidden from a user's view.

In some embodiments, the system comprises an unlocking mechanism configured to break the locking mechanism of the clamping box. In some embodiments, the system comprises a sticker configured to be applied onto a surface of the clamping box when the clamping box is in the closed position, wherein the sticker is configured to tear upon force.

In some embodiments, a method for detecting tampering with an object is provided. In some embodiments, the method comprises (a) positioning an object in a tamper detection apparatus comprising: a clamping box configured for enclosing at least a portion of an object in a manner that provides detection of tampering, wherein the clamping box comprises a first part and a second part attachable to one another; a locking mechanism for the clamping box configured to maintain the first part of the clamping box and the second part of the clamping box in a closed position, wherein the apparatus is configured for opening or removal from the object by breaking the clamping box and/or the locking mechanism; and a compartment in the first part or the second part of the clamping box, wherein the compartment is configured to receive at least a portion of the locking mechanism when the locking mechanism is broken; and (b) detecting tampering with the object by observing the clamping box. In some embodiments, the object is one or more ingress/egress line comprising a first end and a second end and the clamping box is configured for enclosing at least a portion of the one or more ingress/egress line.

In some embodiments, the clamping box comprises one or openings disposed on one or more side surfaces. In some embodiments, the clamping box comprises an opening disposed on a side surface and wherein the clamping box is closed on an opposite side surface. In some embodiments, the clamping box comprises an opening disposed on a side surface and an opening on an opposite side surface, wherein the openings are not coaxial with respect to each other.

In some embodiments, the locking mechanism comprises one or more protrusion disposed on the second part configured to engage a hole disposed on the first part. In some embodiments, the hole disposed on the first part is configured to be aligned with the one or more protrusion disposed on the second part. In some embodiments, the locking mechanism comprises one or more protrusions configured to be inserted in one or more hole disposed on the first part and/or one or more hole disposed on the second part. In some embodiments, the one or more hole disposed on the first part is configured to be aligned with the one or more hole disposed on the second part.

In some embodiments, the first part and the second part of the clamping box have a periphery that defines an interior of the first part and the second part and the compartment is outside the periphery. In some embodiments, the first part and the second part of the clamping box have a periphery that defines an interior of the first part and the second part and the compartment is inside the periphery. In some embodiments, the first part or the second part is configured to provide visual access to the compartment, whereby tampering with the apparatus can be detected upon observation of the at least a portion of the locking mechanism in the compartment. In some embodiments, the first part or the second part is configured such that tampering with the apparatus can be detected upon auditory observation of the at least a portion of the locking mechanism in the compartment. In some embodiments, the compartment is hidden from a user's view.

Accordingly, it is an object of the presently disclosed subject matter to provide methods and apparatuses for detection of tampering, such as with an ingress/egress line. This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description.

BRIEF DESCRIPTION OF THE DRAWINGS

Preferred embodiments of the drawings will now be described of which:

FIG. 6A is a top perspective view including an enlarged inset illustrating a second embodiment of a clamping box in an unlocked position for a blood vessel line enclosure apparatus according to the presently disclosed subject matter;

FIGS. 9A-9D are perspective views illustrating a method for using a blood vessel line enclosure system using the first embodiments of the clamping box and the unlocking mechanism illustrated in FIGS. 4A-4D and 5A-5B, respectively;

FIG. 11A is a top view illustrating part 1104 of a fourth embodiment of a line enclosure apparatus according to the presently disclosed subject matter;

FIG. 12A is a top view illustrating part 1202 of a fourth embodiment of a line enclosure apparatus according to the presently disclosed subject matter;

FIG. 12B is a section view taken along the line 12B-12B in FIG. 12A illustrating part 1202 of a fourth embodiment of a line enclosure apparatus according to the presently disclosed subject matter;

FIG. 12C is a section view taken along the line 12C-12C in FIG. 12A illustrating one or more hole 1206 of a fourth embodiment of a line enclosure apparatus according to the presently disclosed subject matter;

FIG. 12D is a front view illustrating part 1202 of a fourth embodiment of a line enclosure apparatus according to the presently disclosed subject matter;

FIG. 15A is a top plan view illustrating a third embodiment of an unlocking mechanism for the line enclosure apparatus illustrated in FIGS. 11A-11E, 12A-12F, and 14A-14D;

FIG. 15B is an end view illustrating a third embodiment of an unlocking mechanism for the line enclosure apparatus illustrated in FIGS. 11A-11E, 12A-12F, and 14A-14D;

FIG. 15C is a perspective view illustrating a third embodiment of an unlocking mechanism for the line enclosure apparatus illustrated in FIGS. 11A-11E, 12A-12F, and 14A-14D;

FIG. 17A is a perspective view illustrating a sixth embodiment of a line enclosure apparatus according to the presently disclosed subject matter;

FIG. 17B is a perspective view illustrating an outside of a sixth embodiment in an open or unlocked position according to the presently disclosed subject matter;

FIG. 18E is an end view illustrating a seventh embodiment of a line enclosure apparatus in an open or unlocked position according to the presently disclosed subject matter;

FIG. 18F is a side view illustrating a seventh embodiment of a line enclosure apparatus in an open or unlocked position according to the presently disclosed subject matter;

FIG. 18G is a top view illustrating a seventh embodiment of a line enclosure apparatus in an open or unlocked position according to the presently disclosed subject matter;

FIG. 20A is a perspective view illustrating a ninth embodiment of a line enclosure apparatus according to the presently disclosed subject matter;

FIG. 20B is a perspective view illustrating an outside of a ninth embodiment in an open or unlocked position according to the presently disclosed subject matter;

Figures 1, 2, 3:
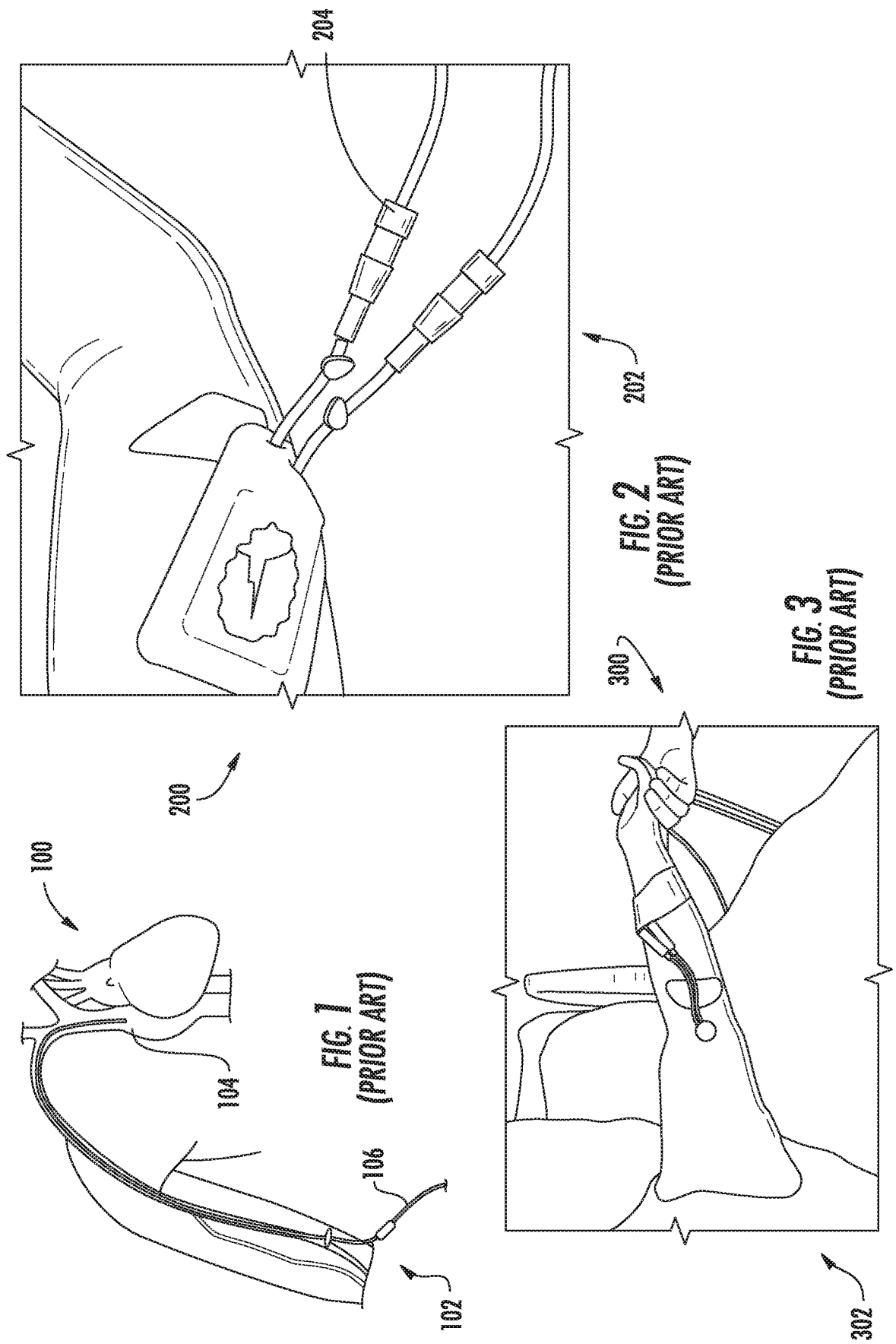
FIG. 1 is a drawing illustrating a blood vessel line, in this case a peripherally inserted central catheter (PICC) line, in a patient according to the prior art.
FIG. 2 is a drawing illustrating a PICC line in a patient with screw-on connections to a supply of fluid according to the prior art.
FIG. 3 is a drawing illustrating a PICC line in a patient with an infection along the PICC line according to the prior art.
Figure 4A:
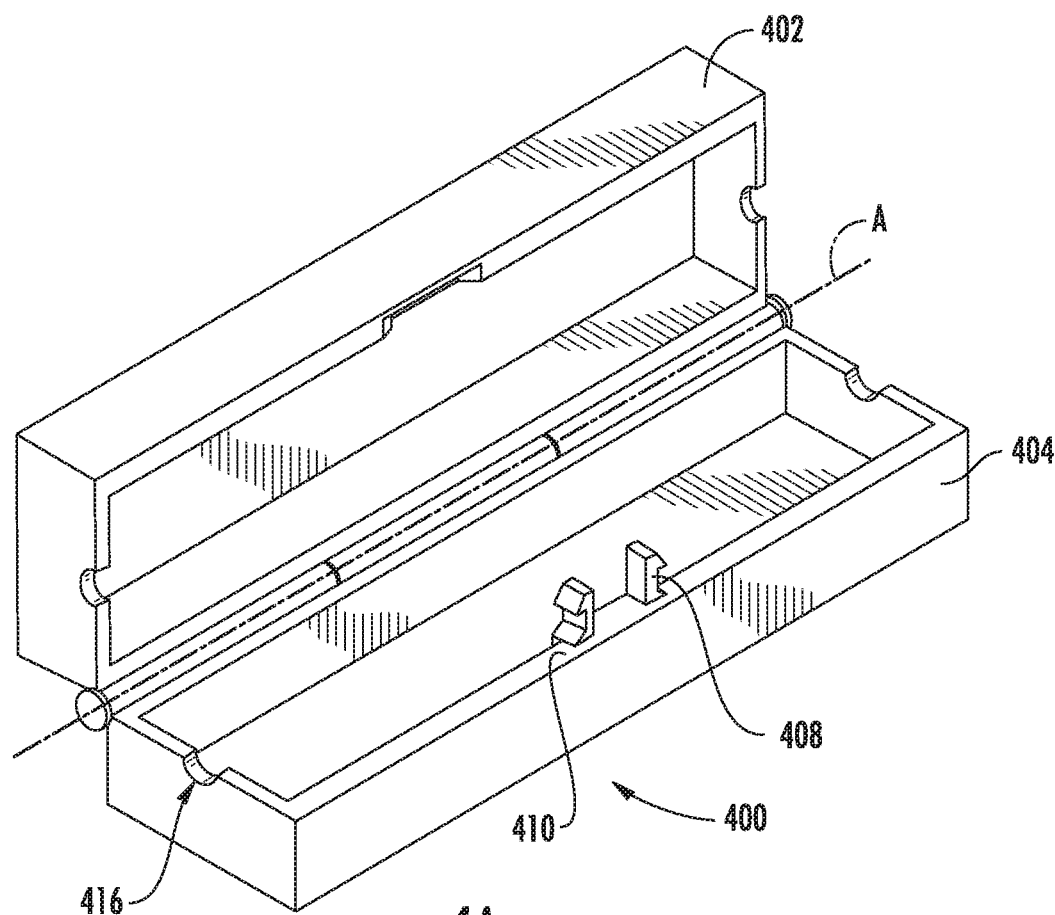
FIG. 4A is a top perspective view illustrating a first embodiment of a clamping box in an unlocked position for a blood vessel line enclosure apparatus according to the presently disclosed subject matter.
Figure 4B:
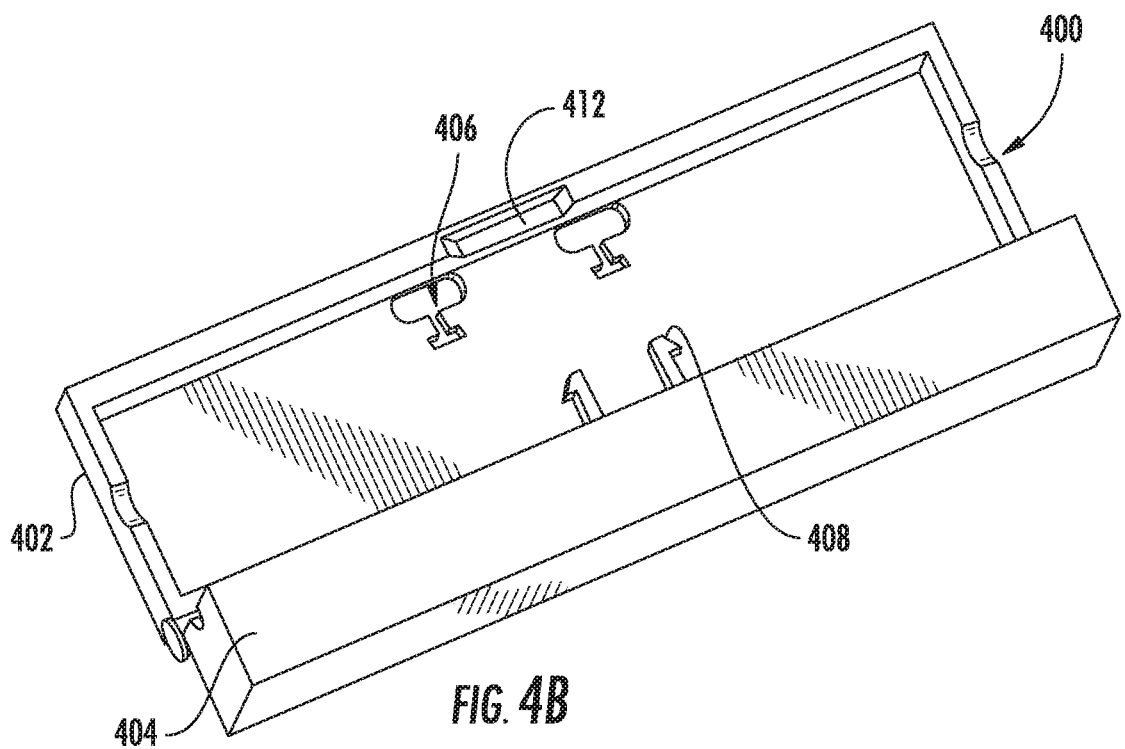
FIG. 4B is a front perspective view illustrating a first embodiment of a clamping box in an unlocked position for a blood vessel line enclosure apparatus according to the presently disclosed subject matter.
Figure 4C:
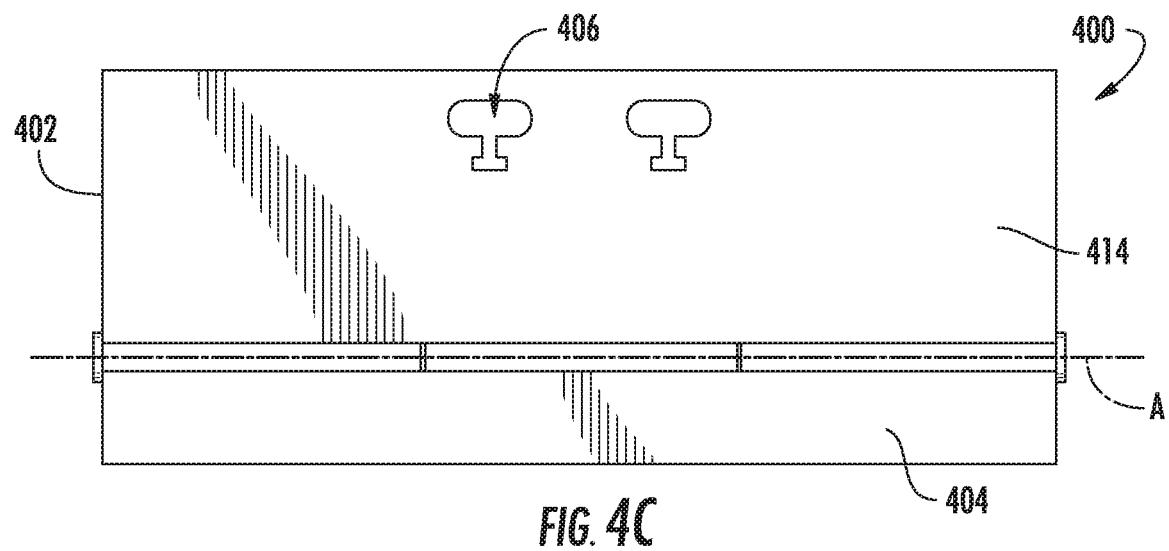
FIG. 4C is a front view illustrating a first embodiment of a clamping box in an unlocked position for a blood vessel line enclosure apparatus according to the presently disclosed subject matter.
Figure 4D:
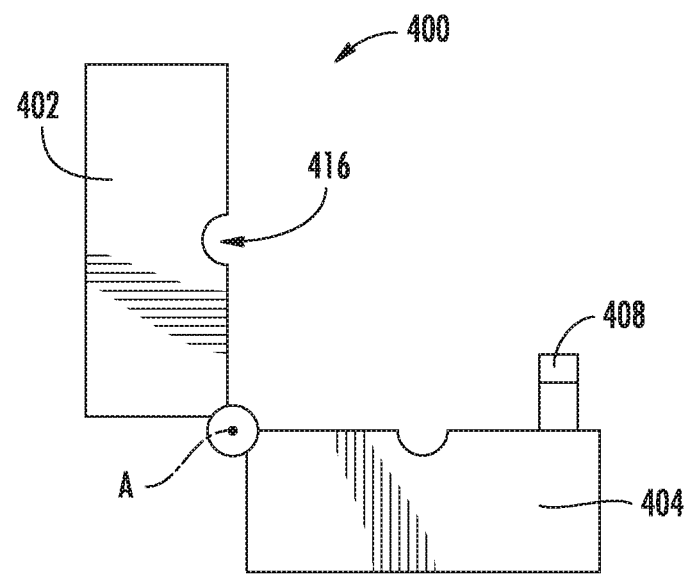
FIG. 4D is a side view illustrating a first embodiment of a clamping box in an unlocked position for a blood vessel line enclosure apparatus according to the presently disclosed subject matter.

References herein and in the Figures to certain particular dimensions are merely meant to be exemplify the presently disclosed subject matter and not to limit the presently disclosed subject matter.

DETAILED DESCRIPTION

The presently disclosed subject matter will now be described more fully. The presently disclosed subject matter can, however, be embodied in different forms and should not be construed as limited to the embodiments set forth herein below. Rather, these embodiments are provided so that this disclosure will be thorough and complete, and will fully convey the scope of the embodiments to those skilled in the art.

The terms "catheter line", "central venous line", "blood vessel line", and "vessel line" are used herein interchangeably herein and in a manner that is consistent with how one of ordinary skill in the art of the invention would understand these terms. A peripherally inserted central catheter (PICC) line, midline catheter line, and other non-central catheter lines are some examples of a "blood vessel line" or a "vessel line" that are commonly used to gain intravenous access to the blood stream for long term medical needs. In some embodiments, the enclosure apparatuses, systems, and methods described in the following figures and descriptions may be configured with an exemplary PICC, midline catheter, or other non-central catheter line, although the enclosure apparatuses, systems, and methods may be configured to be used with other numbers, kinds, shapes, sizes, etc., of "catheter line(s)", "central venous line", "blood vessel line(s)", or "vessel line(s)".

In some embodiments, the enclosure apparatuses, systems, and methods described in the following figures and descriptions may be configured to be used with other numbers, kinds, shapes, sizes, etc., of ingress and/or egress (referred to herein as "ingress/egress") lines attachable to a vessel, container, bag, etc., containing matter of some type or adapted to receive matter of some type for use with a patient or subject. For example, the enclosure apparatuses, systems, and methods may be described in the following figures and descriptions may be configured to be used with a colostomy bag, drug bag, infusion bag etc. Thus, in some embodiments, the enclosure apparatuses, systems, and methods described in the following figures and descriptions can have a different profile and hole locations to accommodate the configuration of the exit of the infusion bag or drug bag. By way of example and not limitation, the enclosure apparatuses, systems, and methods described in the following figures and descriptions can comprise the implementation of a clamping box over a T shaped line, e.g., one line going in and 2 lines coming out. Thus, enclosure apparatuses, systems, and methods in accordance with the presently disclosed subject matter can include any number of lines going in to the apparatus, such as into the clamping box of the apparatus, and any number of lines coming out of the apparatus, such as out of the clamping box of the apparatus. Also, in some embodiments the enclosure apparatuses, systems, and methods in accordance with the presently disclosed subject matter includes no holes on side surfaces and thus can serve to enclose at least a portion of an object in this manner. The enclosure apparatuses, systems, and methods in accordance with the presently disclosed subject matter also provide for the detection of tampering, including through the provision of a compartment, such as a hidden compartment, as described herein.

In some aspects, the enclosure apparatus and/or systems described herein may be manufactured via three-dimensional or (3D) printing in a manner that is consistent with how one of ordinary skill in the art of the invention would understand. In other aspects, the enclosure apparatus and/or systems described herein may be extruded, injection molded, and/or manufactured via any method that provides a blood vessel line enclosure apparatus and/or system that is configured to prevent and/or detect tampering by a patient and/or any other user. In some aspects, the presently disclosed subject matter provides a blood vessel line enclosure apparatus and/or system that is configured to provide medical care provider(s) with an ability to rapidly identify tampering or other manipulation by non-medical personnel, so that the medical care provider(s) is/are provided with an ability to head off potential patient health issues sooner and with legal protection from blame for infection associated with tampering. As used herein, the term "tampering" refers to intentional and unintentional manipulation. An example of unintentional manipulation might be found in the case where the patient with whom the apparatus is used suffers from a mental deficit that makes the patient not be able to appreciate the significance of the manipulation.

In some embodiments, two holes are provided as inlet and outlet: this is for continuous infusion e.g. when intravenous (IV) therapy is on. In some embodiments, the device includes only one hole and is covered on the other side (that is, only inlet and no outlet). In these embodiments, the line is not used for therapy. There is no tamper-evident device in the market that can be used for both continuous infusion and while the line is not used for infusion. Also, the presently disclosed device does not pinch or crimp the line or leave sticky residue on the line. In some embodiments, the device does not touch the line; rather, it only covers the lumen interface points, i.e. the region of interest. The device can be used for single use, multiple use, and can hold either single or multiple lines. When a health care professional locks the box, she checks to ensure the lock is intact. Before she opens the device to start the therapy she also checks to ensure the lock is intact. If the lock appears to be broken then she knows the device has been tampered with. In some embodiments the device comprises a hidden chamber, and the hidden chamber could either be inside the clamping box or outside the clamping box. By way of example, the device can be made either with injection molding or 3D printing.

In accordance with some embodiments, methods, apparatuses, and systems of the presently disclosed subject matter provide easy tamper detection, such as with respect to a PICC, midline catheter lines, drug bags, infusion bags, or other lines. In accordance with some embodiments, methods, apparatuses, and systems of the presently disclosed subject matter provide easy tamper detection in settings outside of a medical or patient treatment setting. Such settings can comprise access to water lines or other water infrastructure, access to electrical lines or other electrical infrastructure, access to communications lines or other communications infrastructure, and the like. Indeed, methods, apparatuses, and systems of the presently disclosed subject matter can be implemented in any setting as would be apparent to one of ordinary skill in the art upon review of the instant disclosure where tamper detection is desired.

Thus, in some embodiments, the presently disclosed subject matter relates to a tampering detection apparatus, such as might be employed as an ingress/egress line enclosure apparatus. In some embodiments, the tampering detection apparatus can comprise a clamping box configured for enclosing at least a portion of one or more structure, such as one or more line, such as one or more ingress/egress line, in a manner wherein detection of tampering with the apparatus is provided. Thus, the presently disclosed subject matter provides approaches to seal a box and affirmatively indicate that the box was opened. In some embodiments, the presently disclosed subject matter includes a box sealed with commercially available tamper evident stickers/tape, snap seals, padlock seals, and the like. Such items can be referred to locking mechanisms. Thus, in some embodiments, the presently disclosed subject matter includes holes or loops in which to insert a security seal. In some embodiments, tabs for a seal might hang off the front of the box or other portion of the box. Loops can be positioned so that a security seal can be wrapped around the box. In some embodiments, a sticker can be placed along one or more points of connection between box parts to seal the box parts closed and also act as an indicator for tampering. In some embodiments, no unlocking device such as a key is necessary. The user can break the box or break or open the locking mechanism by hand. By way of example and not limitation, security seals are usually removed by breaking along score marks or by using wire cutters. In some embodiments, the clamping box has a latch, which can be referred to as a locking mechanism, but which does not need an unlocking mechanism or which uses an unlocking mechanism that does not need to be inserted into the box. Thus, the locking mechanism can refer to any mechanism that can maintain the clamping box in a closed position but does not necessarily require an unlocking mechanism, such as a key, to open the box. Other examples include a padlock seal, such as can be found through the World Wide Web at site www.hmark.com/tamperevident-seals. Tamper evident stickers/tape, snap seals, padlock seals, can be ordered in any desired size. Another example of a clamping box that does not need an unlocking mechanism includes a box in which foil stickers/tape are/is put on it such that when the box is opened it would be possible to detect tampering as the sticker/tape would be cut or torn open. In such examples, the box can be reusable and may not need a key to open it.

In some embodiments, the enclosure apparatus and/or system described herein comprise a tamper detection design wherein the apparatus is adapted to be opened by hand. In some embodiments, it does take some force to do so; that is, it does not break easily. In some embodiments, the enclosure apparatus and/or systems described herein can be opened with a key or other unlocking mechanism but in doing so the key breaks the "lock" and the box is not re-useable. Either method (i.e., opening by hand or by key) that is used to try and access IV lines or other lines breaks the apparatus, thereby enabling detection of tampering or other unauthorized access to the lines. Thus, in some embodiments, unauthorized unlocking from the locked position by insertion of the unlocking mechanism is detectable. Further, in some embodiments, the enclosure apparatus and/or systems described herein comprise a disposable box.

While representative locking and unlocking mechanism(s) are described herein with respect to particular embodiments, any suitable locking and/or unlocking mechanism as would be apparent to one of ordinary skill in the art upon a review of the instant disclosure can be employed in accordance with the presently disclosed subject matter. Exemplary locking and/or unlocking mechanisms may include those such as latches, screws, springs, key and tumblers, and the like.

Referring to FIG. 1, drawing 100 is of a torso of a patient with a PICC line 102 inserted therein. PICC line 102 comprises a first end 104 that extends through a skin of the patient into a superior vena cava of the patient and a second end or catheter tail 106 that remains outside a skin of the patient. In some aspects, and as illustrated in drawing 202 in FIG. 2, a catheter 200 may have a second end or catheter tail 204 in connection with a supply of fluid. For example, catheter tail 204 may be connected via a screw-on connection with a supply of fluid. However, by merely unscrewing the connection(s) that connect the catheter to the external line, a patient may have direct access to his blood stream, which may result in-line infections. As illustrated in drawing 300 in FIG. 3, for example, a PICC line 302 is inserted into a patient, where there is an infection along PICC line 302. In such an instance, tampering with PICC line 302 may have resulted in the infection. Accordingly, blood vessel line (such as but not limited to PICC line) enclosure apparatuses, systems, and methods, as disclosed herein, may be utilized to prevent or deter tampering by a patient and/or any other user, and to provide easy detection of tampering. In accordance with the presently disclosed subject matter, then, a medical care provider is provided with the ability to more rapidly identify potential patient heath issues such as infection and also with legal protection from blame for infection associated with tampering.

Several embodiments of a blood vessel line enclosure apparatus follow. In some embodiments, the blood vessel line enclosure apparatus is configured to enclose one or more blood vessel line(s) therein in order to protect the one or more blood vessel line(s) from a sanitation standpoint (e.g., dirt, bacteria, etc.). In some embodiments, the blood vessel line enclosure apparatus is also configured to prevent or deter tampering, and to allow medical personnel to quickly identify and/or detect if any tampering has occurred.

A first embodiment of a blood vessel line enclosure apparatus is provided in FIGS. 4A-4D and FIGS. 5A-5B. Referring now to FIGS. 4A-4D, a clamping box 400 for enclosing at least a portion of a blood vessel line, such as a PICC line, therein is illustrated in various views. Clamping box 400 can comprise a first part 402 and a second part 404 that are attachable to one another. For example, first part 402 and second part 404 are configured to pivot with respect to one another via a pivot axis A defined by longitudinally extending first side edges of both the first part 402 and the second part 404. Notably however, first part 402 and second part 404 part may relate to one another in a manner other than pivoting. For example, a hinge, screw, spring, and/or any other mechanism may allow one or more part of clamping box 400 to move relative to one another in order to enclose the blood vessel line within. Regardless, first part 402 and second part 404 may be manipulated into a locked position and an unlocked position. For example, first part 402 and second part 404 may pivot along pivot axis A into a first or unlocked position where first part 402 and second part 404 are not in direct contact along second longitudinally extending side edges, where the second longitudinally extending side edges are disposed opposite the first longitudinally extending side edges (see, FIGS. 4A-4D). In another example, first part 402 and second part 404 may pivot along pivot axis A into a second or locked position where first part 402 and second part 404 are in direct contact along the second longitudinally extending side edges (see, FIG. 9B). In some aspects, clamping box 400 may comprise more or less than first part 402 and second part 404, each of which may be manipulated into locked and/or unlocked positions. For example, clamping box 400 may comprise one part, three parts, four parts, etc.

In some aspects, clamping box 400 may have a substantially rectangular prism shape such that each of first part 402 and second part 404 form a rectangular prism when pivoted into the locked position. Alternately, in some aspects, clamping box 400 may have any geometric shape with some basic functionality allowing clamping box 400 to enclose the blood vessel line within. For example, clamping box 400 may be square, ovular, triangular, etc., and/or the edges of clamping box 400 may be rounded (see, for example, a line enclosure apparatus in accordance with the presently disclosed subject matter as shown in FIGS. 11A-11E, 12A-12F, and 14A-14D), pointed, non-uniform, etc. In other aspects, each box may be manufactured according to the measurements of an extremity of a patient so that the box contours to that extremity. For example, clamping box 400 may be sized and shaped to conform to a patient's arm.

In some aspects, first part 402 and second part 404 are configured to lock relative to one another. A locking mechanism disposed on either one or both of first part 402 and second part 404 may be provided in order to prevent a patient and/or other user from easily gaining entry to the blood vessel line enclosed by clamping box 400. However, the locking mechanism may be weak enough to allow for a patient and/or other user to gain entry, if the patient and/or other user is determined to do so. But the locking mechanism is configured so that if tampering does occur, it is easily and quickly detectable by medical personnel. As illustrated in FIGS. 4A-4D, for example, the locking mechanism on clamping box 400 comprises a hole or recess 412 disposed on the second longitudinally extending side edge of first part 402 and one or more protrusion 408 disposed on the second longitudinally extending side edge of second part 404. One or more protrusion 408 may be substantially aligned with recess 412 disposed on the second longitudinally extending side edge of second part 404. One or more hole 406 disposed on first part 402 may be provided in order to unlock clamping box 400, to be described in more detail below.

One or more hole 406 may be disposed on a top surface 414 of first part 402 of clamping box 400. In some aspects, for example, one or more hole 406 may be disposed towards a front edge of top surface 414 and disposed centrally relative to a front edge of top surface 414. One or more hole 406 can comprise an opening sized and/or shaped so that an unlocking mechanism, e.g., unlocking mechanism 500, FIGS. 5A-5B, may be inserted therethrough. In some aspects, at least a portion of the opening of one or more hole 406 may be aligned with one or more protrusion 408 such that an unlocking mechanism may be configured to manipulate one or more protrusion 408 upon insertion in one or more hole 406.

One or more protrusion 408 may comprise two protrusions each comprising an edge surface 410, which can be chamfered. Edge surface 410 may comprise an angled surface and a planar surface substantially parallel to the second longitudinally extending side edge of second part 404. Edge surface 410 may comprise other geometries, shapes, sizes, and/or positions, such as a curved shape. In some aspects, one or more protrusion 408 may be configured to be manipulated. For example, when first part 402 and second part 404 are pivoted into the locked position, one or more protrusion 408 may be deformed inwardly to fit within the confines of recess 412. In this example, the edge surface 410 of each of one or more protrusion 408 may press outwardly in an opposite direction against a side wall of recess 412.

In some aspects, clamping box 400 may be sized to fit at least a portion of a standard blood vessel line therein. For example, a 4 French or larger or smaller in size lumen (see, FIG. 9A, 902B) of a PICC line may be configured to fit within clamping box 400. In this manner, each of the first part 402 and the second part 404 may be formed as hollow halves in order to receive at least a portion of a blood vessel line therein. In some aspects, either one or both of first part 402 and second part 404 of clamping box 400 comprise blood vessel line openings 416 disposed on opposing side surfaces of clamping box 400. For example, blood vessel line openings 416 may comprise semi-circular openings that may allow the blood vessel line to enter and exit clamping box 400 when the clamping box is in the locked position.

Figure 5A:
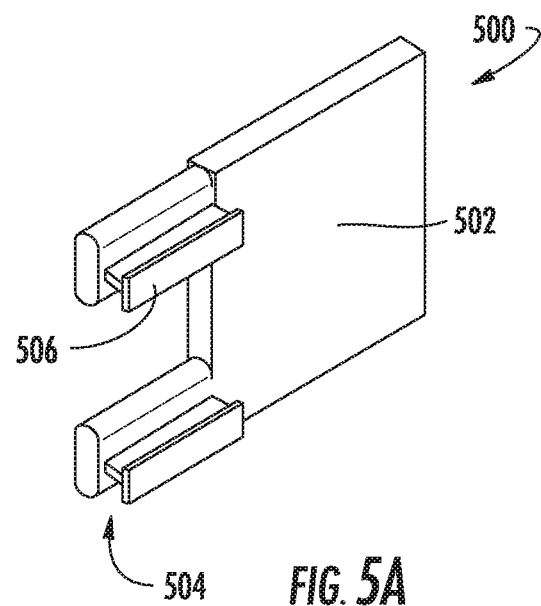
FIG. 5A is a perspective view illustrating a first embodiment of an unlocking mechanism for the clamping box illustrated in FIGS. 4A-4D.
Figure 5B:
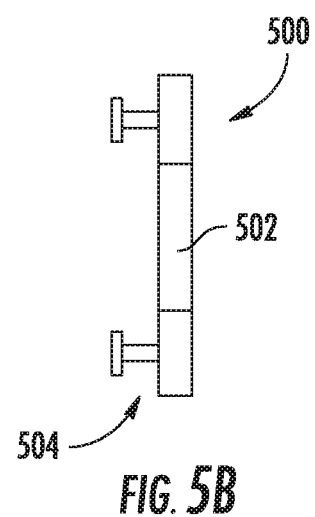
FIG. 5B is a side view illustrating a first embodiment of an unlocking mechanism for the clamping box illustrated in FIGS. 4A-4D.

Referring now to FIGS. 5A-5B, an unlocking mechanism 500 for unlocking clamping box 400 illustrated in FIGS. 4A-4D is illustrated in various views. Unlocking mechanism 500 may comprise a planar surface 502 that may be substantially square in shape for easy gripping and/or handling by medical personnel. Other shapes, sizes, geometries, etc., for providing basic unlocking functionality are contemplated as well. Extending from planar surface 502 is one or more extension 504, which may be sized and/or shaped to comprise teeth 506. Together one or more extension 504 and teeth 506 may correspondingly fit within the one or more hole 406 illustrated in FIGS. 4A-4D. For example, in FIGS. 5A-5B, one or more extension 504 is formed as a substantially an elongated cylinder and is shaped to comprise a rectangular tooth 506. In profile, one or more extension 504 and teeth 506 correspond to a size and shape of one or more hole 406 in FIGS. 4A-4D. Thus, in this example, one or more hole 406 is sized and shaped to receive a corresponding one of the one or more extension 504 and teeth 506 upon insertion of unlocking mechanism 500 when clamping box 400 is in a locked position (see FIG. 9C).

Accordingly, in a first embodiment of the blood vessel line enclosure apparatus illustrated in FIGS. 4A-5B, to unlock clamping box 400, one or more extension 504 of unlocking mechanism 500 may be inserted into a corresponding one or more hole 406 of clamping box 400 and pressed against edge surface 410 of a corresponding one of one or more protrusion 408 in order to elastically deform the one or more protrusion inwardly and away from recess 412. Once each edge surface 410 is deformed inwardly and no longer in contact with side edges of recess 412, first part 402 and second part 404 of clamping box 400 may be rotated about pivot axis A away from one another and into an unlocked and/or open position. Notably, one or more protrusion 408 is elastically deformed upon insertion of unlocking mechanism 500. As is known in the art, elastic deformation results in a temporary shape change that is self-reversing after the force is removed. Therefore, once the force is removed from edge surface 410 and first part 402 and second part 404 are pivoted into the unlocked position, one or more protrusion 408 returns to its original position. Thus, the first embodiment is a multi-use apparatus, as unlocking mechanism 500 and clamping box 400 may be utilized multiple times. Notably, however, a multi-use apparatus may be configured in manner different than the clamping box 400 and unlocking mechanism 500 illustrated in FIGS. 4A-5B. For example, a multi-use apparatus may comprise one or more hole disposed on a front surface or side surfaces, while unlocking mechanism 500 may not comprise any teeth.

Figure 6B:
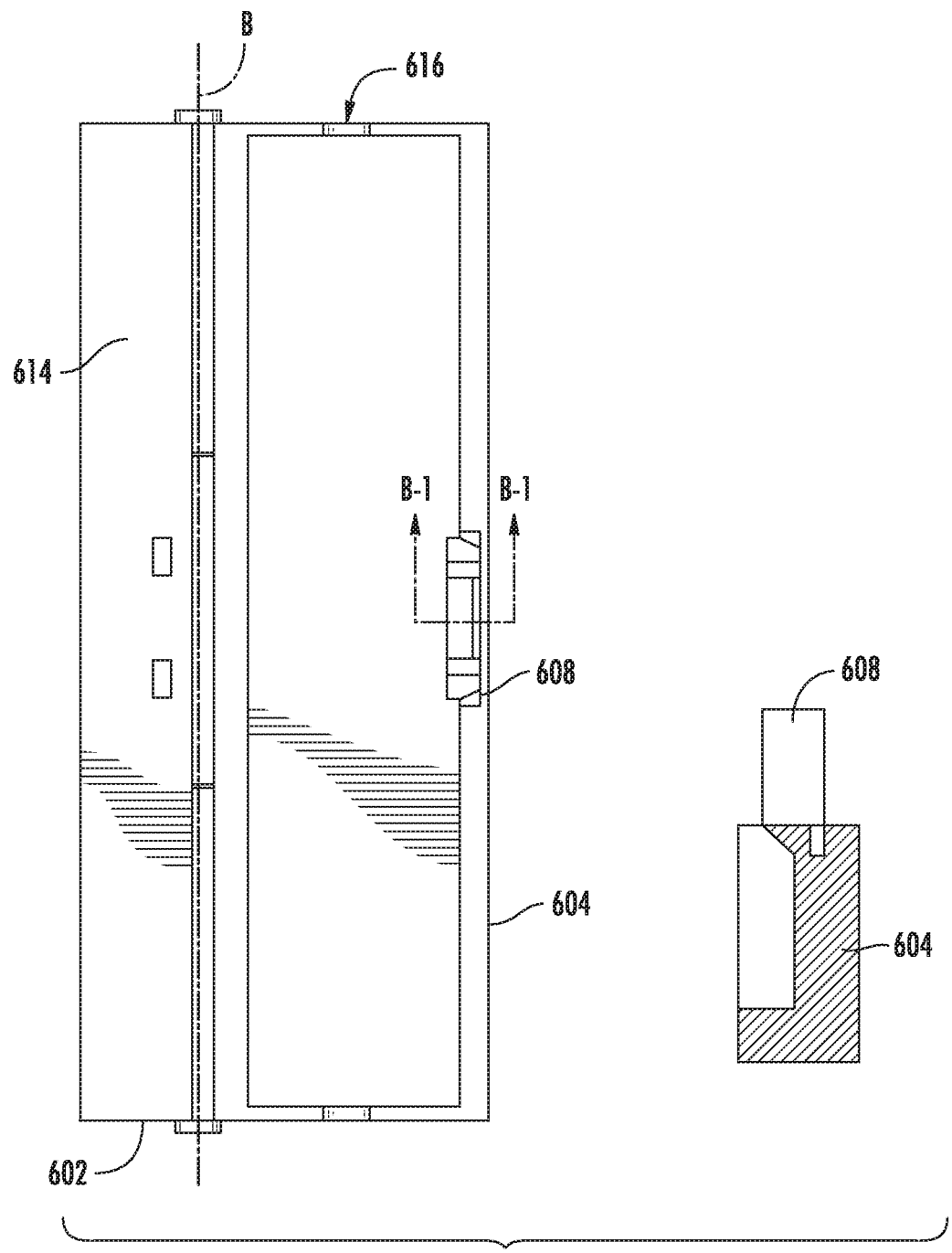
FIG. 6B is a top view including an inset taken along the line B1-B1 illustrating a second embodiment of a clamping box in an unlocked position for a blood vessel line enclosure apparatus according to the presently disclosed subject matter.
Figure 6C:
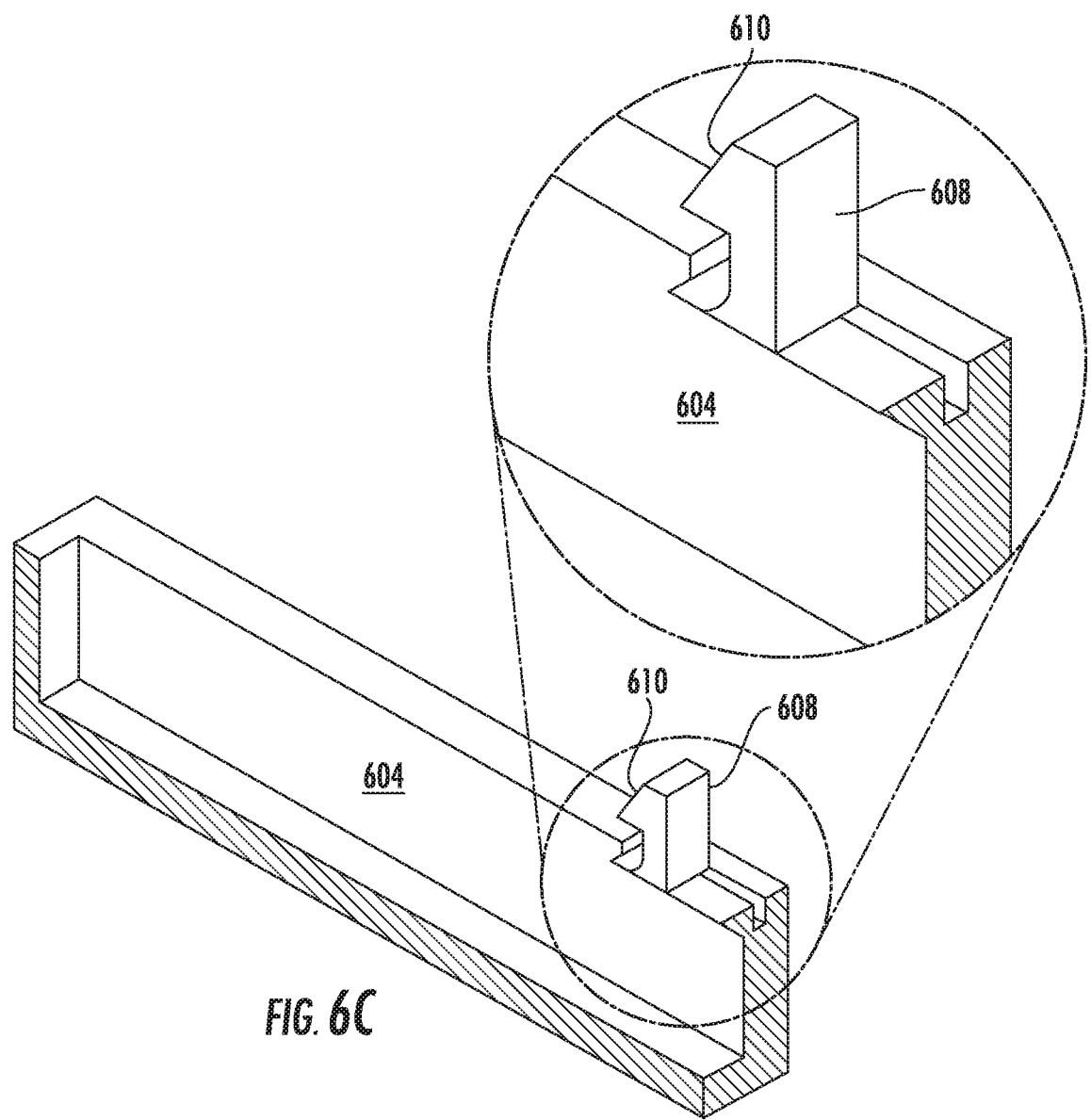
FIG. 6C is a rear perspective cut away view of second part 604 including an enlarged inset illustrating a second embodiment of a clamping box in an unlocked position for a blood vessel line enclosure apparatus according to the presently disclosed subject matter.

In some aspects, a second embodiment of a blood vessel line enclosure apparatus is provided in FIGS. 6A-6C and FIG. 7. Referring now to FIGS. 6A-6C, a clamping box 600 for enclosing at least a portion of a blood vessel line therein is illustrated in various views. Clamping box 600 may comprise a first part 602 and a second part 604 that are attachable to one another. For example, first part 602 and second part 604 are configured to pivot with respect to one another via a pivot axis B defined by longitudinally extending first side edges of both the first part 602 and the second part 604. Notably, however, first part 602 and second part 604 may relate to one another in a manner other than pivoting. For example, a hinge, screw, spring, and/or any other mechanism may allow one or more part of clamping box 600 to move relative to one another in order to enclose the blood vessel line within. Regardless, first part 602 and second part 604 may be manipulated into a locked position and an unlocked position. For example, first part 602 and the second part 604 may pivot along pivot axis B into a first or unlocked position where the first part 602 and the second part 604 are not in direct contact along second longitudinally extending side edges, where the second longitudinally extending side edges are disposed opposite the first longitudinally extending side edges (see, FIGS. 6A-6C). In another example, the first part 602 and the second part 604 may pivot along pivot axis B into a second or locked position where the first part 602 and the second part 604 are in direct contact along the second longitudinally extending side edges (see, FIGS. 8B-8C). In some aspects, clamping box 600 may comprise more or less than first part 602 and second part 604, each of which may be manipulated into locked and/or unlocked positions. For example, clamping box 600 may comprise one part, three parts, four parts, etc.

In some aspects, clamping box 600 may have a substantially rectangular prism shape such that each of first part 602 and second part 604 form a rectangular prism when pivoted into the locked position. Alternately, in some aspects, clamping box 600 may have any geometric shape with some basic functionality allowing clamping box 600 to enclose the blood vessel line within. For example, clamping box 600 may be square, ovular, triangular, etc., and/or the edges of clamping box 600 may be rounded (see, for example, a line enclosure apparatus in accordance with the presently disclosed subject matter as shown in FIGS. 11A-11E, 12A-12F, and 14A-14D), pointed, non-uniform, etc. In other aspects, each box may be manufactured according to the measurements of an extremity of a patient so that the box contours to that extremity. For example, clamping box 600 may be sized and shaped to conform to a patient's arm.

In some aspects, first part 602 and second part 604 are configured to lock relative to one another. A locking mechanism disposed on either one or both of first part 602 and second part 604 may be provided in order to prevent a patient and/or other user from easily gaining entry to the blood vessel line enclosed by clamping box 600. However, the locking mechanism may be weak enough to allow for a patient and/or other user to gain entry, if the patient and/or other user is determined to do so. But the locking mechanism is configured so that if tampering does occur, it is easily and quickly detectable by medical personnel. As illustrated in FIGS. 6A-6C, for example, the locking mechanism on clamping box 600 comprises a hole or recess 612 disposed on the second longitudinally extending side edge of first part 602 and one or more protrusion 608 disposed on the second longitudinally extending side edge of second part 604. One or more protrusion 608 may be substantially aligned with recess 612 disposed on the second longitudinally extending side edge of first part 602. One or more hole 606 disposed on first part 602 may be provided in order to unlock clamping box 600, to be described in more detail below. One or more hole 606 may be disposed on front surface 614 of first part 602 of clamping box 600. In some aspects, for example, one or more hole 606 may be disposed towards a bottom edge of front surface 614 and disposed centrally relative to the bottom edge of front surface 614. One or more hole 606 may comprise an opening sized and/or shaped so that an unlocking mechanism, e.g., unlocking mechanism 700, FIG. 7, may be inserted therethrough. In some aspects, at least a portion of the opening of one or more hole 606 may be aligned with one or more protrusion 608 such that an unlocking mechanism may be configured to manipulate one or more protrusion 608 upon insertion in one or more hole 606.

One or more protrusion 608 (inset in FIG. 6B taken along the line B1-B1) may comprise two protrusions each comprising an edge surface 610, which can be chamfered. Edge surface 610 (see for example FIG. 6A and FIG. 6C, enlarged inset in each Figure) may comprise an angled surface and a planar surface substantially parallel to a second longitudinally extending side edge of second part 604. Edge surface 610 may comprise other geometries, shapes, sizes, and/or positions, such as a curved shape. In some aspects, one or more protrusion 608 may be configured to be manipulated. For example, when first part 602 and second part 604 are pivoted into the locked position, one or more protrusion 608 may be deformed inwardly to fit within the confines of recess 612. In this example, the edge surface 610 of each of one or more protrusion 608 may press outwardly in an opposite direction against a side wall of recess 612.

In some aspects, clamping box 600 may be sized to fit at least a portion of a standard blood vessel line therein. For example, a 4 French or larger or smaller in size lumen (see, FIG. 9A, 902B) of a PICC line may be configured to fit within clamping box 400. In this manner, each of the first part 602 and the second part 604 may be formed as hollow halves in order to receive at least a portion of a blood vessel line therein. In some aspects, either one or both of first part 602 and second part 604 of clamping box 600 comprise blood vessel line openings 616 disposed on opposing side surfaces of clamping box 600. For example, blood vessel line openings 616 may comprise semi-circular openings that may allow the blood vessel line to enter and exit clamping box 600 when the clamping box is in the locked position.

Figure 7:
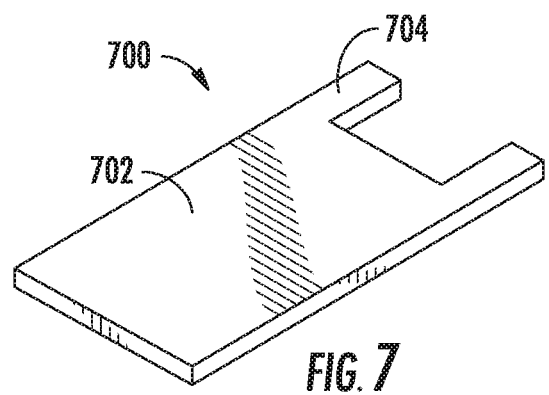
FIG. 7 is a perspective view illustrating a second embodiment of an unlocking mechanism for the clamping box illustrated in FIGS. 6A-6C.

Referring now to FIG. 7, an unlocking mechanism 700 for unlocking clamping box 600 illustrated in FIGS. 6A-6C is illustrated in various views. Unlocking mechanism 700 may comprise a planar surface 702 that may be substantially square in shape for easy gripping and/or handling by medical personnel. Other shapes, sizes, geometries, etc., for providing basic unlocking functionality are contemplated as well. Extending from planar surface 702 is one or more extension 704, which may be sized and/or shaped to comprise teeth (not shown). One or more extension 704 may correspondingly fit within the one or more hole 606 illustrated in FIGS. 6A-6C. For example, in FIG. 7, one or more extension 704 is formed as a rectangular prism. In profile, one or more extension 704 corresponds to a size and shape of one or more hole 606 in FIGS. 6A-6C. Thus, in this example, one or more hole 606 is sized and shaped to receive a corresponding one of the one or more extension 704 upon insertion of unlocking mechanism 700 when clamping box 600 is in a locked position (see FIG. 9C).

Accordingly, in a second embodiment of the blood vessel line enclosure apparatus illustrated in FIGS. 6A-7, to unlock clamping box 600, one or more extension 704 of unlocking mechanism 700 may be inserted into a corresponding one or more hole 606 of clamping box 600 and pressed against edge surface 610 of a corresponding one of one or more protrusion 608. In contrast to the multi-use clamping box, for example, clamping box 400 illustrated in FIGS. 4A-4D, clamping box 600 is a single-use clamping box as one or more protrusion 608 is designed to break rather than elastically deform, from the oblique force exerted by one or more extension 704 of unlocking mechanism 700. More particularly, one or more extension 704 is configured to break one or more protrusion 608 at edge surface 610 so that one or more protrusion 608 is no longer in contact with side edges of recess 612. In this manner, first part 602 and second part 604 of clamping box 600 may be rotated about pivot axis B away from one another and into an unlocked and/or open position. Thus, the second embodiment is a single-use apparatus, as clamping box 600 may be utilized only a single time. Notably, however, a single-use apparatus may be configured in manner different than the clamping box 600 and unlocking mechanism 700 illustrated in FIGS. 6A-7. For example, a single-use apparatus may comprise one or more hole disposed on a top surface or side surfaces, while unlocking mechanism 700 may comprise teeth and/or any additional shapes. In some embodiments, then, a single-use apparatus can provide for the detection of unauthorized unlocking from the locked position by the unauthorized insertion of the unlocking mechanism, such as by a user or other individual who has unauthorizedly obtained or prepared an unlocking mechanism.

In some aspects, clamping box 600 may be 3D printed although other manufacturing techniques such as extruding, injection molding, etc., may be used. As a result, if clamping box 600 is manufactured via injection molding, clamping box 600 may require locking mechanisms other than one or more protrusion 608 and recess 612, and unlocking mechanism 700. More particularly, a clamping box 600 composed of injection molded plastic may comprise material properties that are less brittle than 3D printed plastic, such that, for example, additional perforation(s) other than one or more hole 606, may be necessary to break one or more protrusion 608, when unlocking mechanism 700 is inserted therein.

Moreover, slightly different dimensioning may also be needed. Consequently, different manufacturing techniques of clamping box 600 may require different configurations of clamping box 600 in order to compensate for different material properties used for manufacture.

Figure 8C:
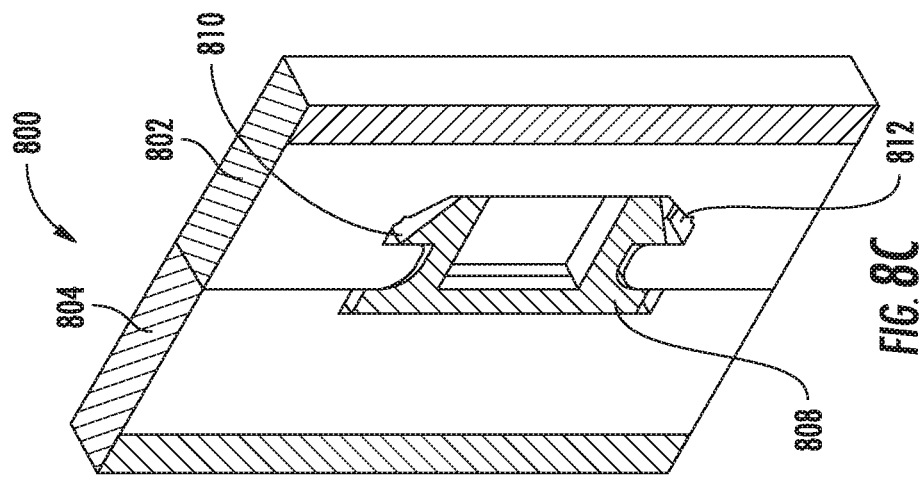
FIG. 8C is a perspective view of the section view of FIG. 8B illustrating the second embodiment of the clamping box illustrated in FIGS. 6A-6C in a locked position.
Figure 8B:
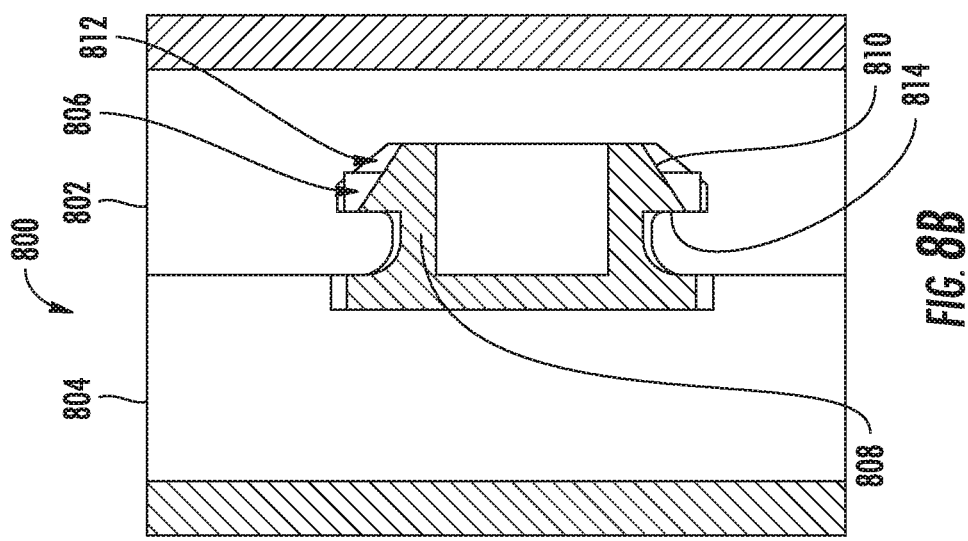
FIG. 8B is a section view along the line 8B-8B in FIG. 8A illustrating the second embodiment of the clamping box illustrated in FIGS. 6A-6C in a locked position.
Figure 8A:
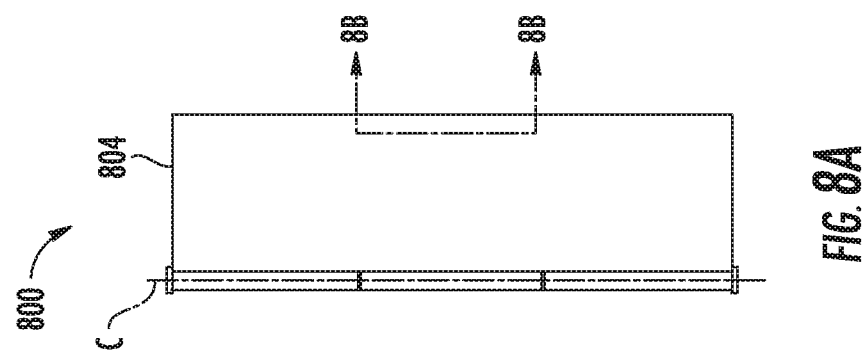
FIG. 8A is a top view illustrating the second embodiment of the clamping box illustrated in FIGS. 6A-6C in a locked position.
Figure 10A:
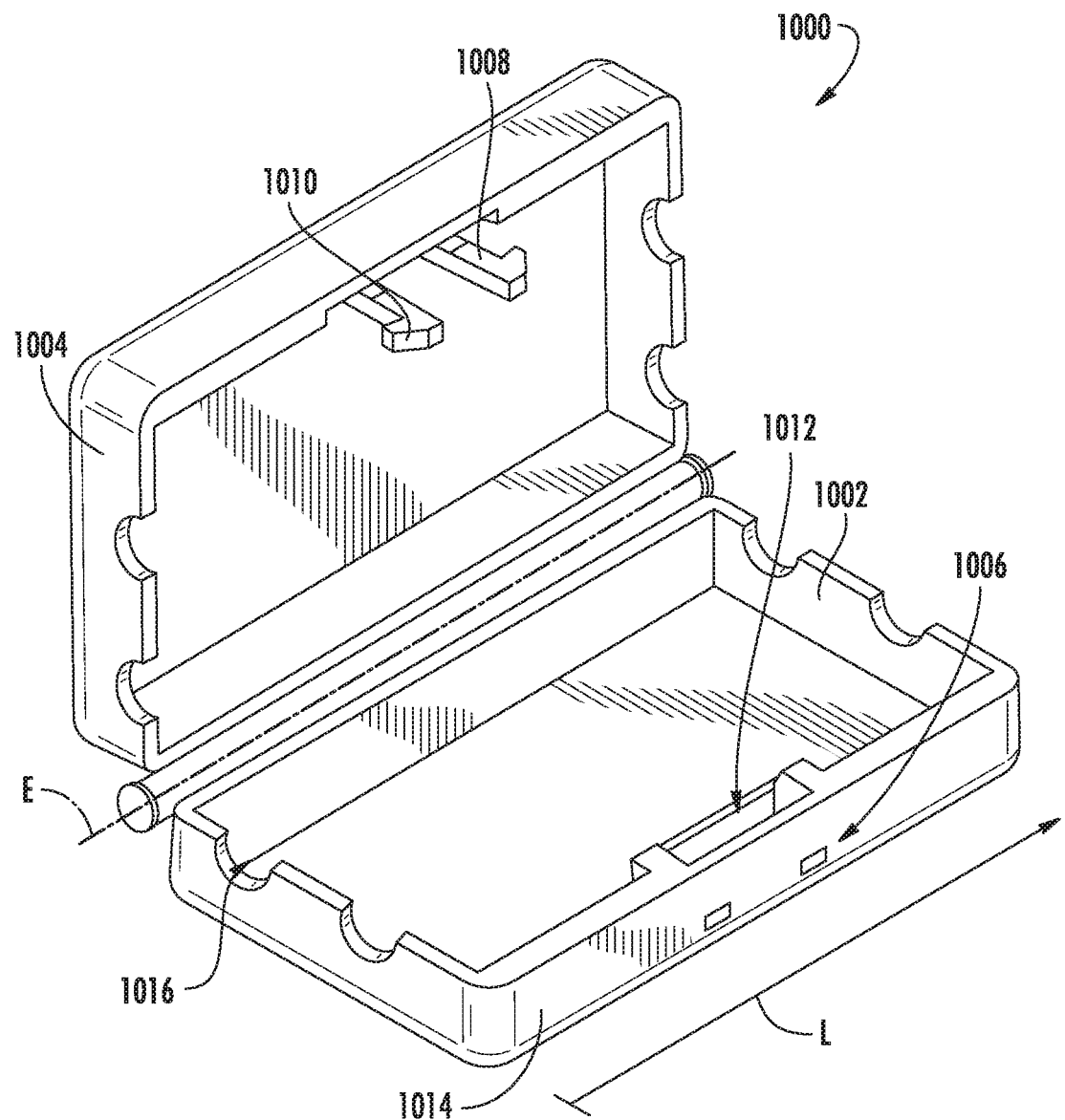
FIG. 10A is a perspective view illustrating a third embodiment of a clamping box in an unlocked position for a blood vessel line or other vessel line enclosure apparatus according to the presently disclosed subject matter.
Figure 10B:
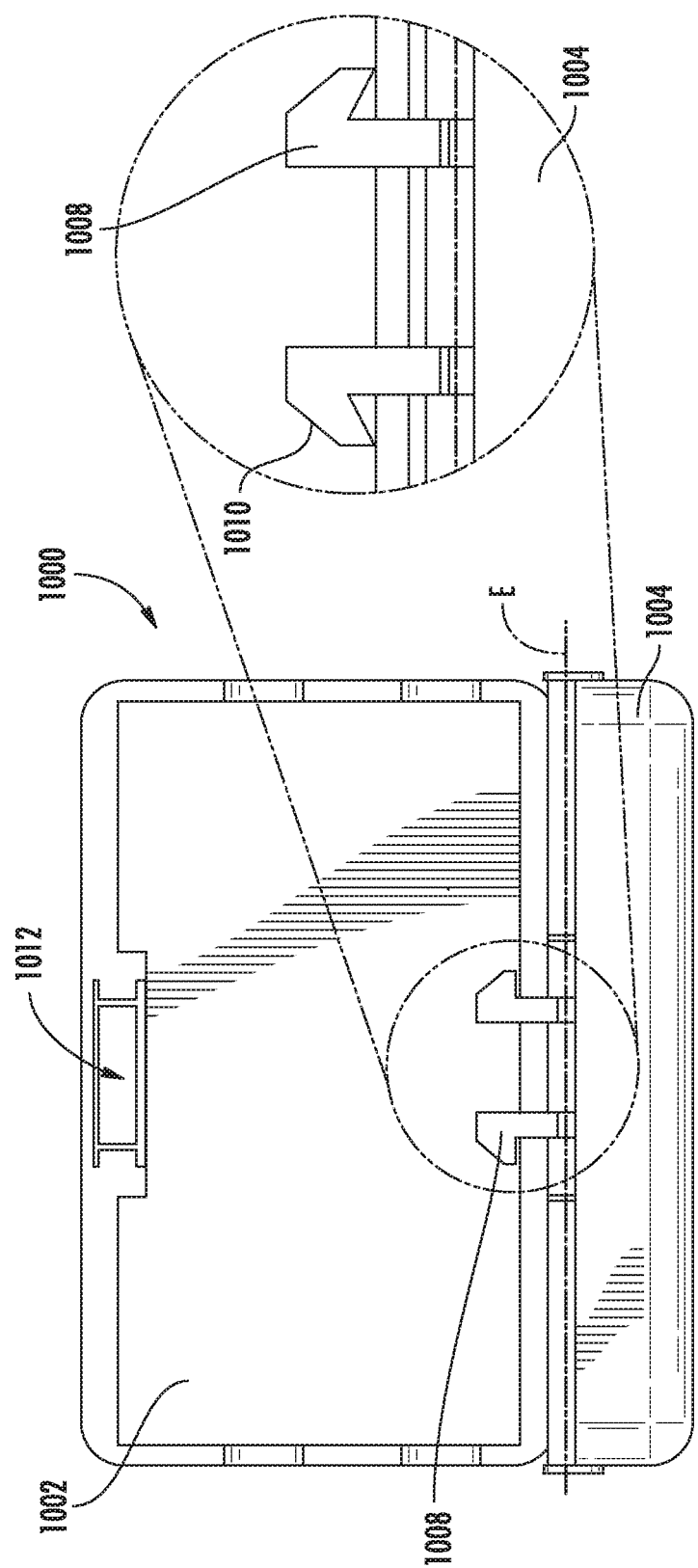
FIG. 10B is a front view with enlarged inset illustrating a third embodiment of a clamping box in an unlocked position for a blood vessel line or other vessel line enclosure apparatus according to the presently disclosed subject matter.
Figure 10C:
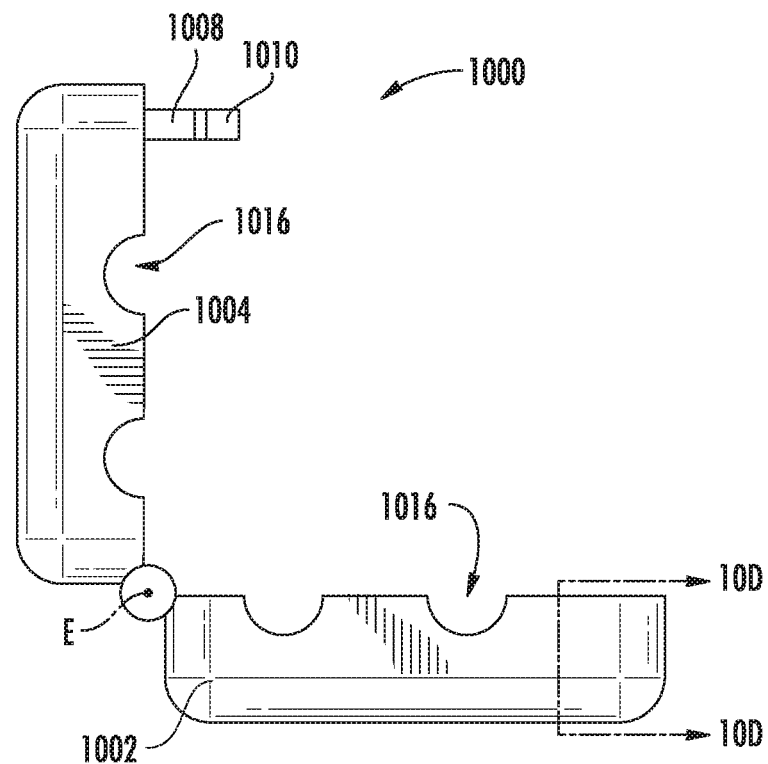
FIG. 10C is a side view illustrating a third embodiment of a clamping box in an unlocked position for a blood vessel line or other vessel line enclosure apparatus according to the presently disclosed subject matter.
Figure 10D:
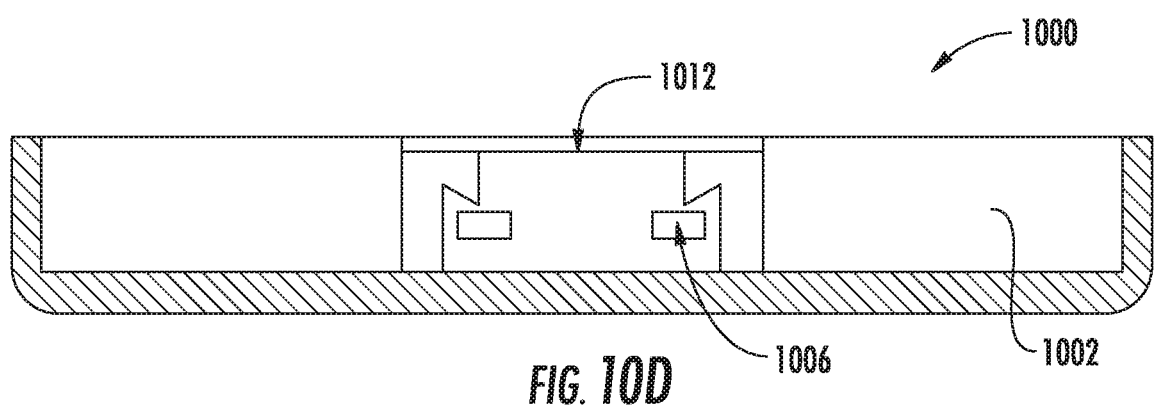
FIG. 10D is a section view along the line 10D-10D in FIG. 10C illustrating a third embodiment of a clamping box in an unlocked position for a blood vessel line or other vessel line enclosure apparatus according to the presently disclosed subject matter.
Figure 10E:
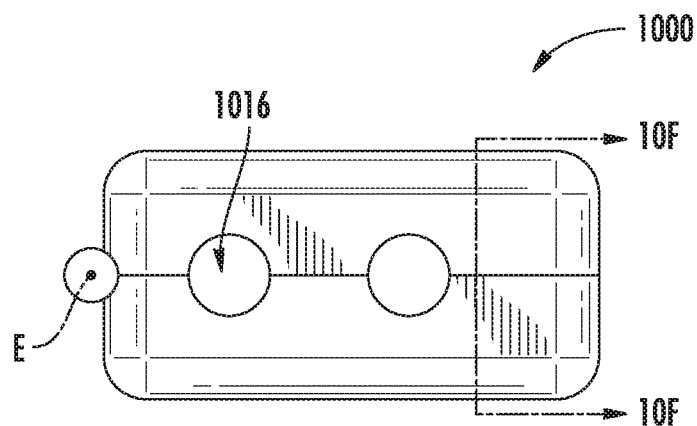
FIG. 10E is a side view illustrating the third embodiment of the clamping box illustrated in FIGS. 10A-10D in a locked position.
Figure 10F:
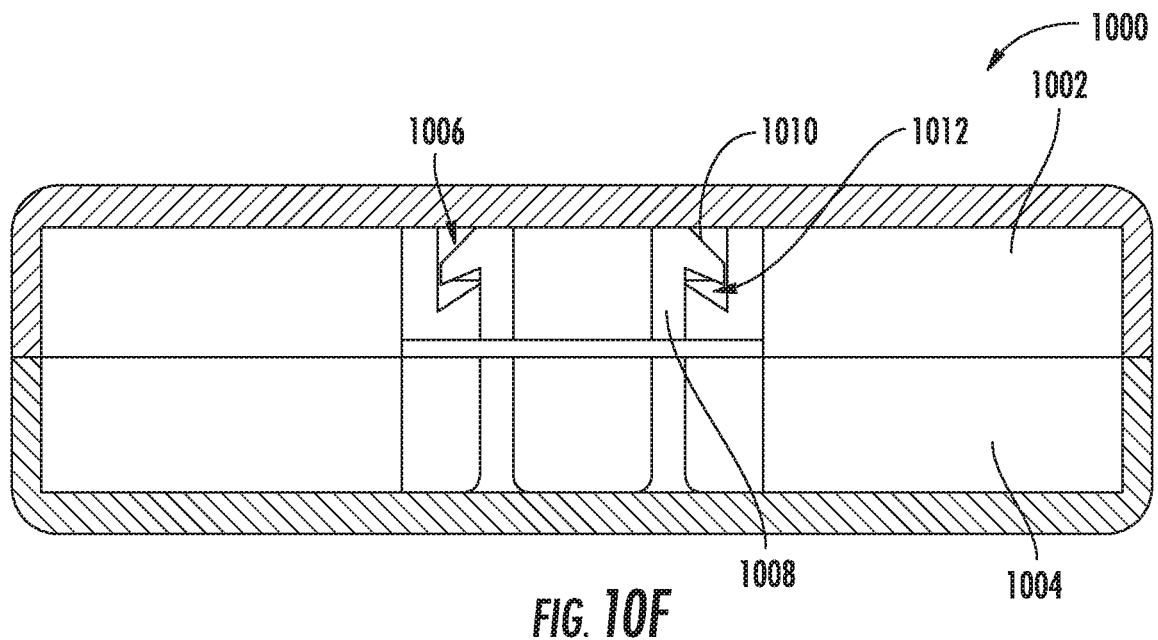
FIG. 10F is a section view along the line 10F-10F in FIG. 10E illustrating the third embodiment of the clamping box illustrated in FIGS. 10A-10D in a locked position.
Figure 11B:
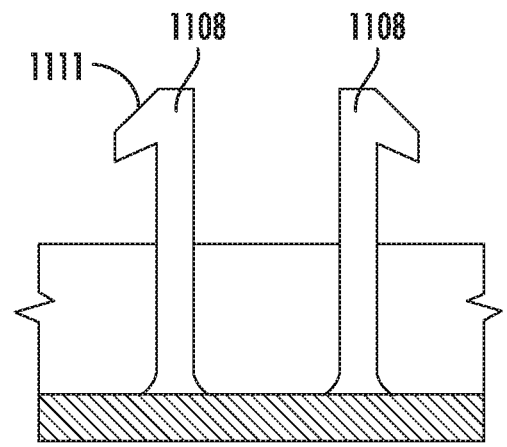
FIG. 11B is a section view taken along the line 11B-11B in FIG. 11A illustrating part 1104 of a fourth embodiment of a line enclosure apparatus according to the presently disclosed subject matter.
Figure 11C:
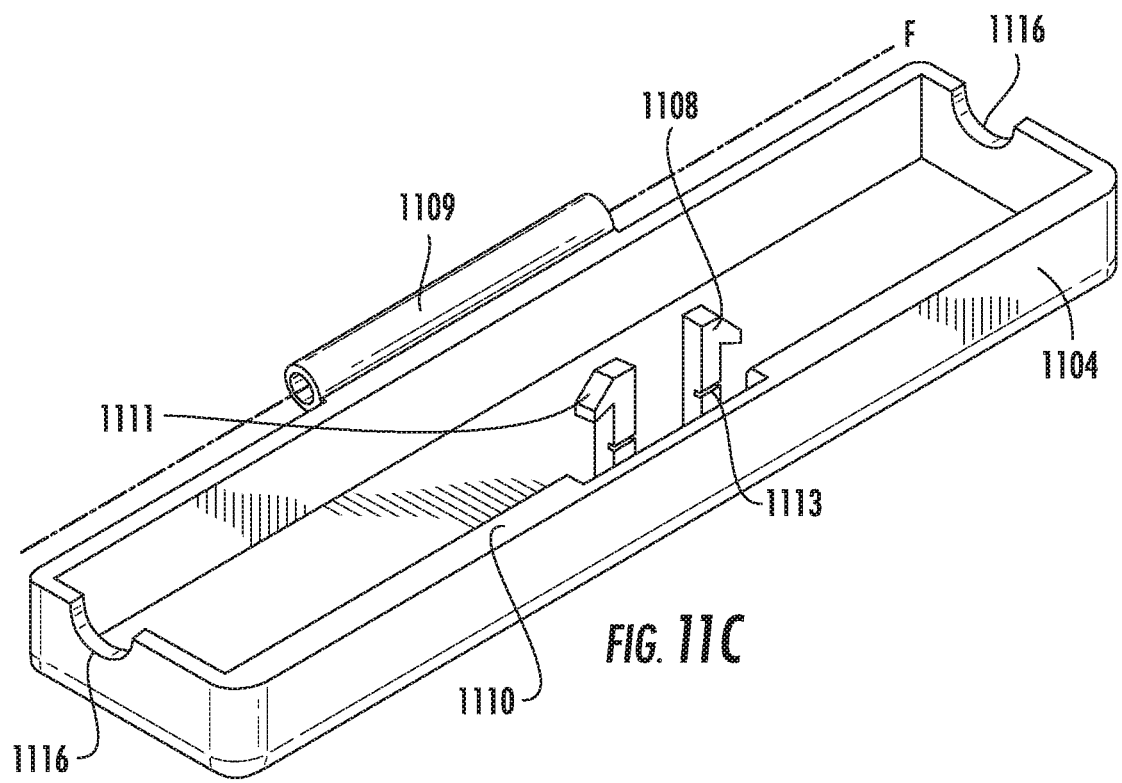
FIG. 11C is a perspective view illustrating part 1104 of a fourth embodiment of a line enclosure apparatus according to the presently disclosed subject matter.
Figure 11D:
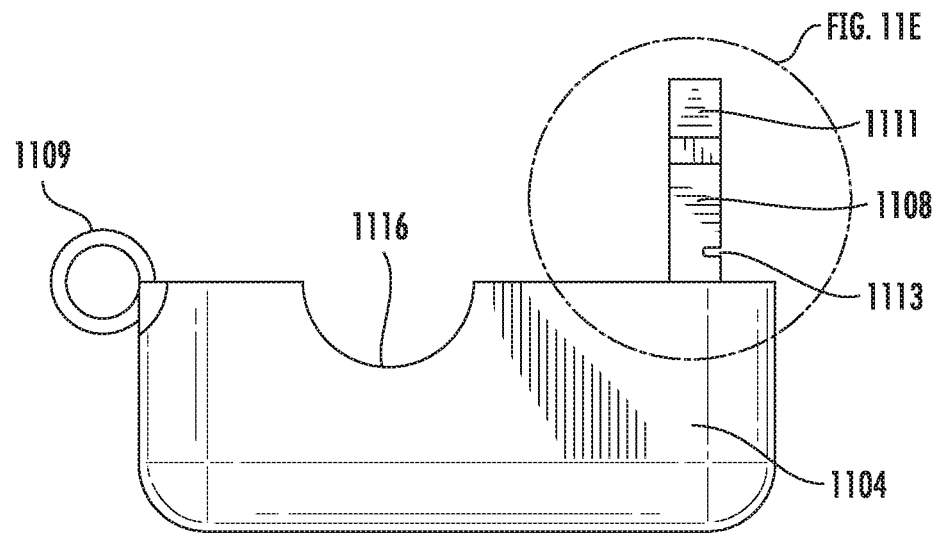
FIG. 11D is a side view illustrating part 1104 of a fourth embodiment of a line enclosure apparatus according to the presently disclosed subject matter.
Figure 11E:
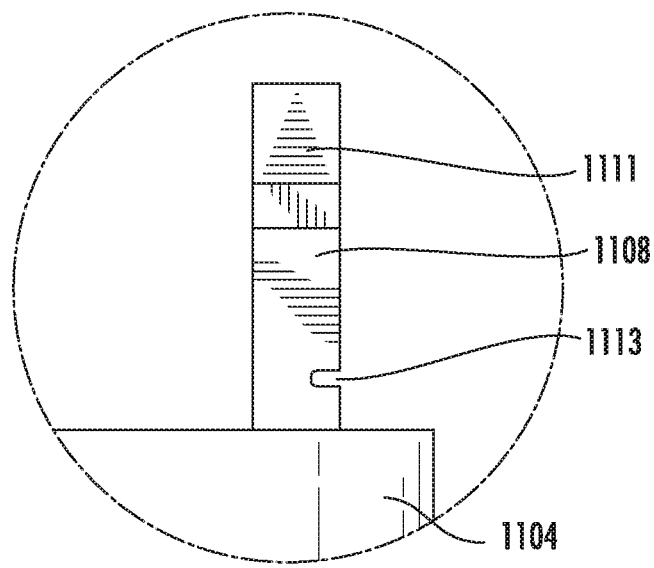
FIG. 11E is an enlarged view from circle in FIG. 11D showing a side view of protrusion 1108 of a fourth embodiment of a line enclosure apparatus according to the presently disclosed subject matter.
Figure 12E:
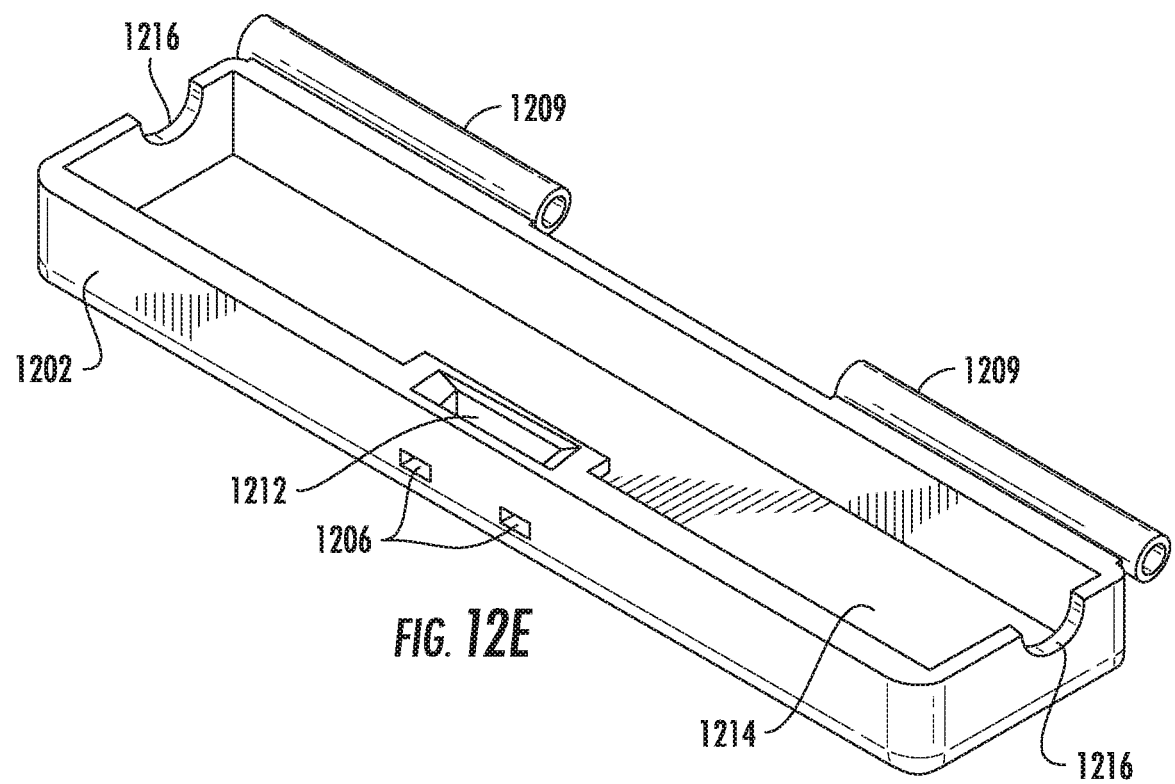
FIG. 12E is a perspective view illustrating part 1202 of a fourth embodiment of a line enclosure apparatus according to the presently disclosed subject matter.
Figure 12F:
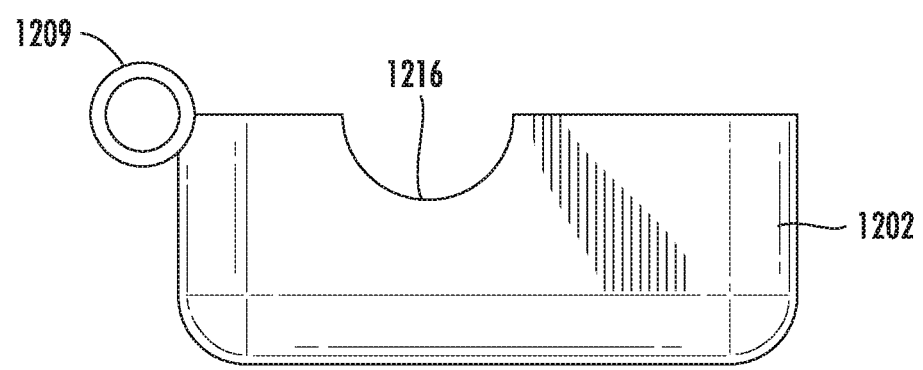
FIG. 12F is a side view illustrating part 1202 of a fourth embodiment of a line enclosure apparatus according to the presently disclosed subject matter.

Referring now to FIGS. 8A-8C, various views illustrating an embodiment of a clamping box, generally designated 800, in a locked position are illustrated. In some aspects, FIGS. 8A-8C provide additional views of the second embodiment of the clamping box illustrated in FIGS. 6A-6C or a single-use apparatus where one or more hole is not provided on a top surface of the clamping box. Similar to clamping box 600, clamping box 800 may comprise a first part 802 and a second part 804 that are configured to pivot with respect to one another via a pivot axis C, see FIG. 8A.

As illustrated in FIGS. 8B-8C, in the locked position, first part 802 and second part 804 are in direct contact along the second longitudinally extending side edges. In the locked position, one or more protrusion 808 disposed on second part 804 is deformed inwardly to fit within the confines of a hole or recess 812 disposed on first part 802, while a hole 806 is disposed on a front surface of first part 802 to provide access for an unlocking mechanism (e.g., unlocking mechanism 700, FIG. 7) to one or more protrusion 808. Recess 812 may comprise a non-uniform cross-section. More particularly, recess 812 may comprise a cross-section configured to enable one or more protrusion 808 to deform inwardly as one or more protrusion 808 is pressed into the locked position within recess 812. For example, recess 812 may comprise at least one shoulder 814 configured to prevent movement of one or more protrusion 808 out of recess 812 once edge surface 810, which can be chamfered, of each of one or more protrusion 808 has deformed past shoulder 814 into recess 812.

In some aspects, in the locked position, at least a portion of edge surface 810 of each of one or more protrusion 808 is aligned with an opening of one or more hole 806, such that an unlocking mechanism may be configured to enter through the opening of one or more hole 806 in first part 802 and manipulate one or more protrusion 808. Specifically, one or more protrusion 808 is designed such that oblique force from an unlocking mechanism entering through the opening of one or more hole 806 in first part 802 may cause edge surface 810 of each of one or more protrusion 808 to break rather than elastically deform. By breaking edge surface 810 from each of one or more protrusion 808, one or more protrusion is no longer prevented from exiting recess 812. In this manner, first part 802 and second part 804 of clamping box 800 may be rotated about pivot axis C away from one another and into an unlocked and/or open position, as one or more protrusion may slide out of recess 812.

Referring now to FIGS. 9A-9D, a method for using a blood vessel line enclosure system, generally designated 900, enclosing a blood vessel line 902A having a lumen 9026 is illustrated. In some aspects, system 900 comprises a clamping box 904 configured to enclose lumen 9026 and at least a portion of blood vessel line 902A. In some aspects, FIGS. 9A-9D illustrate the first embodiment of the clamping box and unlocking mechanism illustrated in FIGS. 5A-5D and FIGS. 6A-6B, respectively, or a multi-use apparatus where one or more hole is provided on a top surface of the clamping box.

In FIG. 9A, clamping box 904 is illustrated in an unlocked or open position. In an unlocked position, similar to clamping box 400 in FIGS. 4A-4D, clamping box 904 comprises a first part 906 and a second part 908 that are configured to pivot with respect to one another via a pivot axis D. Clamping box 904 comprises one or more hole 910 disposed on a top surface 916 of first part 906 and one or more protrusion 912 disposed on second part 908. In some aspects, either one or both of first part 906 and second part 908 of clamping box 904 comprise blood vessel line openings 918 disposed on opposing side surfaces of clamping box 904.

In the unlocked position illustrated in FIG. 9A, a hole or recess 914 disposed on first part 906 of clamping box 904 and one or more protrusion 912 disposed on second part 908 of clamping box 904 are not engaged. At least a portion of blood vessel line 902A between a first end inserted into a patient and/or a second end connected to a supply of fluid is positioned in clamping box 904. For example, lumen 902B is positioned in second part 908 of clamping box 904.

FIG. 9B illustrates clamping box 904 in a locked position, where one or both of first part 906 and second part 908 of clamping box 904 may be pivoted such that one or more protrusion 912 disposed on second part 908 is configured to be substantially locked within recess 914 disposed on first part 906.

FIG. 9C illustrates an unlocking mechanism, generally designed 920, being inserted in one or more hole 910 disposed on top surface 916 of first part 906 of clamping box 904 in order to unlock the clamping box when first part 906 and second part 908 of clamping box 904 are in the locked position. Unlocking mechanism 920 may be similar to unlocking mechanism 500 illustrated in FIGS. 5A-5B. Unlocking mechanism 920 may comprise one or more extension 922 that is shaped to include teeth (see, 924, FIG. 9D). When one or more extension 922 is inserted into one or more hole 910, one or more extension 922 may press against a corresponding one or more protrusion 912 in order to elastically deform one or more protrusion 912 inwardly and away from recess 914. In this way, as illustrated in FIG. 9C, clamping box 904 may be unlocked and first part 906 and second part 908 may be pivoted away from one another about pivot axis D.

As illustrated in FIG. 9D, teeth 924 may comprise a rectangular prism shape such that an overall cross-section of one or more extension 922 and teeth 924 form a "T" shape. However, cross-sections of varying shapes and sizes for one or more extension 922 and teeth 924 are contemplated herein.

Continuing with reference to FIGS. 9A-9D, system 900 may include a sticker 950 configured to be applied onto a surface of first part 906 and second part 908 of clamping box 904 and over at least a seam formed at the surfaces of first part 906 and second part 908 of clamping box 904 when clamping box 904 is in a closed or locked position. In some aspects, the surface may be a front surface of the clamping box 904. Advantageously, sticker 950 may provide secondary verification of tampering. For example, if sticker 950 has been broken (see e.g., sticker parts 950*a* and 950*b* in FIGS. 9C and 9D), medical personnel may be able to quickly detect that tampering of the blood vessel enclosure has occurred.

In some aspects, a third embodiment of a blood vessel line enclosure apparatus is provided in FIGS. 10A-10F. Referring now to FIGS. 10A-10F, a clamping box 1000 for enclosing at least a portion of a blood vessel line therein is illustrated in various views. Specifically, clamping box 1000 is configured to enclose at least a portion of two or more blood vessel lines therein, although clamping box 1000 may be configured to enclose only one blood vessel line or more than two blood vessel lines (e.g., three, four, etc.,). In this manner, the third embodiment of the enclosure apparatus may differ from the second embodiment of the enclosure apparatus only in that the third embodiment is configured to enclose more than one blood vessel line therein.

Clamping box 1000 may comprise a first part 1002 and a second part 1004 that are attachable to one another. For example, first part 1002 and second part 1004 are configured to pivot with respect to one another via a pivot axis E defined by longitudinally extending first side edges of both the first part 1002 and the second part 1004. Notably, however, first part 1002 and second part 1004 may relate to one another in a manner other than pivoting. For example, a hinge, screw, spring, and/or any other mechanism may allow one or more part of clamping box 1000 to move relative to one another in order to enclose the blood vessel line within. Regardless, first part 1002 and second part 1004 may be manipulated into a locked position and an unlocked position. For example, first part 1002 and the second part 1004 may pivot along pivot axis E into a first or unlocked position where the first part 1002 and the second part 1004 are not in direct contact along second longitudinally extending side edges, where the second longitudinally extending side edges are disposed opposite the first longitudinally extending side edges (see, FIGS. 10A-10C). In another example, the first part 1002 and the second part 1004 may pivot along pivot axis E into a second or locked position where the first part 1002 and the second part 1004 are in direct contact along the second longitudinally extending side edges (see, FIGS. 10E-10F). In some aspects, clamping box 1000 may comprise more parts than first part 1002 and second part 1004. For example, clamping box 1000 may be composed of one part, three parts, four parts, etc., each of which may be manipulated into locked and/or unlocked positions. In some aspects, these parts may relate to one another in a manner other than pivoting.

In some aspects, clamping box 1000 may have a substantially rectangular prism shape such that each of first part 1002 and second part 1004 form a rectangular prism when pivoted into the locked position. Alternately, in some aspects, clamping box 1000 may have any geometric shape with some basic functionality allowing clamping box 1000 to enclose the blood vessel line within. For example, clamping box 1000 may be square, ovular, triangular, etc., and/or the edges of clamping box 1000 may be rounded (see, for example, a line enclosure apparatus in accordance with the presently disclosed subject matter as shown in FIGS. 11A-11E, 12A-12F, and 14A-14D), pointed, non-uniform, etc. As illustrated in FIGS. 10A-10F, for example, clamping box 1000 comprises a rectangular prism shape with rounded edges for patient comfort. In other aspects, each box may be manufactured according to the measurements of an extremity of a patient so that the box contours to that extremity. For example, clamping box 1000 may be sized and shaped to conform to a patient's arm.

In some aspects, first part 1002 and second part 1004 are configured to lock relative to one another. A locking mechanism disposed on either one or both of first part 1002 and second part 1004 may be provided in order to prevent a patient and/or other user from easily gaining entry to the blood vessel line enclosed by clamping box 1000. However, the locking mechanism may be weak enough to allow for a patient and/or other user to gain entry, if the patient and/or other user is determined to do so. But the locking mechanism is configured so that if tampering does occur, it is easily and quickly detectable by medical personnel. As illustrated in FIGS. 10A-10F for example, the locking mechanism on clamping box 1000 comprises a hole or recess 1012 disposed on the second longitudinally extending side edge of first part 1002 and one or more protrusion 1008 disposed on the second longitudinally extending side edge of second part 1004. One or more protrusion 1008 may be substantially aligned with recess 1012 disposed on the second longitudinally extending side edge of first part 1002. One or more hole 1006 disposed on first part 1002 may be provided in order to unlock clamping box 1000, to be described in more detail below.

One or more hole 1006 may be disposed on front surface 1014 of first part 1002 of clamping box 1000. In some aspects, for example, one or more hole 1006 may be disposed towards a bottom edge of front surface 1014 and disposed centrally relative to the bottom edge of front surface 1014. One or more hole 1006 may comprise an opening sized and/or shaped so that an unlocking mechanism, e.g., unlocking mechanism 700, FIG. 7, may be inserted therethrough. In some aspects, at least a portion of the opening of one or more hole 1006 may be aligned with one or more protrusion 1008 such that an unlocking mechanism may be configured to manipulate one or more protrusion 1008 upon insertion in one or more hole 1006.

One or more protrusion 1008 may comprise two protrusions each comprising an edge surface 1010 (see for example, the enlarged view in FIG. 10B), which can be a chamfered edge. Edge surface 1010 may comprise an angled surface and a planar surface substantially parallel to a second longitudinally extending side edge of second part 1004. Edge surface 1010 may comprise other geometries, shapes, sizes, and/or positions, such as a curved shape. In some aspects, one or more protrusion 1008 may be configured to be manipulated. For example, when first part 1002 and second part 1004 are pivoted into the locked position, one or more protrusion 1008 may be deformed inwardly to fit within the confines of recess 1012. In this example, the edge surface 1010 of each of one or more protrusion 1008 may press outwardly in an opposite direction against a side wall of recess 1012.

In some aspects, clamping box 1000 may be sized to fit least a portion of two or more blood vessel lines therein. For example, two 4 French or larger or smaller in size lumens (see, FIG. 9A, 902B) of PICC lines may be configured to fit lengthwise within clamping box 1000 along a longitudinal or length direction L (see FIG. 10A) of clamping box 1000. Alternately, clamping box 1000 may be configured to enclose more than two lumens within, such as for example, three lumens, four lumens, etc. In this manner, each of the first part 1002 and the second part 1004 may be formed as hollow portions in order to receive at least a portion of two or more blood vessel lines therein. In some aspects, either one or both of first part 1002 and second part 1004 of clamping box 1000 comprise blood vessel line openings 1016 disposed on opposing side surfaces of clamping box 1000. For example, blood vessel line openings 1016 may comprise two semi-circular openings on each opposing side surface of clamping box 1000 that may allow the blood vessel lines to enter and exit clamping box 1000 when the clamping box is in the locked position.

Accordingly, in the third embodiment of the blood vessel line enclosure apparatus illustrated in FIGS. 10A-10F, to unlock clamping box 1000, a unlocking mechanism (e.g., 700, FIG. 7) may be inserted into a corresponding one or more hole 1006 of clamping box 1000 and pressed against edge surface 1010 of a corresponding one of one or more protrusion 1008. In contrast to the multi-use clamping box, for example, clamping box 400 illustrated in FIGS. 4A-4D, clamping box 1000 is a single-use clamping box as one or more protrusion 1008 is designed to break rather than elastically deform, from the oblique force exerted by the unlocking mechanism. More particularly, the unlocking mechanism is configured to break one or more protrusion 1008 at edge surface 1010 so that one or more protrusion 1008 is no longer in contact with side edges of recess 1012. In this manner, first part 1002 and second part 1004 of clamping box 1000 may be rotated about pivot axis E away from one another and into an unlocked and/or open position. Thus, the third embodiment is a single-use apparatus, as clamping box 1000 may be utilized only a single time. Notably, however, a single-use apparatus may be configured in manner different than the clamping box 1000 illustrated in FIGS. 10A-10F. For example, a single-use apparatus may comprise one or more hole disposed on a top surface or side surfaces. In some embodiments, then, a single-use apparatus can provide for the detection of unauthorized unlocking from the locked position by the unauthorized insertion of the unlocking mechanism, such as by a user or other individual who has unauthorizedly obtained or prepared an unlocking mechanism.

In some aspects, clamping box 1000 may be 3D printed although other manufacturing techniques such as extruding, injection molding, etc., may be used. As a result, if clamping box 1000 is manufactured via injection molding, clamping box 1000 may require locking mechanisms other than one or more protrusion 1008 and recess 1012, and unlocking mechanism (e.g., unlocking mechanism 700, FIG. 7). More particularly, a clamping box 1000 composed of injection molded plastic may comprise material properties that are less brittle than 3D printed plastic, such that, for example, additional perforation(s) other than one or more hole 1006, may be necessary to break one or more protrusion 1008, when an unlocking mechanism is inserted therein. Moreover, slightly different dimensioning may also be needed. Consequently, different manufacturing techniques of clamping box 1000 may require different configurations of clamping box 1000 in order to compensate for different material properties used for manufacture.

In some aspects, a fourth embodiment of a blood vessel line enclosure apparatus is provided in FIGS. 11A-11E, 12A-12F, 13A-13C, and 14A-14D. Clamping box 1400 may be square, ovular, triangular, etc., and/or the edges and/or corners of clamping box 1400 may be rounded, pointed, non-uniform, etc. Referring now to 11A-11E, 12A-12F, and 14A-14D, a clamping box 1400 for enclosing at least a portion of a blood vessel line therein is illustrated in various views. Specifically, clamping box 1400 is configured to enclose at least a portion of one or more blood vessel lines therein, although clamping box 1400 may be configured to enclose two or more blood vessel lines (e.g., two, three, four, etc.,).

Clamping box 1400 may comprise a first part 1202 and a second part 1104 that are attachable to one another. For example, first part 1202 and second part 1104 are configured to pivot with respect to one another via a pivot axis F defined by longitudinally extending first side edges of both the first part 1202 and the second part 1104. Notably, however, first part 1202 and second part 1104 may relate to one another in a manner other than pivoting. For example, a hinge, screw, spring, and/or any other mechanism may allow one or more part of clamping box 1400 to move relative to one another in order to enclose the blood vessel line within. Regardless, first part 1202 and second part 1104 may be manipulated into a locked position and an unlocked position. For example, first part 1202 and the second part 1104 may pivot on hinges 1109, 1209 and hinge pin 1330 along pivot axis F into a first or unlocked position where the first part 1202 and the second part 1104 are not in direct contact along second longitudinally extending side edges, where the second longitudinally extending side edges are disposed opposite the first longitudinally extending side edges (see, FIGS. 14A-14D). In another example, the first part 1202 and the second part 1104 may pivot on hinges 1109, 1209 and hinge pin 1330 along pivot axis F into a second or locked position where the first part 1202 and the second part 1104 are in direct contact along the second longitudinally extending side edges. In some aspects, clamping box 1400 may comprise more parts than first part 1202 and second part 1104. For example, clamping box 1400 can comprise one part, three parts, four parts, etc., each of which may be manipulated into locked and/or unlocked positions. In some aspects, these parts may relate to one another in a manner other than pivoting.

In some aspects, clamping box 1400 may have a substantially rectangular prism shape such that each of first part 1202 and second part 1104 form a rectangular prism when pivoted into the locked position. Alternately, in some aspects, clamping box 1400 may have any geometric shape with some basic functionality allowing clamping box 1400 to enclose the blood vessel line within. As illustrated in FIGS. 11A-11E, 12A-12F, 13A-13C, and 14A-14D, for example, clamping box 1400 comprises a rectangular prism shape with rounded edges for patient comfort. In other aspects, each box may be manufactured according to the measurements of an extremity of a patient so that the box contours to that extremity. For example, clamping box 1400 may be sized and shaped to conform to a patient's arm.

In some aspects, first part 1202 and second part 1104 are configured to lock relative to one another. A locking mechanism disposed on either one or both of first part 1202 and second part 1104 may be provided in order to prevent a patient and/or other user from easily gaining entry to the blood vessel line enclosed by clamping box 1400. However, the locking mechanism may be weak enough to allow for a patient and/or other user to gain entry, if the patient and/or other user is determined to do so. But the locking mechanism is configured so that if tampering does occur, it is easily and quickly detectable by medical personnel. As illustrated in FIGS. 11A-11E, 12A-12F, 13A-13C, and 14A-14D, for example, the locking mechanism on clamping box 1400 comprises a hole or recess 1212 disposed on the second longitudinally extending side edge of first part 1202 and one or more protrusion 1108 disposed on the second longitudinally extending side edge of second part 1104. One or more protrusion 1108 may be substantially aligned with recess 1212 disposed on the second longitudinally extending side edge of first part 1202. One or more hole 1206 disposed on first part 1202 may be provided in order to unlock clamping box 1400, to be described in more detail below.

One or more hole 1206 may be disposed on front surface 1214 of first part 1202 of clamping box 1400. In some aspects, for example, one or more hole 1206 may be disposed towards a bottom edge of front surface 1214 and disposed centrally relative to the bottom edge of front surface 1214. One or more hole 1206 may comprise an opening sized and/or shaped so that an unlocking mechanism, e.g., unlocking mechanism 1500, FIGS. 15A-15C, may be inserted therethrough. In some aspects, at least a portion of the opening of one or more hole 1206 may be aligned with one or more protrusion 1108 such that an unlocking mechanism may be configured to manipulate one or more protrusion 1108 upon insertion in one or more hole 1206.

One or more protrusion 1108 may comprise two protrusions each comprising an edge surface 1111 (see for example, the enlarged view in FIG. 11E), which can be a chamfered edge. Edge surface 1111 may comprise an angled surface and a planar surface substantially parallel to a second longitudinally extending side edge of second part 1104. Edge surface 1111 may comprise other geometries, shapes, sizes, and/or positions, such as a curved shape. In some aspects, one or more protrusion 1108 may be configured to be manipulated. For example, when first part 1202 and second part 1104 are pivoted into the locked position, one or more protrusion 1108 may be deformed inwardly to fit within the confines of recess 1212. In this example, the edge surface 1111 of each of one or more protrusion 1108 may press outwardly in an opposite direction against a side wall of recess 1212.

In some aspects, clamping box 1400 may be sized to fit least a portion of two or more blood vessel lines therein. For example, two 4 French or larger or smaller in size lumens (see, FIG. 9A, 902B) of PICC lines may be configured to fit lengthwise within clamping box 1400 along a longitudinal or length direction of clamping box 1400. Alternately, clamping box 1400 may be configured to enclose more than two lumens within, such as for example, three lumens, four lumens, etc. In this manner, each of the first part 1202 and the second part 1104 may be formed as hollow portions in order to receive at least a portion of two or more blood vessel lines therein. In some aspects, either one or both of first part 1202 and second part 1104 of clamping box 1400 comprise blood vessel line openings 1116, 1216 disposed on opposing side surfaces of clamping box 1400. For example, blood vessel line openings 1116, 1216 may comprise two semi-circular openings on each opposing side surface of clamping box 1400 that may allow the blood vessel lines to enter and exit clamping box 1400 when the clamping box is in the locked position.

Accordingly, in the fourth embodiment of the blood vessel line enclosure apparatus illustrated in FIGS. 11A-11E, 12A-12F, 13A-13C, and 14A-14D, to unlock clamping box 1400, a unlocking mechanism (e.g., 1500, FIGS. 15A-15C) may be inserted into a corresponding one or more hole 1206 of clamping box 1400 and pressed against edge surface 1111 of a corresponding one of one or more protrusion 1108. In contrast to the multi-use clamping box, for example, clamping box 400 illustrated in FIGS. 4A-4D, clamping box 1400 is a single-use clamping box as one or more protrusion 1108 is designed to break rather than elastically deform, from the oblique force exerted by the unlocking mechanism. More particularly, the unlocking mechanism is configured to break one or more protrusion 1108 at scoring marks 1113 so that one or more protrusion 1108 is no longer in contact with side edges of recess 1212. In this manner, first part 1202 and second part 1104 of clamping box 1400 may be rotated about pivot axis F away from one another and into an unlocked and/or open position. Thus, the fourth embodiment is a single-use apparatus, as clamping box 1400 may be utilized only a single time. Notably, however, a single-use apparatus may be configured in manner different than the clamping box 1400 illustrated in FIGS. 11A-11E, 12A-12F, 13A-13C, and 14A-14D. For example, a single-use apparatus may comprise one or more hole disposed on a top surface or side surfaces. In some embodiments, then, a single-use apparatus can provide for the detection of unauthorized unlocking from the locked position by the unauthorized insertion of the unlocking mechanism, such as by a user or other individual who has unauthorizedly obtained or prepared an unlocking mechanism.

In some aspects, clamping box 1400 may be 3D printed although other manufacturing techniques such as extruding, injection molding, etc., may be used. As a result, if clamping box 1400 is manufactured via injection molding, clamping box 1400 may require locking mechanisms other than one or more protrusion 1108 and recess 1212, and unlocking mechanism (e.g., unlocking mechanism 1500, FIGS. 15A-15C). More particularly, a clamping box 1400 composed of injection molded plastic may comprise material properties that are less brittle than 3D printed plastic, such that, for example, additional perforation(s) other than one or more hole 1206, may be necessary to break one or more protrusion 1108, when an unlocking mechanism is inserted therein. Moreover, slightly different dimensioning may also be needed. Consequently, different manufacturing techniques of clamping box 1400 may require different configurations of clamping box 1400 in order to compensate for different material properties used for manufacture.

Figure 13A:
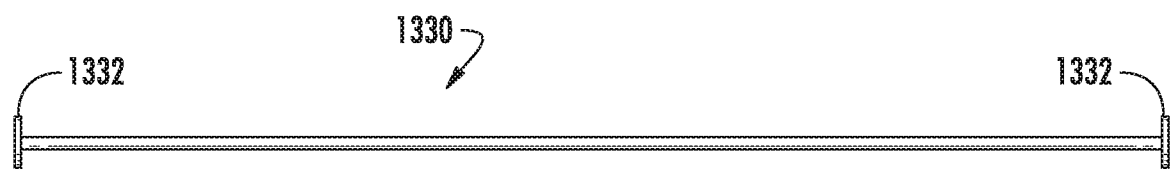
FIG. 13A is a front view illustrating a pin 1330 for use with a pivot axis of a line enclosure apparatus according to the presently disclosed subject matter.
Figure 13B:
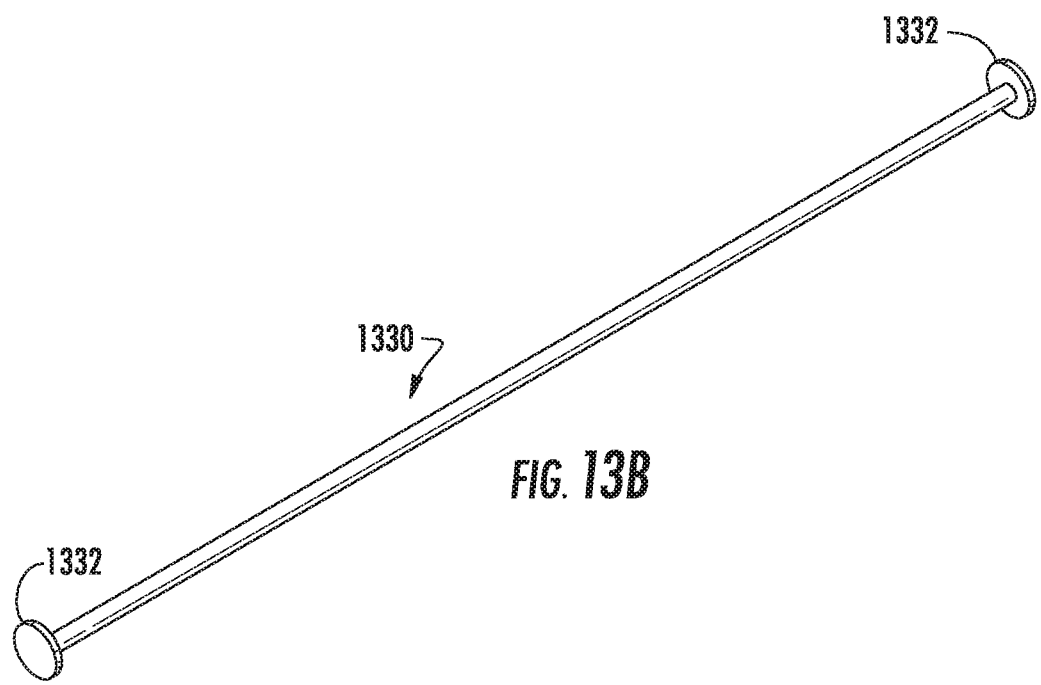
FIG. 13B is a perspective view illustrating a pin 1330 for use with a pivot axis of a line enclosure apparatus according to the presently disclosed subject matter.
Figure 14A:
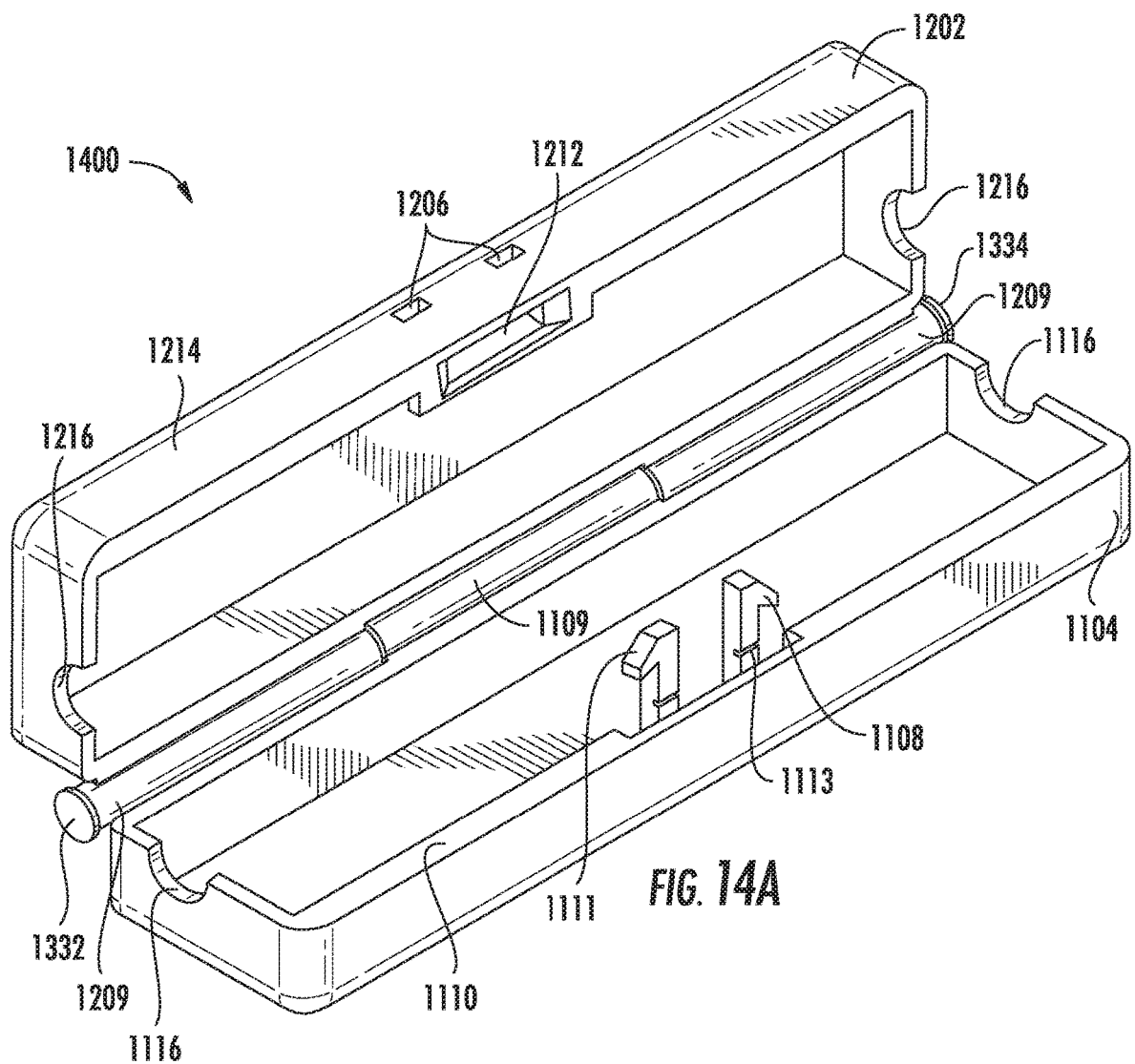
FIG. 14A is a perspective view illustrating a fourth embodiment of a line enclosure apparatus according to the presently disclosed subject matter.
Figure 14B:
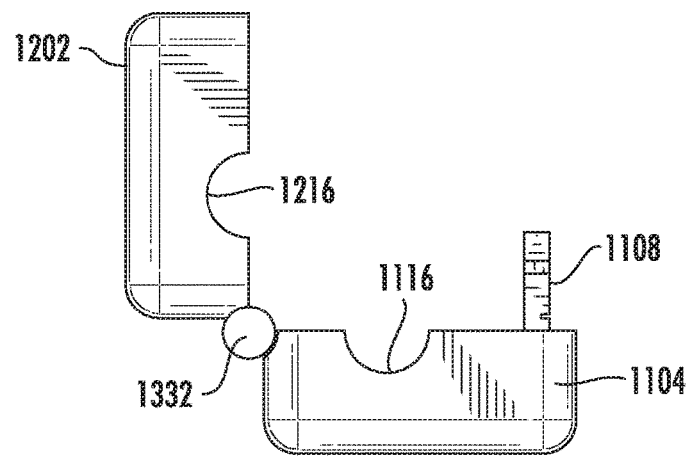
FIG. 14B is a side view illustrating a fourth embodiment of a line enclosure apparatus according to the presently disclosed subject matter.
Figure 14C:
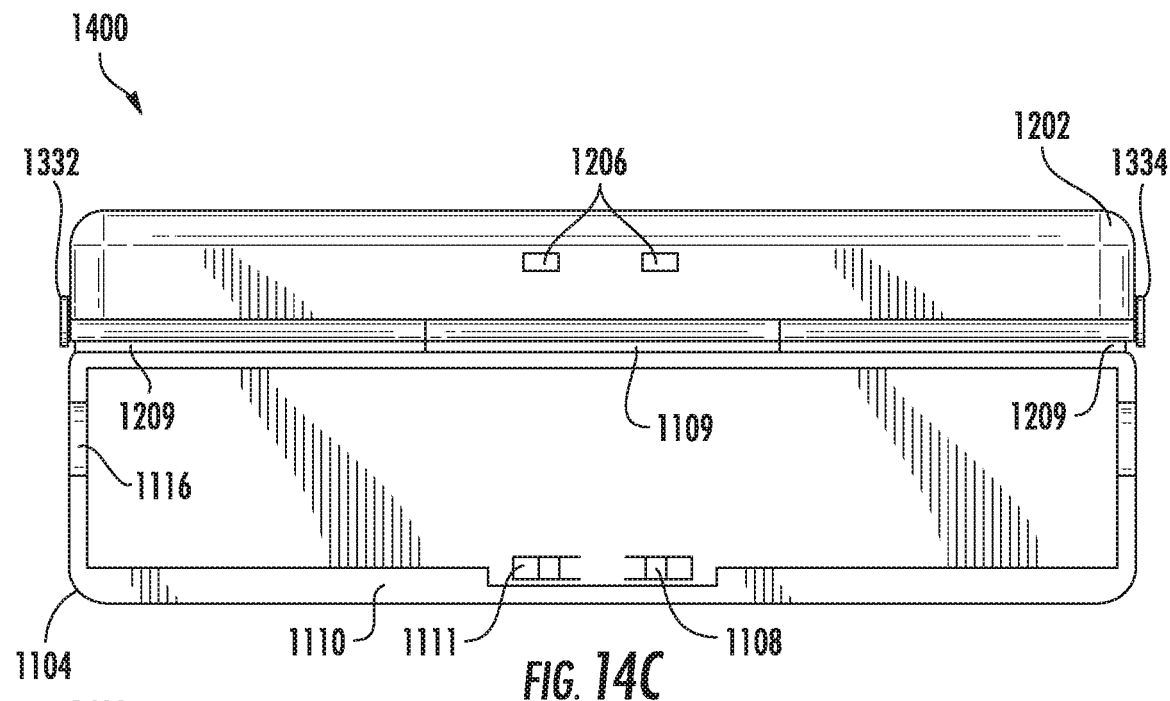
FIG. 14C is a top view illustrating a fourth embodiment of a line enclosure apparatus according to the presently disclosed subject matter.
Figure 14D:
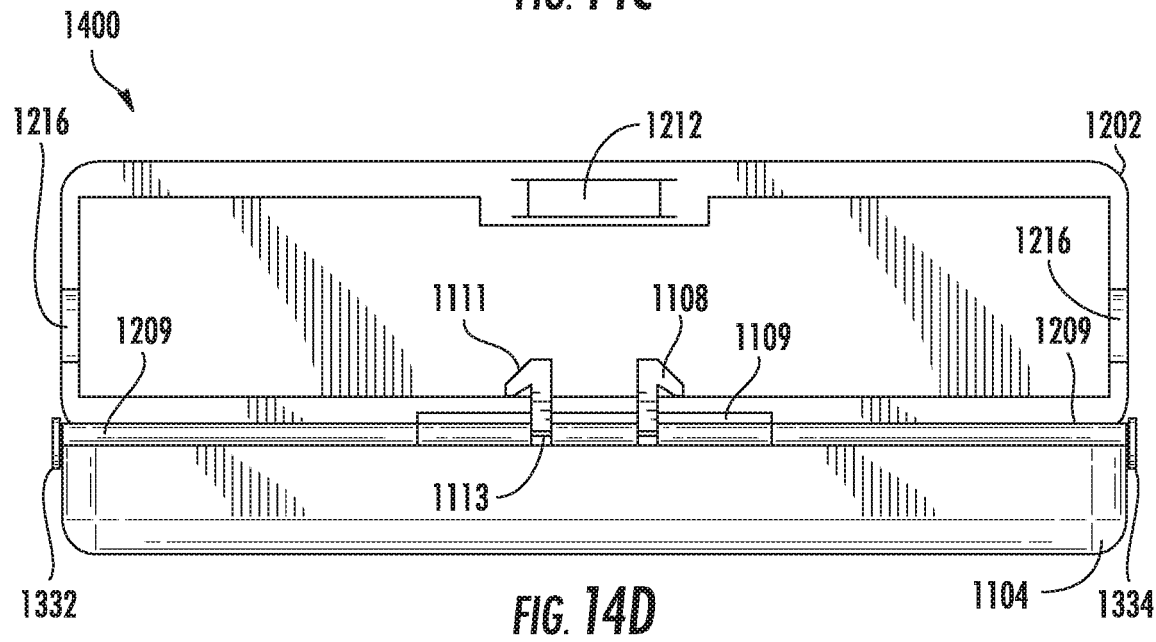
FIG. 14D is a front view illustrating a fourth embodiment of a line enclosure apparatus according to the presently disclosed subject matter.
Figure 16A:
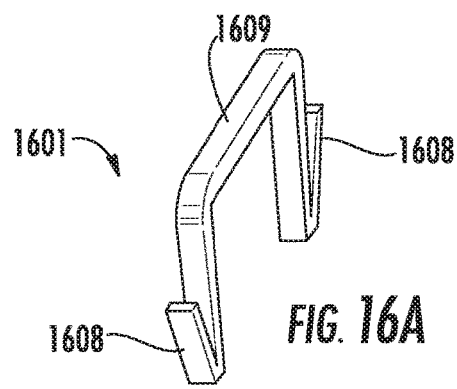
FIG. 16A is a perspective view illustrating a pin 1601 of a fifth embodiment of a line enclosure apparatus according to the presently disclosed subject matter.
Figure 16B:
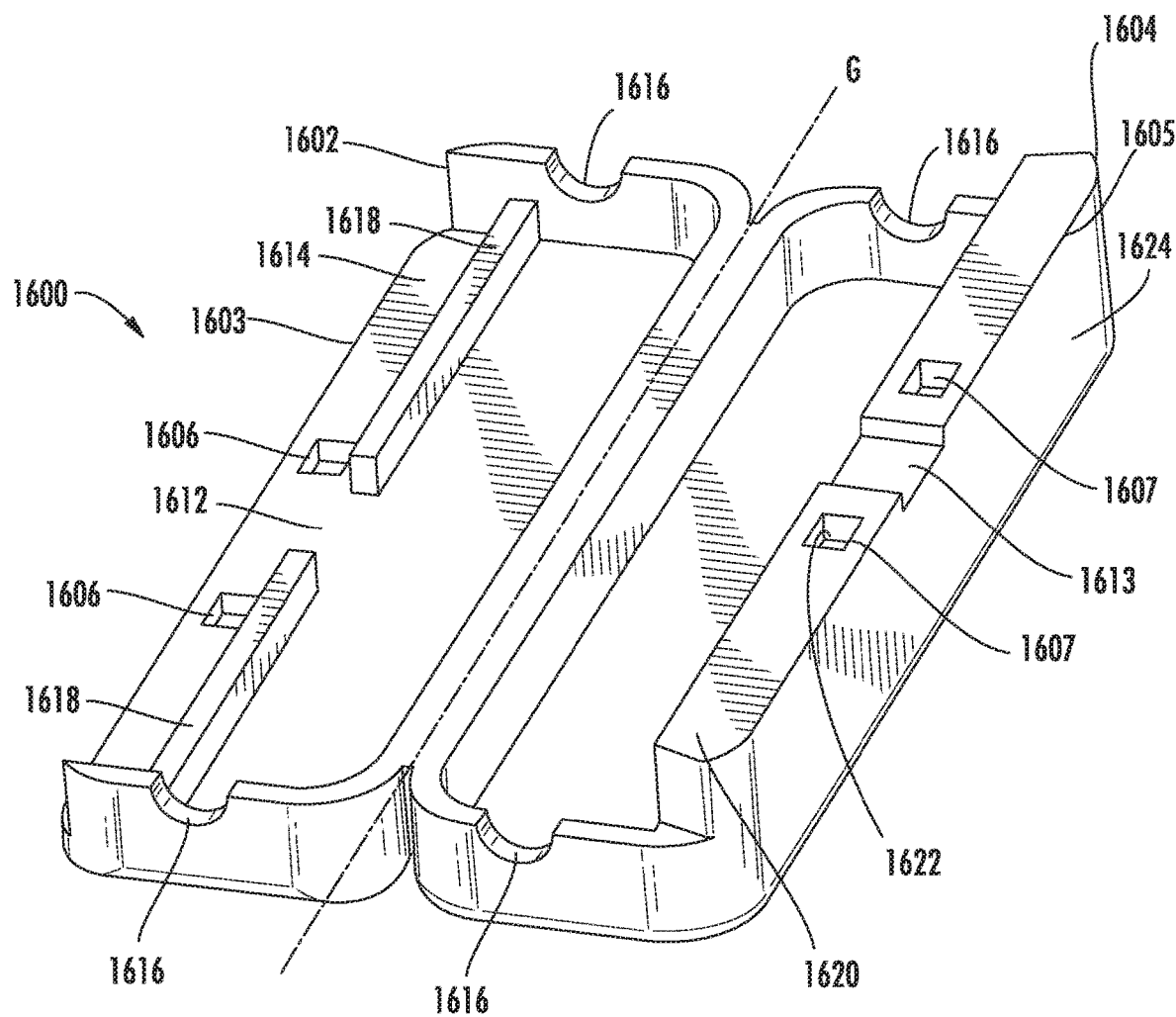
FIG. 16B is a perspective view illustrating a fifth embodiment of a line enclosure apparatus according to the presently disclosed subject matter in an open or unlocked position.
Figure 16C:
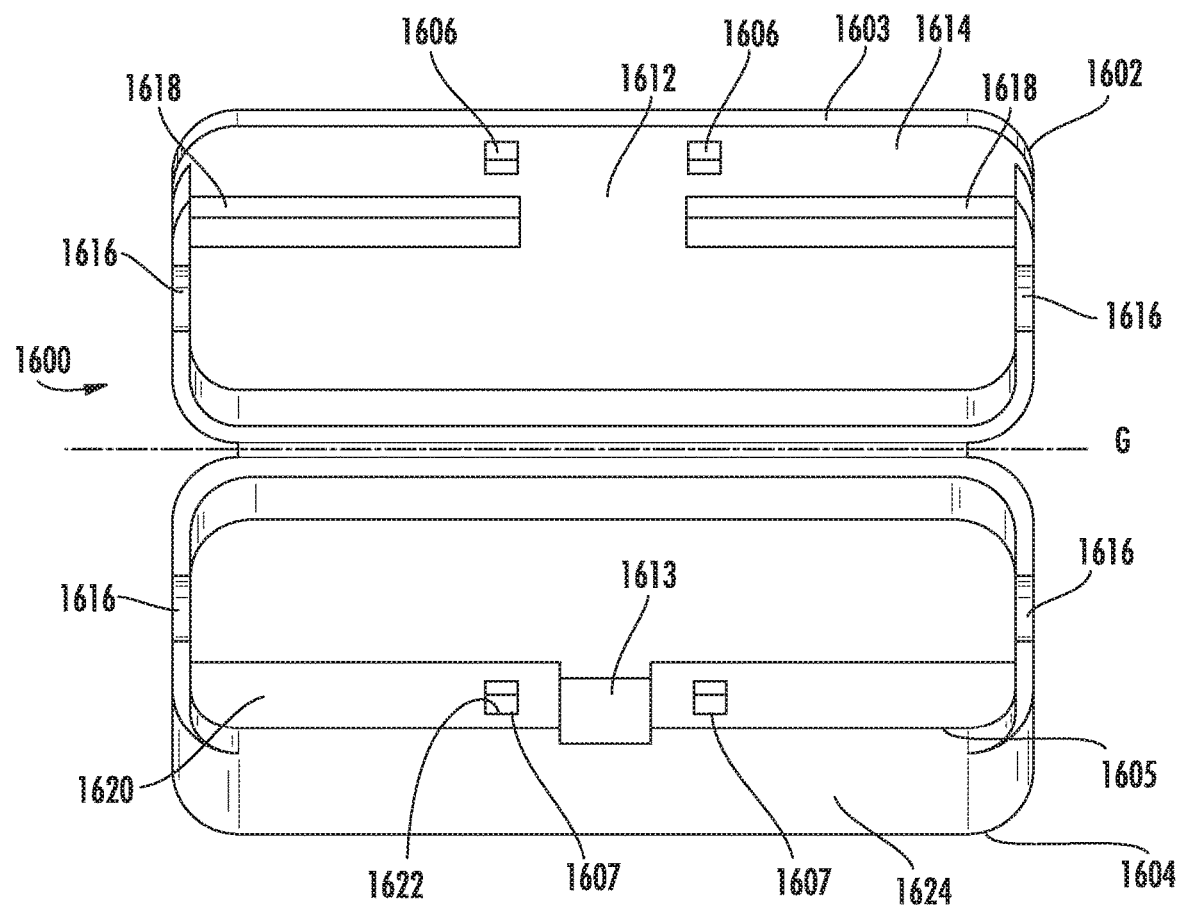
FIG. 16C is a top view illustrating a fifth embodiment of a line enclosure apparatus according to the presently disclosed subject matter in an open or unlocked position.
Figure 16D:
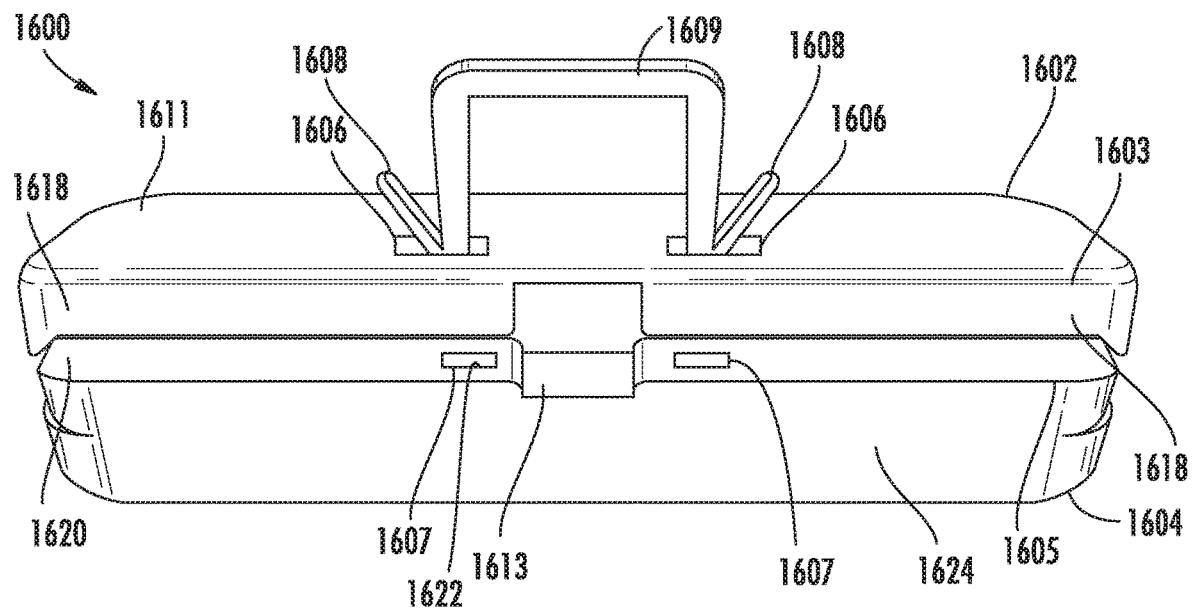
FIG. 16D is a front view illustrating a fifth embodiment of a line enclosure apparatus according to the presently disclosed subject matter in a partially closed or locked position.
Figure 17C:
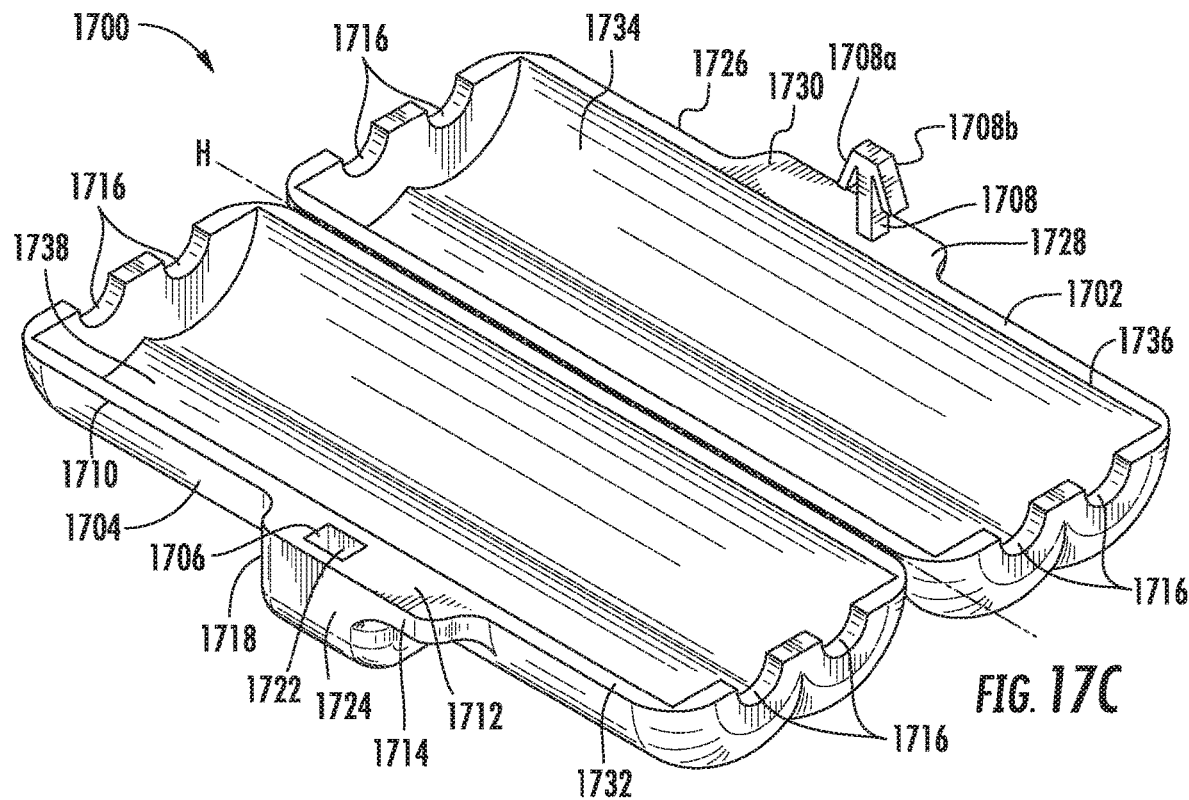
FIG. 17C is a perspective view illustrating an inside of a sixth embodiment in an open or unlocked position according to the presently disclosed subject matter.
Figure 17D:
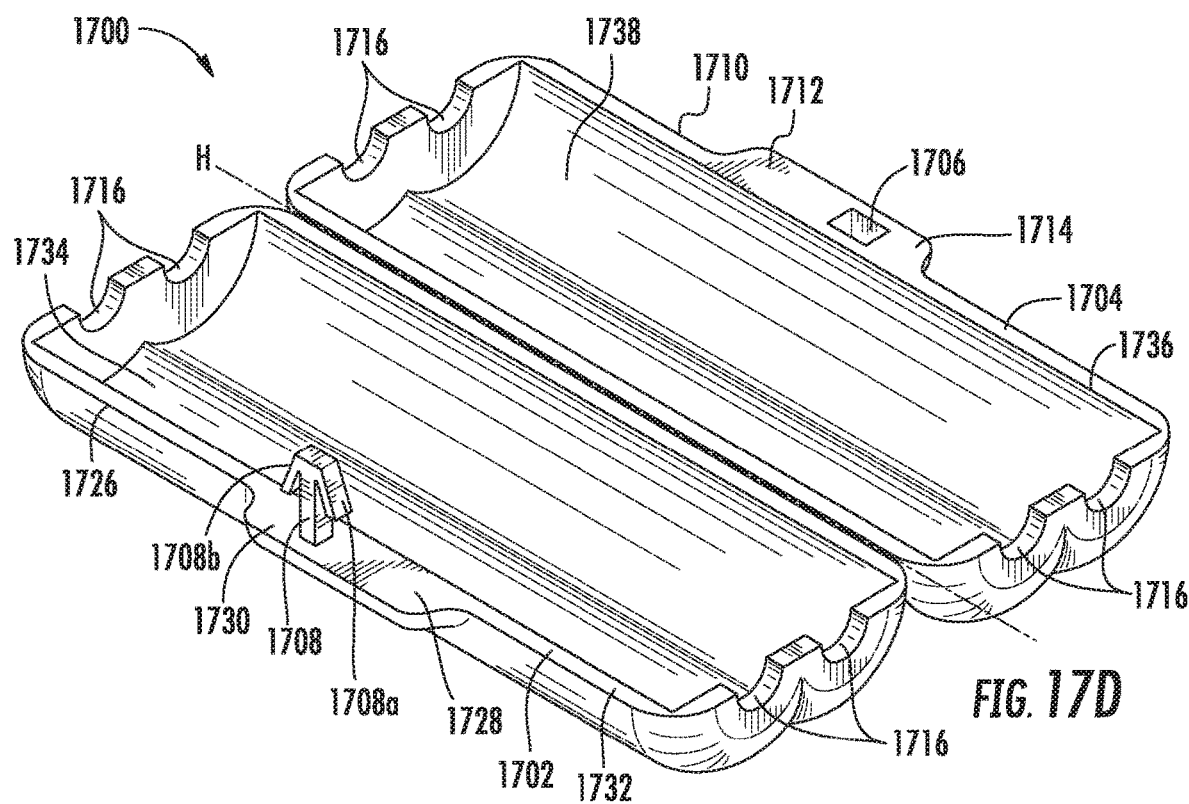
FIG. 17D is a perspective view illustrating an inside of a sixth embodiment in an open or unlocked position, oriented 180° from the view illustrated in FIG. 17C.
Figure 17E:
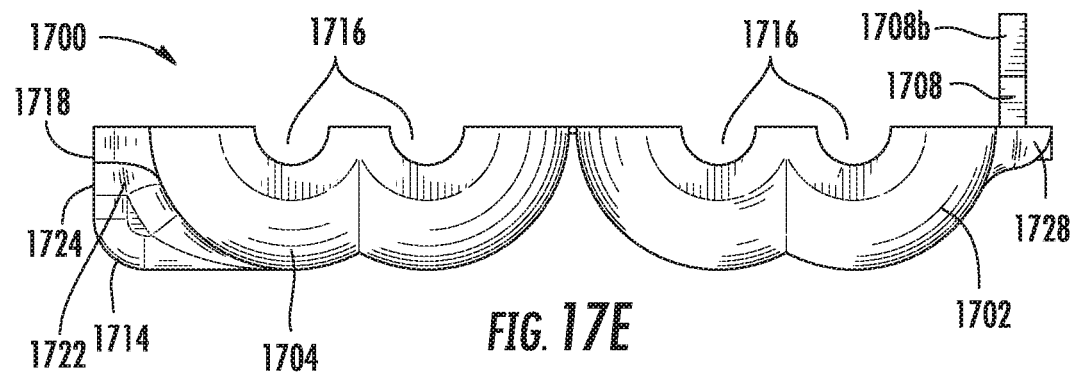
FIG. 17E is an end view illustrating a sixth embodiment of a line enclosure apparatus in an open or unlocked position according to the presently disclosed subject matter.
Figure 17F:
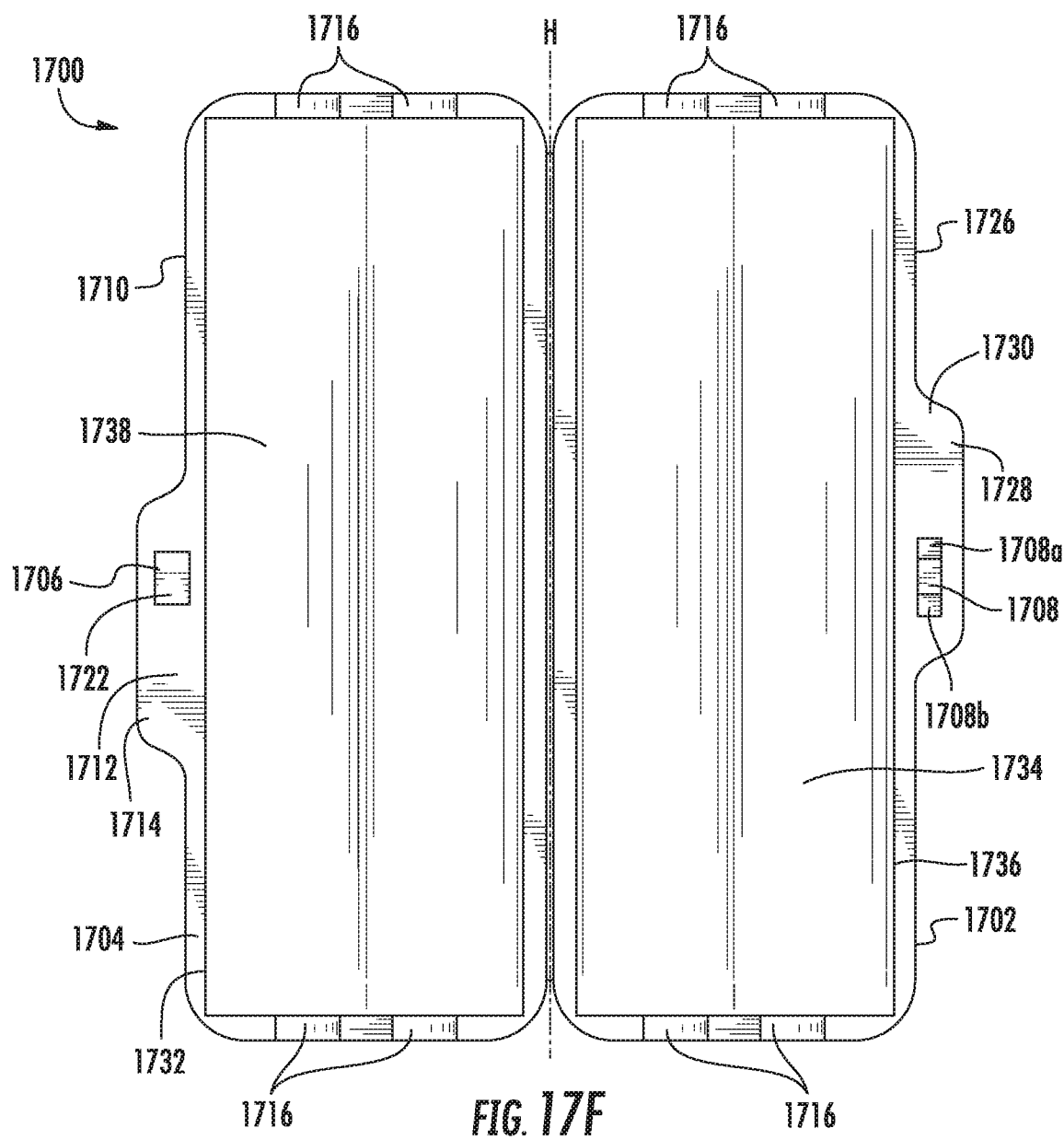
FIG. 17F is a top view illustrating a sixth embodiment of a line enclosure apparatus in an unlocked position according to the presently disclosed subject matter.
Figure 18A:
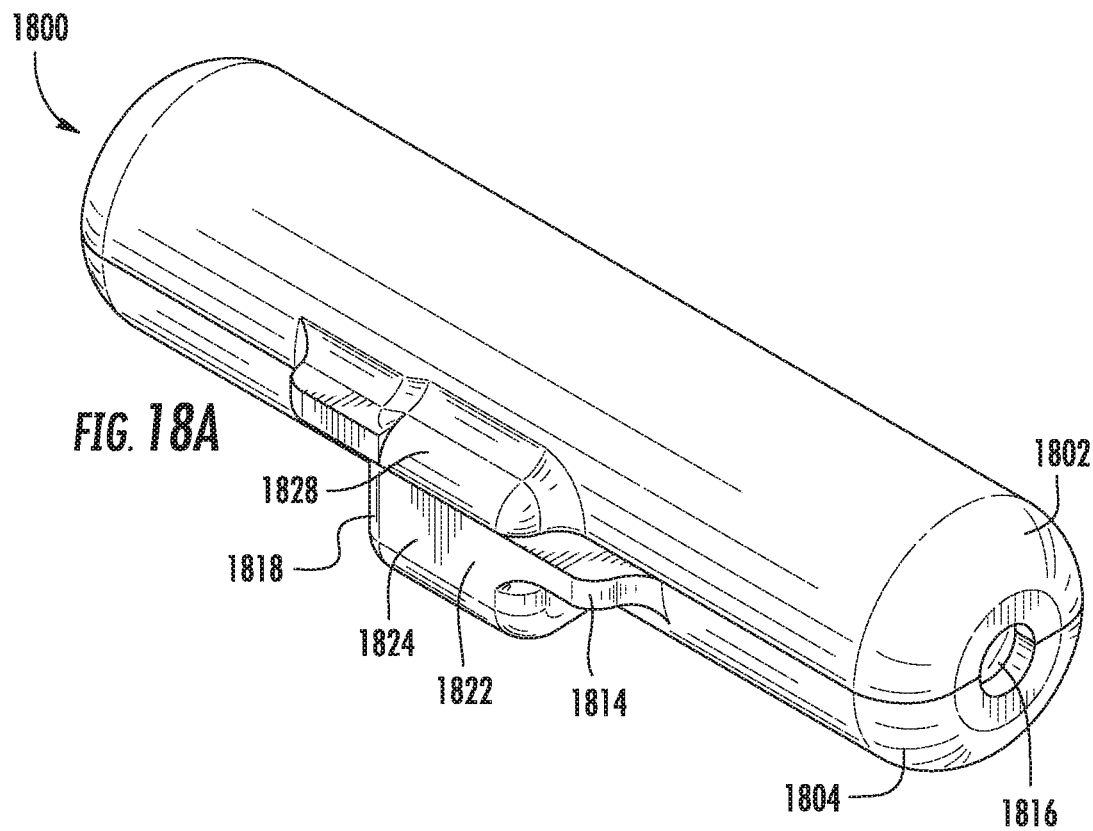
FIG. 18A is a perspective view illustrating a seventh embodiment of a line enclosure apparatus according to the presently disclosed subject matter.
Figure 18B:
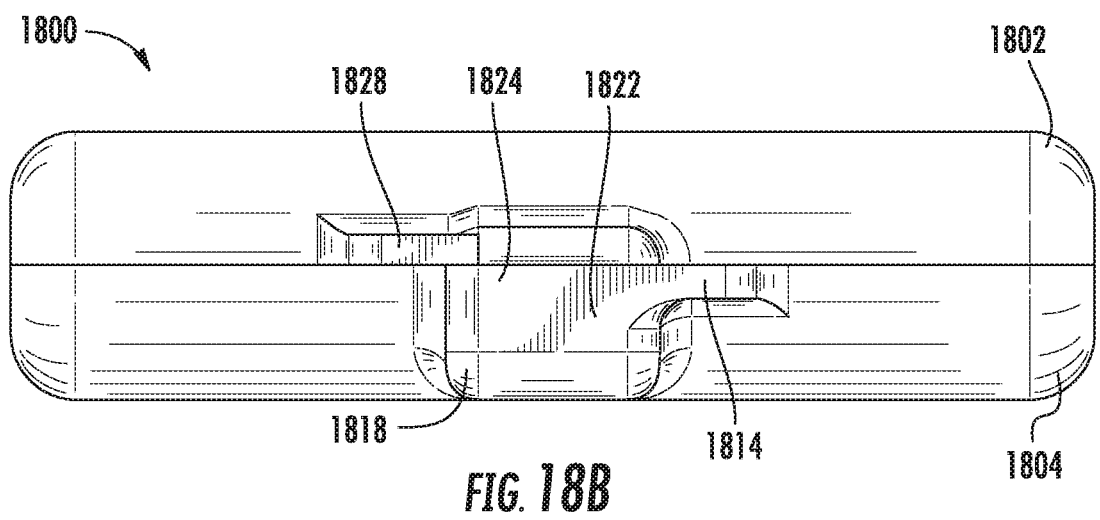
FIG. 18B is a side view illustrating a seventh embodiment of a line enclosure apparatus according to the presently disclosed subject matter.
Figure 18C:
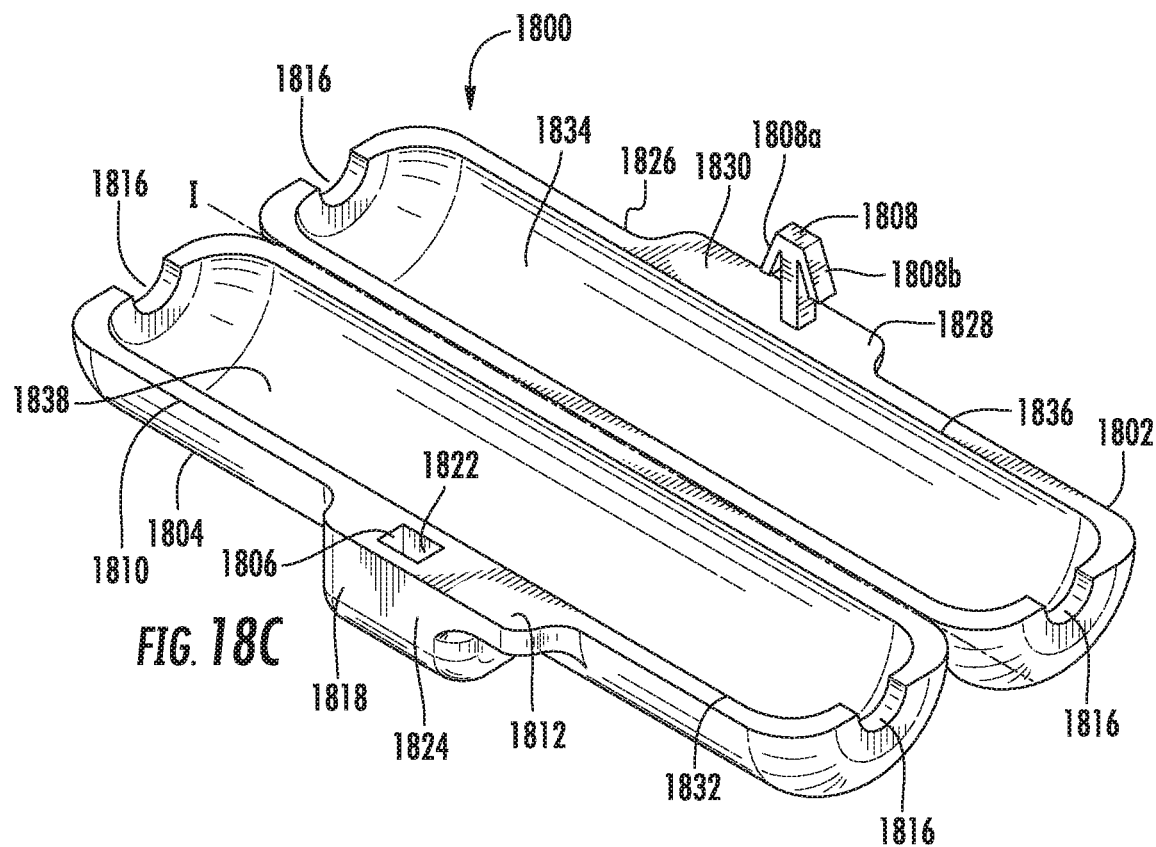
FIG. 18C is a perspective view illustrating an inside of a seventh embodiment in an open or unlocked position according to the presently disclosed subject matter.
Figure 18D:
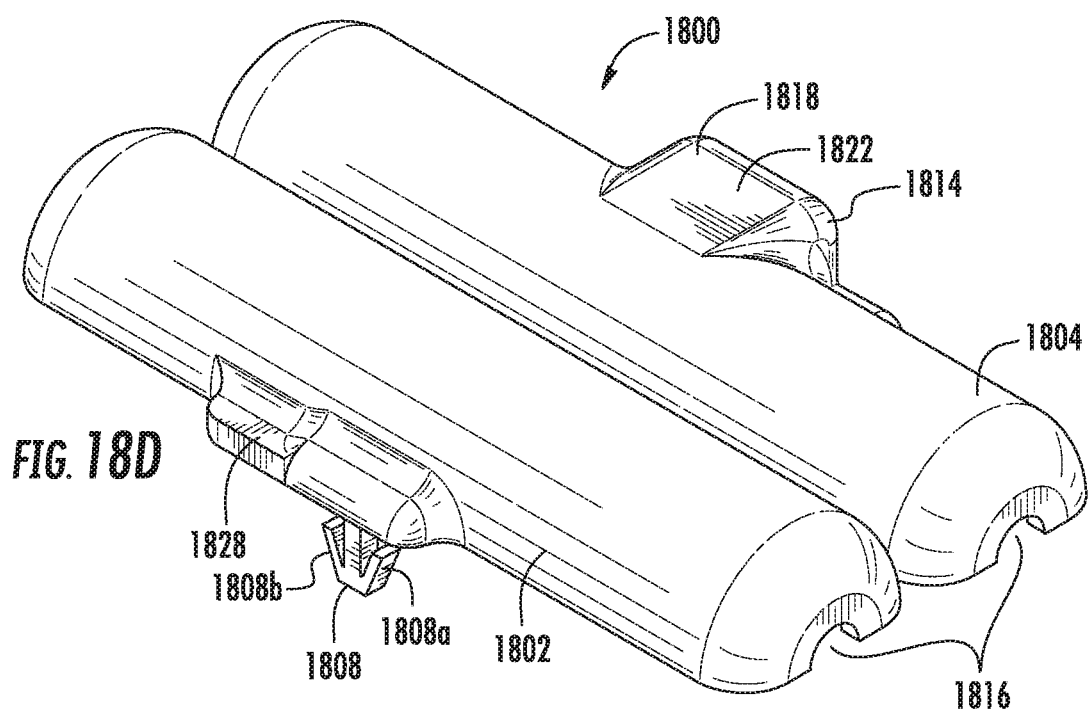
FIG. 18D is a perspective view illustrating an outside of a seventh embodiment in an open or unlocked position according to the presently disclosed subject matter.

Referring now to FIGS. 13A through 13B, pin 1330 is used to interlock parts 1202 and 1104 via hinges 1109, 1209 in making clamping box 1400. Pin 1330 further comprises pin caps 1332 and 1334, which serve to maintain pin 1330 within clamping box 1400 upon installation. Pin 1330 cannot be easily seen in FIGS. 14A through 14D; but, it lies along axis F.

Referring now to FIGS. 15A through 15C, an unlocking mechanism 1500 for unlocking clamping box 1400 illustrated in FIGS. 14A through 14D is illustrated in various views. Unlocking mechanism 1500 can comprise a planar surface 1502 that may be substantially square or rectangular in shape for easy gripping and/or handling by medical personnel. Other shapes, sizes, geometries, etc., for basic unlocking functionality are contemplated as well. Extending from planar surface 1502 is one or more extension 1504, which may be sized and or shaped to comprise teeth (not shown). One or more extensions 1504 may correspondingly fit within one or more hole 1206 illustrated in FIGS. 14A through 14D. For example, in FIGS. 15A through 15C, one or more extension 1504 is formed as a substantially flat rectangular prism. In profile, one or more extension 1504 corresponds to a size and shape of one or more hole 1206 in FIGS. 14A through 14D. Thus, in this example, one or more hole 1206 is sized and shaped to receive a corresponding one of the one or more extension 1504 upon insertion of unlocking mechanism 1500 when clamping box 1400 is in the locked position (see, for example, FIG. 9C). Unlocking mechanism 1500 can further include port 1508. Port 1508 can be placed on a side of unlocking mechanism 1500 substantially opposite the side where the one or more extension 1504 is located. Port 1508 is used to affix unlocking mechanism 1500 to a user's key chain, band, or other device for the purpose of holding and keeping the unlocking mechanism 1500.

Referring now to FIGS. 16A through 16D yet a further embodiment of a clamping box in accordance with the presently disclosed subject matter is referred to generally at 1600. Clamping box 1600 is configured to enclose at least a portion of one or more blood vessel lines therein, although clamping box 1600 may be configured to enclose two or more blood vessel lines (e.g., two, three, four, etc.,). Clamping box 1600 can comprise first part 1602 and second part 1604 that are adapted to be rotated about a pivot axis G towards or away from each other to move between locked or closed positions and unlocked or open positions. Notably, however, first part 1602 and second part 1604 may relate to one another in a manner other than pivoting. For example, a hinge, screw, spring, and/or any other mechanism may allow one or more part of clamping box 1600 to move relative to one another in order to enclose the blood vessel line within. Regardless, first part 1602 and second part 1604 may be manipulated into a closed or locked position and an open or unlocked position. For example, first part 1602 and the second part 1604 may pivot along pivot axis G into a first or unlocked position where the first part 1602 and the second part 1604 are not in direct contact along second longitudinally extending side edges, where the second longitudinally extending side edges are disposed opposite the first longitudinally extending side edges (see, FIGS. 16B-16C). In another example, the first part 1602 and the second part 1604 may pivot along pivot axis G into a second or locked position where the first part 1602 and the second part 1604 are in direct contact along the second longitudinally extending side edges (see, FIG. 16D). In some aspects, clamping box 1600 may comprise more or less than first part 1602 and second part 1604, each of which may be manipulated into locked and/or unlocked positions. For example, clamping box 1600 may comprise one part, three parts, four parts, etc.

In some aspects, clamping box 1600 may have a substantially rounded rectangular prism shape such that each of first part 1602 and second part 1604 form a rounded rectangular prism when pivoted into the locked position. Alternately, in some aspects, clamping box 1600 may have any geometric shape with some basic functionality allowing clamping box 1600 to enclose the blood vessel line within. For example, clamping box 1600 may be square, ovular, triangular, pointed, non-uniform, etc. In other aspects, each box may be manufactured according to the measurements of an extremity of a patient so that the box contours to that extremity. For example, clamping box 1600 may be sized and shaped to conform to a patient's arm.

In some aspects, first part 1602 and second part 1604 are configured to close or lock relative to one another. A locking mechanism disposed on or through either one or both of first part 1602 and second part 1604 may be provided in order to prevent a patient and/or other user from easily gaining entry to the blood vessel line enclosed by clamping box 1600 without detection. However, the locking mechanism may be weak enough to allow for a patient and/or other user to gain entry, if the patient and/or other user is determined to do so. But the locking mechanism is configured so that if tampering does occur, it is easily and quickly detectable by medical personnel. As illustrated in FIGS. 16A-16D, for example, the locking mechanism on clamping box 1600 comprises a pin 1601 having a protrusion 1608 disposed on each end of a u-shaped shaft 1603, optionally in a chamfered configuration.

Continuing with reference to FIGS. 16A-16D, one or more hole 1606 is disposed, optionally centrally disposed, on a first longitudinally extending side edge 1603 of first part 1602. One or more hole 1606 passes through an outer surface 1611 of first part 1602 through to an inner surface 1614 of first part 1602. First part 1602 further comprises supports 1618 disposed on inner surface 1614 on a side of one or more hole 1606 opposite of longitudinal side edge 1603. Supports 1618 extend from ends of first part 1602 towards the center of first part 1602 but are separated by gap 1612. One or more hole 1607 is disposed, optionally centrally disposed, on a second longitudinally extending side edge 1605 of second part 1604. One or more hole 1607 passes through an outer surface 1620 of second part 1604 to an inner compartment 1622 and the outer surface 1620 of second part 1604 also a comprises a transparent window 1624. A recess 1613 is formed centrally on side edge 1605 of second part 1604, adjacent or between one or more hole 1607. When first part 1602 is moved toward second part 1604 first longitudinally extending side edge 1603 of first part 1602 is moved to rest on surface 1620 of second longitudinally extending side edge 1605 of second part 1604, one or more hole 1606 and 1607 are aligned. Recess 1613 is also aligned with gap 1612 between supports 1618. Pin 1601 is then placed in clamping box 1600 such that one or more protrusion 1608 deforms and passes through holes 1606 and 1607 and fits within inner compartment 1622, expanding to lock clamping box 1600.

Thus, pin 1601 is used to lock clamping box 1600. Inner compartment 1622 catches pin 1601 when pin 1601 or box 1600 is broken (either by a key or any other unlocking or breaking mechanism, e.g unlocking mechanism 1500 shown in FIGS. 15A to 15C). By way of example and not limitation, clamping box 1600 can be opened by manipulating pin 1601 such that one or protrusion 1608 is/are broken off pin 1601 and caught in inner compartment 1622. This can be done, for example, by inserting unlocking mechanism 1500 in one or more hole 1606, 1607 disposed on the first part or the second part and/or by inserting unlocking mechanism 1500 into aligned gap 1612 and recess 1613, and manipulating unlocking mechanism 1500 so as to cause breakage of one or protrusion 1608.

In some embodiments, pin 1601 or one or more protrusions 1608 can be a different color from clamping box 1600. As the window 1624 is transparent, pin 1601 or parts thereof (e.g., one or more protrusions 1608) can be easily seen in compartment 1622. This makes it easy to detect tampering. This is particularly the case when pin 1601 or parts thereof are a different color than clamping box 1600. This configuration also makes box 1600 readily reusable. Also, first part 1602 or second part 1604 can be configured such that tampering can be detected upon auditory observation of at least a portion of the locking mechanism, for example, pin 1601 or one or more protrusion 1608 in compartment 1622.

In alternative configurations, clamping boxes 600, 800, 1000, and 1400 as described herein above can be provided with a compartment like compartment 1622. For example, one or more protrusion 608, 808, 1008, and 1108 as described herein above, which are designed to break, can be caught in such a compartment.

In some aspects, clamping box 1600 may be 3D printed although other manufacturing techniques such as extruding, injection molding, etc., may be used. In some aspects, clamping box 1600 may be sized to fit at least a portion of a standard blood vessel line therein. For example, a 4 French or larger or smaller in size lumen (see, FIG. 9A, 902B) of a PICC line may be configured to fit within clamping box 1600. In this manner, each of the first part 1602 and the second part 1604 may be formed as hollow halves in order to receive at least a portion of a blood vessel line therein. In some aspects, either one or both of first part 1602 and second part 1604 of clamping box 1600 comprise blood vessel line openings 1616 disposed on opposing side surfaces of clamping box 1600. For example, blood vessel line openings 1616 may comprise semi-circular openings that may allow the blood vessel line to enter and exit clamping box 1600 when the clamping box is in the locked position.

Referring now to FIGS. 17A through 17F yet a further embodiment of a clamping box in accordance with the presently disclosed subject matter is referred to generally at 1700. Clamping box 1700 is configured to enclose at least a portion of two or more blood vessel lines therein, although clamping box 1700 may be configured to enclose additional blood vessel lines (e.g., three, four, etc.,). Clamping box 1700 can comprise first part 1702 and second part 1704 that are adapted to be rotated about a pivot axis H towards or away from each other to move between locked or closed positions and unlocked or open positions. Notably, however, first part 1702 and second part 1704 may relate to one another in a manner other than pivoting. For example, a hinge, screw, spring, and/or any other mechanism may allow one or more part of clamping box 1700 to move relative to one another in order to enclose a blood vessel line or other article within clamping box 1700. Regardless, first part 1702 and second part 1704 may be manipulated into a closed or locked position and an open or unlocked position. For example, first part 1702 and the second part 1704 may pivot along pivot axis H into a first or unlocked position where the first part 1702 and the second part 1704 are not in direct contact along second longitudinally extending side edges, where the second longitudinally extending side edges are disposed opposite the first longitudinally extending side edges (see, FIGS. 17B-17F). In another example, the first part 1702 and the second part 1704 may pivot along pivot axis H into a second or locked position where the first part 1702 and the second part 1704 are in direct contact along the second longitudinally extending side edges (see, FIG. 17A). In some aspects, clamping box 1700 may comprise more or less than first part 1702 and second part 1704, each of which may be manipulated into locked and/or unlocked positions. For example, clamping box 1700 may comprise one part, three parts, four parts, etc.

In some aspects, clamping box 1700 may have a substantially cylindrical shape such that each of first part 1702 and second part 1704 form a cylinder when pivoted into the locked or closed position. Alternately, in some aspects, clamping box 1700 may have any geometric shape with some basic functionality allowing clamping box 1700 to enclose the blood vessel line within. For example, clamping box 1700 may be square, ovular, triangular, pointed, non-uniform, etc. In other aspects, each box may be manufactured according to the measurements of an extremity of a patient so that the box contours to that extremity. For example, clamping box 1700 may be sized and shaped to conform to a patient's arm.

In some aspects, first part 1702 and second part 1704 are configured to close or lock relative to one another. A locking mechanism disposed on or through either one or both of first part 1702 and second part 1704 may be provided in order to prevent a patient and/or other user from easily gaining entry to the blood vessel line enclosed by clamping box 1700 without detection. However, the locking mechanism may be weak enough to allow for a patient and/or other user to gain entry, if the patient and/or other user is determined to do so. But the locking mechanism is configured so that if tampering does occur, it is easily and quickly detectable by medical personnel. As illustrated in FIGS. 17A-17F, for example, the locking mechanism on clamping box 1700 comprises a post 1708 having sacrificial protrusions 1708*a* and 1708*b* disposed thereon, optionally in a chamfered configuration.

Continuing with reference to FIGS. 17C-17F, one or more hole 1706 is disposed, optionally centrally disposed, on a first longitudinally extending side edge 1710 of part 1704. Longitudinally extending side edge 1710 extends away from axis H to define support 1714. One or more hole 1706 passes through a surface 1712 of support 1714 through to an inner compartment 1722. The outer surface 1718 of support 1714 can optionally comprise but does not have to comprises a transparent window 1724. Indeed, in some embodiments, compartment 1722 is hidden, that is, not readily apparent to a user upon review of clamping box 1700, particularly when clamping box 1700 is in a closed position.

Continuing with reference to FIGS. 17A-17F, post 1708 is disposed, optionally centrally disposed, on a longitudinally extending side edge 1726 of part 1702. Longitudinally extending side edge 1726 extends away from axis H to define support 1728. Post 1708 extends from a surface 1730 of support 1728. When first part 1702 is moved toward second part 1704, surface 1730 of support 1728 is moved to rest on surface 1712 of support 1714 and one or more hole 1706 and post 1708 are aligned. Post 1708 is then positioned such that one or protrusion 1708*a* and 1708*b* deforms and passes through one or hole 1706 and fits within inner compartment 1722, expanding to lock clamping box 1700. While post 1708 and one or more hole 1706 are shown outside the periphery 1732 of the interior 1734 of first part 1702 and the periphery 1736 of the interior 1738 of second part 1704, respectively, of clamping box 1700, they can be provided within the periphery 1732 of the interior 1734 of first part 1702 and the periphery 1736 of the interior 1738 of second part 1704. For example, supports 1714 and 1728 can be extend from longitudinally extending side edges 1710 and 1726, respectively, inwardly towards axis H and post 1708 and one or more hole 1706 can provided in and/or supports 1714 and 1728 in this configuration.

Thus, post 1708 is used to lock clamping box 1700. Inner compartment 1722 catches post 1708 when post 1708 or box 1700 is broken (either by hand by a user or by a key or any other unlocking or breaking mechanism, e.g unlocking mechanism 1500 shown in FIGS. 15A to 15C). By way of example and not limitation, clamping box 1700 can be opened by manipulating post 1708 by applying force or otherwise manipulating supports 1714 and 1728 such that one or sacrificial protrusions 1708*a* and 1708*b* is/are broken off post 1708 and caught in inner compartment 1722. By way of particular example, supports 1714 and 1728 are used as an anchor for a user's thumbs and/or fingers to twist clamping box 1700 open, such as via a twist between thumb and index finger of a user.

In some embodiments, post 1708 or one or more protrusions 1708*a* and 1708*b* can be a different color from clamping box 1700. As window 1724 can be transparent, post 1708 or parts thereof (e.g., one or more protrusions 1708*a* and 1708*b*) can be easily seen in compartment 1722. This makes it easy to detect tampering. This is particularly the case when post 1708 or parts thereof are a different color than clamping box 1700. Also, first part 1702 and/or second part 1704 can be configured such that tampering can be detected upon auditory observation of at least a portion of the locking mechanism, for example, post 1708 or one or more protrusion 1708*a* and 1708*b* in compartment 1722.

In alternative configurations, clamping boxes 600, 800, 1000, and 1400 as described herein above can be provided with a compartment like compartment 1722. For example, one or more protrusion 608, 808, 1008, and 1108 as described herein above, which are designed to break, can be caught in such a compartment.

In some aspects, clamping box 1700 may be 3D printed although other manufacturing techniques such as extruding, injection molding, etc., may be used. In some aspects, clamping box 1700 may be sized to fit at least a portion of a standard blood vessel line therein. For example, a 4 French or larger or smaller in size lumen (see, FIG. 9A, 902B) of a PICC line may be configured to fit within clamping box 1700. In this manner, each of the first part 1702 and the second part 1704 may be formed as hollow halves in order to receive at least a portion of a blood vessel line therein. In some aspects, either one or both of first part 1702 and second part 1704 of clamping box 1700 comprise blood vessel line openings 1716 disposed on opposing side surfaces of clamping box 1700. For example, blood vessel line openings 1716 may comprise semi-circular openings that may allow the blood vessel line to enter and exit clamping box 1700 when the clamping box is in the locked position.

Referring now to FIGS. 18A through 18G, yet a further embodiment of a clamping box in accordance with the presently disclosed subject matter is referred to generally at 1800. Clamping box 1800 is configured to enclose at least a portion of one or more blood vessel lines or other object therein, although clamping box 1800 may be configured to enclose additional blood vessel lines or other objects (e.g., two, three, four, etc.,). Clamping box 1800 can comprise first part 1802 and second part 1804 that are adapted to be rotated about a pivot axis I towards or away from each other to move between locked or closed positions and unlocked or open positions. Notably, however, first part 1802 and second part 1804 may relate to one another in a manner other than pivoting. For example, a hinge, screw, spring, and/or any other mechanism may allow one or more part of clamping box 1800 to move relative to one another in order to enclose the blood vessel line within. Regardless, first part 1802 and second part 1804 may be manipulated into a closed or locked position and an open or unlocked position. For example, first part 1802 and the second part 1804 may pivot along pivot axis I into a first or unlocked position where the first part 1802 and the second part 1804 are not in direct contact along second longitudinally extending side edges, where the second longitudinally extending side edges are disposed opposite the first longitudinally extending side edges (see, FIGS. 18C, 18D, 18E, and 18G). In another example, the first part 1802 and the second part 1804 may pivot along pivot axis I into a second or locked position where the first part 1802 and the second part 1804 are in direct contact along the second longitudinally extending side edges (see, FIGS. 18A and 18B). In some aspects, clamping box 1800 may comprise more or less than first part 1802 and second part 1804, each of which may be manipulated into locked and/or unlocked positions. For example, clamping box 1800 may comprise one part, three parts, four parts, etc.

In some aspects, clamping box 1800 may have a substantially cylindrical shape such that each of first part 1802 and second part 1804 form a cylinder when pivoted into the locked or closed position. Alternately, in some aspects, clamping box 1800 may have any geometric shape with some basic functionality allowing clamping box 1800 to enclose the blood vessel line within. For example, clamping box 1800 may be square, ovular, triangular, pointed, non-uniform, etc. In other aspects, each box may be manufactured according to the measurements of an extremity of a patient so that the box contours to that extremity. For example, clamping box 1800 may be sized and shaped to conform to a patient's arm.

In some aspects, first part 1802 and second part 1804 are configured to close or lock relative to one another. A locking mechanism disposed on or through either one or both of first part 1802 and second part 1804 may be provided in order to prevent a patient and/or other user from easily gaining entry to the blood vessel line enclosed by clamping box 1800 without detection. However, the locking mechanism may be weak enough to allow for a patient and/or other user to gain entry, if the patient and/or other user is determined to do so. But the locking mechanism is configured so that if tampering does occur, it is easily and quickly detectable by medical personnel. As illustrated in FIGS. 18A-18G, for example, the locking mechanism on clamping box 1800 comprises a post 1808 having sacrificial protrusions 1808a and 1808b disposed thereon, optionally in a chamfered configuration.

Continuing with reference to FIGS. 18C-18G, one or more hole 1806 is disposed, optionally centrally disposed, on a first longitudinally extending side edge 1810 of part 1804. Longitudinally extending side edge 1810 extends away from axis I to define support 1814. One or more hole 1806 passes through a surface 1812 of support 1814 through to an inner compartment 1822. The outer surface 1818 of support 1814 can optionally comprise but does not have to comprises a transparent window 1824. Indeed, in some embodiments, compartment 1822 is hidden, that is, not readily apparent to a user upon review of clamping box 1800, particularly when clamping box 1800 is in a closed position.

Continuing with reference to FIGS. 18A-18F, post 1808 is disposed, optionally centrally disposed, on a longitudinally extending side edge 1826 of part 1802. Longitudinally extending side edge 1826 extends away from axis I to define support 1828. Post 1808 extends from a surface 1830 of support 1828. When first part 1802 is moved toward second part 1804, surface 1830 of support 1828 is moved to rest on surface 1812 of support 1814 and one or more hole 1806 and post 1808 are aligned. Post 1808 is then positioned such that one or protrusion 1808a and 1808b deforms and passes through one or hole 1806 and fits within inner compartment 1822, expanding to lock clamping box 1800. While post 1808 and one or more hole 1806 are shown outside the periphery 1832 of the interior 1834 of first part 1802 and the periphery 1836 of the interior 1838 of second part 1804, respectively, of clamping box 1800, they can be provided within the periphery 1832 of the interior 1834 of first part 1802 and the periphery 1836 of the interior 1838 of second part 1804. For example, supports 1814 and 1828 can be extend from longitudinally extending side edges 1810 and 1826, respectively, inwardly towards axis I and post 1808 and one or more hole 1806 can provided in and/or supports 1814 and 1828 in this configuration.

Thus, post 1808 is used to lock clamping box 1800. Inner compartment 1822 catches post 1808 when post 1808 or box 1800 is broken (either by hand by a user or by a key or any other unlocking or breaking mechanism, e.g unlocking mechanism 1500 shown in FIGS. 15A to 15C). By way of example and not limitation, clamping box 1800 can be opened by manipulating post 1808 by putting force or otherwise manipulating supports 1814 and 1828 such that one or sacrificial protrusions 1808a and 1808b is/are broken off post 1808 and caught in inner compartment 1822. By way of particular example, supports 1814 and 1828 are used as an anchor for a user's thumbs and/or fingers to twist clamping box 1800 open, such as via a twist between thumb and index finger of a user.

In some embodiments, post 1808 or one or more protrusions 1808a and 1808b can be a different color from clamping box 1800. As window 1824 can be transparent, post 1808 or parts thereof (e.g., one or more protrusions 1808a and 1808b) can be easily seen in compartment 1822. This makes it easy to detect tampering. This is particularly the case when post 1808 or parts thereof are a different color than clamping box 1800. Also, first part 1802 and/or second part 1804 can be configured such that tampering can be detected upon auditory observation of at least a portion of the locking mechanism, for example, post 1808 or one or more protrusion 1808a and 1808b in compartment 1822.

In alternative configurations, clamping boxes 600, 800, 1000, and 1400 as described herein above can be provided with a compartment like compartment 1822. For example, one or more protrusion 608, 808, 1008, and 1108 as described herein above, which are designed to break, can be caught in such a compartment.

In some aspects, clamping box 1800 may be 3D printed although other manufacturing techniques such as extruding, injection molding, etc., may be used. In some aspects, clamping box 1800 may be sized to fit at least a portion of a standard blood vessel line therein. For example, a 4 French or larger or smaller in size lumen (see, FIG. 9A, 902B) of a PICC line may be configured to fit within clamping box 1800. In this manner, each of the first part 1802 and the second part 1804 may be formed as hollow halves in order to receive at least a portion of a blood vessel line therein. In some aspects, either one or both of first part 1802 and second part 1804 of clamping box 1800 comprise blood vessel line openings 1816 disposed on opposing side surfaces of clamping box 1800. For example, blood vessel line openings 1816 may comprise semi-circular openings that may allow the blood vessel line to enter and exit clamping box 1800 when the clamping box is in the locked position.

Figure 19A:
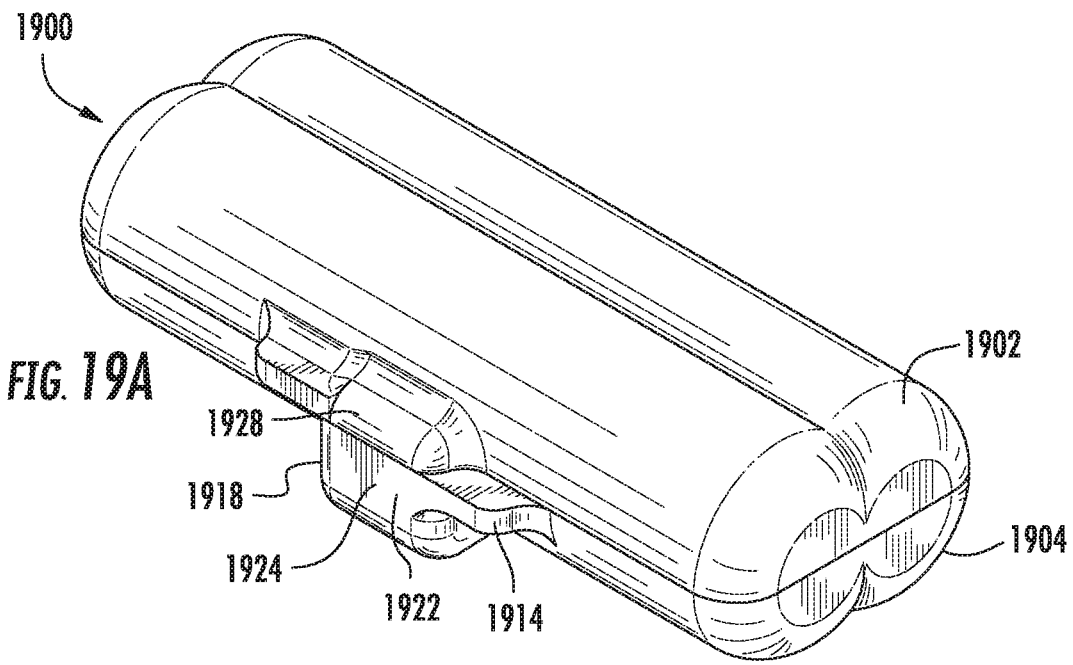
FIG. 19A is a perspective view illustrating an eighth embodiment of a line enclosure apparatus according to the presently disclosed subject matter.
Figure 19B:
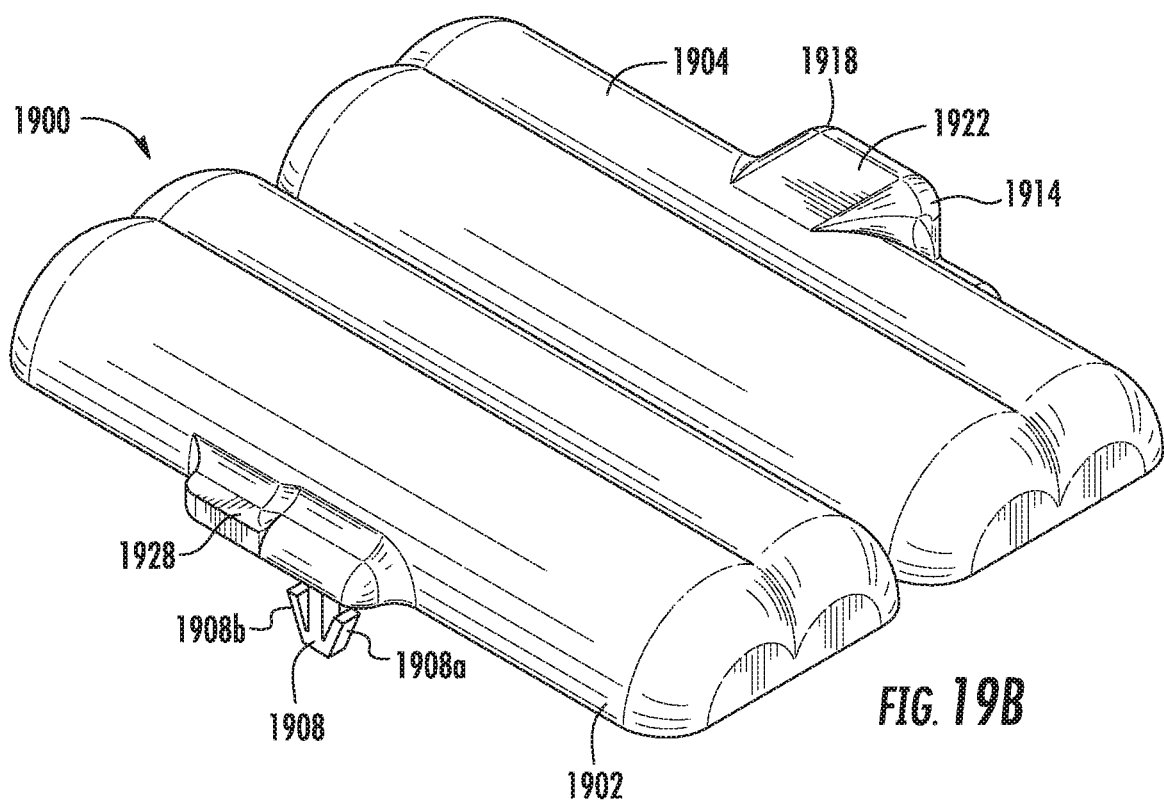
FIG. 19B is a perspective view illustrating an outside of an eighth embodiment in an open or unlocked position according to the presently disclosed subject matter.
Figure 19C:
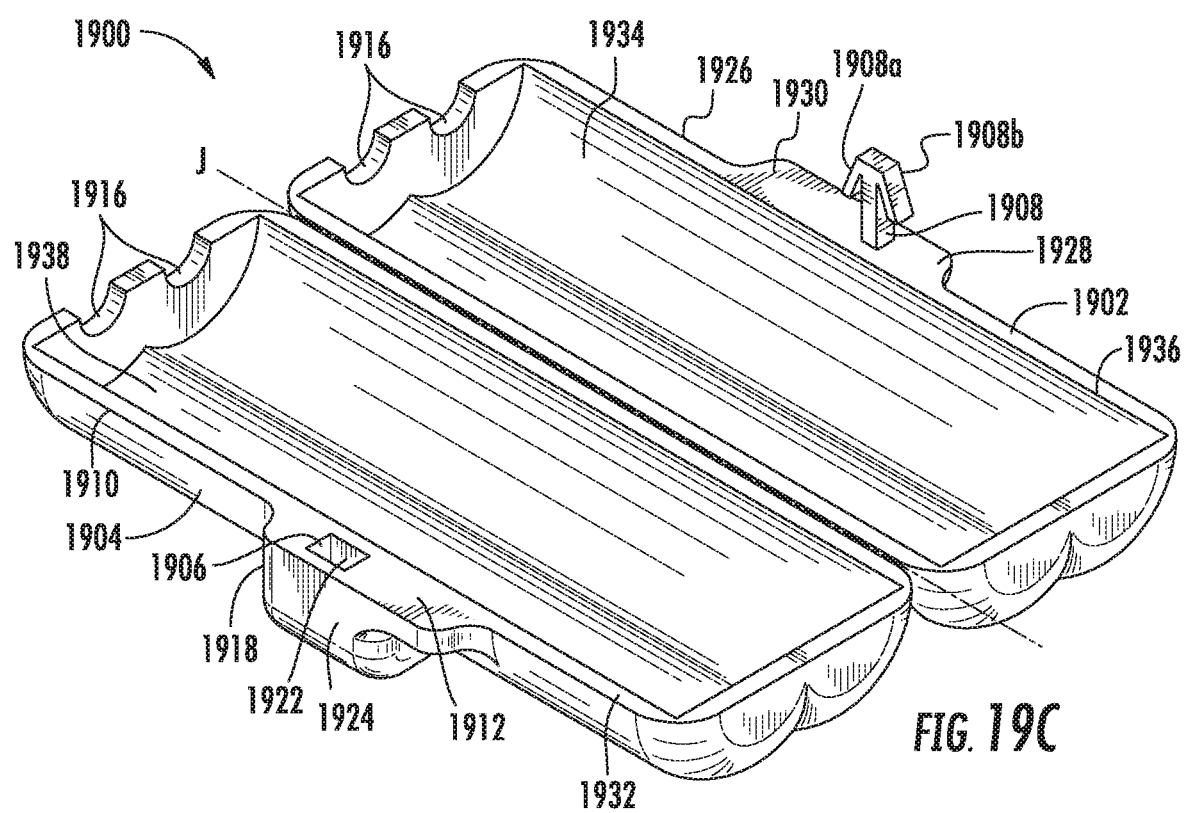
FIG. 19C is a perspective view illustrating an inside of an eighth embodiment in an open or unlocked position according to the presently disclosed subject matter.

Referring now to FIGS. 19A through 19C, yet a further embodiment of a clamping box in accordance with the presently disclosed subject matter is referred to generally at 1900. Clamping box 1900 is configured to enclose at least a portion of two or more blood vessel lines therein, although clamping box 1900 may be configured to enclose additional blood vessel lines (e.g., three, four, etc.,) or other object or objects. Clamping box 1900 can comprise first part 1902 and second part 1904 that are adapted to be rotated about a pivot axis J towards or away from each other to move between locked or closed positions and unlocked or open positions. Notably, however, first part 1902 and second part 1904 may relate to one another in a manner other than pivoting. For example, a hinge, screw, spring, and/or any other mechanism may allow one or more part of clamping box 1900 to move relative to one another in order to enclose the blood vessel line within. Regardless, first part 1902 and second part 1904 may be manipulated into a closed or locked position and an open or unlocked position. For example, first part 1902 and the second part 1904 may pivot along pivot axis J into a first or unlocked position where the first part 1902 and the second part 1904 are not in direct contact along second longitudinally extending side edges, where the second longitudinally extending side edges are disposed opposite the first longitudinally extending side edges. In another example, the first part 1902 and the second part 1904 may pivot along pivot axis J into a second or locked position where the first part 1902 and the second part 1904 are in direct contact along the second longitudinally extending side edges. In some aspects, clamping box 1900 may comprise more or less than first part 1902 and second part 1904, each of which may be manipulated into locked and/or unlocked positions. For example, clamping box 1900 may comprise one part, three parts, four parts, etc. Clamping box 1900 includes blood vessel line opening 1916 on one end only and is covered or closed on the other side (that is, only inlet and no outlet).

In some aspects, clamping box 1900 may have a substantially cylindrical shape such that each of first part 1902 and second part 1904 form a cylinder when pivoted into the locked or closed position. Alternately, in some aspects, clamping box 1900 may have any geometric shape with some basic functionality allowing clamping box 1900 to enclose the blood vessel line within. For example, clamping box 1900 may be square, ovular, triangular, pointed, non-uniform, etc. In other aspects, each box may be manufactured according to the measurements of an extremity of a patient so that the box contours to that extremity. For example, clamping box 1900 may be sized and shaped to conform to a patient's arm.

In some aspects, first part 1902 and second part 1904 are configured to close or lock relative to one another. A locking mechanism disposed on or through either one or both of first part 1902 and second part 1904 may be provided in order to prevent a patient and/or other user from easily gaining entry to the blood vessel line enclosed by clamping box 1900 without detection. However, the locking mechanism may be weak enough to allow for a patient and/or other user to gain entry, if the patient and/or other user is determined to do so. But the locking mechanism is configured so that if tampering does occur, it is easily and quickly detectable by medical personnel. As illustrated in FIGS. 19A-19C, for example, the locking mechanism on clamping box 1900 comprises a post 1908 having sacrificial protrusions 1908a and 1908b disposed thereon, optionally in a chamfered configuration.

Continuing with reference to FIGS. 19A-19C, one or more hole 1906 is disposed, optionally centrally disposed, on a first longitudinally extending side edge 1910 of part 1904. Longitudinally extending side edge 1910 extends away from axis J to define support 1914. One or more hole 1906 passes through a surface 1912 of support 1914 through to an inner compartment 1922. The outer surface 1918 of support 1914 can optionally comprise but does not have to comprises a transparent window 1924. Indeed, in some embodiments, compartment 1922 is hidden, that is, not readily apparent to a user upon review of clamping box 1900, particularly when clamping box 1900 is in a closed position.

Continuing with reference to FIGS. 19A-19C, post 1908 is disposed, optionally centrally disposed, on a longitudinally extending side edge 1926 of part 1902. Longitudinally extending side edge 1926 extends away from axis J to define support 1928. Post 1908 extends from a surface 1930 of support 1928. When first part 1902 is moved toward second part 1904, surface 1930 of support 1928 is moved to rest on surface 1912 of support 1914 and one or more hole 1906 and post 1908 are aligned. Post 1908 is then positioned such that one or protrusion 1908a and 1908b deforms and passes through one or hole 1906 and fits within inner compartment 1922, expanding to lock clamping box 1900. While post 1908 and one or more hole 1906 are shown outside the periphery 1932 of the interior 1934 of first part 1902 and the periphery 1936 of the interior 1938 of second part 1904, respectively, of clamping box 1900, they can be provided within the periphery 1932 of the interior 1934 of first part 1902 and the periphery 1936 of the interior 1938 of second part 1904. For example, supports 1914 and 1928 can be extend from longitudinally extending side edges 1910 and 1926, respectively, inwardly towards axis J and post 1908 and one or more hole 1906 can provided in and/or supports 1914 and 1928 in this configuration.

Thus, post 1908 is used to lock clamping box 1900. Inner compartment 1922 catches post 1908 when post 1908 or box 1900 is broken (either by hand by a user or by a key or any other unlocking or breaking mechanism, e.g unlocking mechanism 1500 shown in FIGS. 15A to 15C). By way of example and not limitation, clamping box 1900 can be opened by manipulating post 1908 by putting force or otherwise manipulating supports 1914 and 1928 such that one or sacrificial protrusions 1908a and 1908b is/are broken off post 1908 and caught in inner compartment 1922. By way of particular example, supports 1914 and 1928 are used as an anchor for a user's thumbs and/or fingers to twist clamping box 1900 open, such as via a twist between thumb and index finger of a user.

In some embodiments, post 1908 or one or more protrusions 1908a and 1908b can be a different color from clamping box 1900. As window 1924 can be transparent, post 1908 or parts thereof (e.g., one or more protrusions 1908a and 1908b) can be easily seen in compartment 1922. This makes it easy to detect tampering. This is particularly the case when post 1908 or parts thereof are a different color than clamping box 1900. Also, first part 1902 and/or second part 1904 can be configured such that tampering can be detected upon auditory observation of at least a portion of the locking mechanism, for example, post 1908 or one or more protrusion 1908a and 1908b in compartment 1922.

In alternative configurations, clamping boxes 600, 800, 1000, and 1400 as described herein above can be provided with a compartment like compartment 1922. For example, one or more protrusion 608, 808, 1008, and 1108 as described herein above, which are designed to break, can be caught in such a compartment.

In some aspects, clamping box 1900 may be 3D printed although other manufacturing techniques such as extruding, injection molding, etc., may be used. In some aspects, clamping box 1900 may be sized to fit at least a portion of a standard blood vessel line therein. For example, a 4 French or larger or smaller in size lumen (see, FIG. 9A, 902B) of a PICC line may be configured to fit within clamping box 1900. In this manner, each of the first part 1902 and the second part 1904 may be formed as hollow halves in order to receive at least a portion of a blood vessel line therein. In some aspects, either one or both of first part 1902 and second part 1904 of clamping box 1900 comprise blood vessel line openings 1916 disposed on one side surface of clamping box 1900. For example, blood vessel line openings 1916 may comprise semi-circular openings that may allow the blood vessel line to enter clamping box 1900 when the clamping box is in the locked position.

Figure 20C:
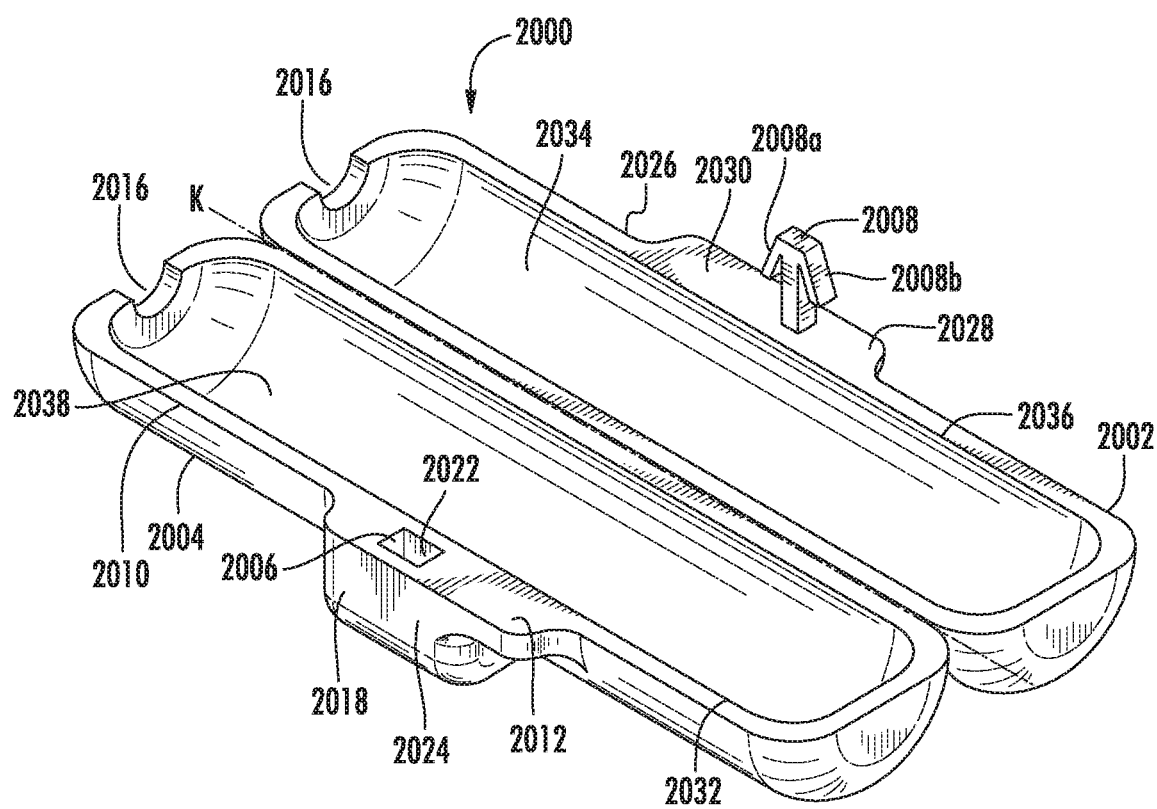
FIG. 20C is a perspective view illustrating an inside of a ninth embodiment in an open or unlocked position according to the presently disclosed subject matter.

Referring now to FIGS. 20A through 20C, yet a further embodiment of a clamping box in accordance with the presently disclosed subject matter is referred to generally at 2000. Clamping box 2000 is configured to enclose at least a portion of one or more blood vessel lines therein, although clamping box 2000 may be configured to enclose additional blood vessel lines (e.g., two, three, four, etc.,) or other object or objects. Clamping box 2000 can comprise first part 2002 and second part 2004 that are adapted to be rotated about a pivot axis K towards or away from each other to move between locked or closed positions and unlocked or open positions. Notably, however, first part 2002 and second part 2004 may relate to one another in a manner other than pivoting. For example, a hinge, screw, spring, and/or any other mechanism may allow one or more part of clamping box 2000 to move relative to one another in order to enclose the blood vessel line within. Regardless, first part 2002 and second part 2004 may be manipulated into a closed or locked position and an open or unlocked position. For example, first part 2002 and the second part 2004 may pivot along pivot axis K into a first or unlocked position where the first part 2002 and the second part 2004 are not in direct contact along second longitudinally extending side edges, where the second longitudinally extending side edges are disposed opposite the first longitudinally extending side edges. In another example, the first part 2002 and the second part 2004 may pivot along pivot axis K into a second or locked position where the first part 2002 and the second part 2004 are in direct contact along the second longitudinally extending side edges. In some aspects, clamping box 2000 may comprise more or less than first part 2002 and second part 2004, each of which may be manipulated into locked and/or unlocked positions. For example, clamping box 2000 may comprise one part, three parts, four parts, etc. Clamping box 2000 includes blood vessel line opening 2016 on one end only and is covered on the other side (that is, only inlet and no outlet).

In some aspects, clamping box 2000 may have a substantially cylindrical shape such that each of first part 2002 and second part 2004 form a cylinder when pivoted into the locked or closed position. Alternately, in some aspects, clamping box 2000 may have any geometric shape with some basic functionality allowing clamping box 2000 to enclose the blood vessel line within. For example, clamping box 2000 may be square, ovular, triangular, pointed, non-uniform, etc. In other aspects, each box may be manufactured according to the measurements of an extremity of a patient so that the box contours to that extremity. For example, clamping box 2000 may be sized and shaped to conform to a patient's arm.

In some aspects, first part 2002 and second part 2004 are configured to close or lock relative to one another. A locking mechanism disposed on or through either one or both of first part 2002 and second part 2004 may be provided in order to prevent a patient and/or other user from easily gaining entry to the blood vessel line enclosed by clamping box 2000 without detection. However, the locking mechanism may be weak enough to allow for a patient and/or other user to gain entry, if the patient and/or other user is determined to do so. But the locking mechanism is configured so that if opening by non-medical personnel does occur, it is easily and quickly detectable by medical personnel. As illustrated in FIGS. 20A-20C, for example, the locking mechanism on clamping box 2000 comprises a post 2008 having sacrificial protrusions 2008a and 2008b disposed thereon, optionally in a chamfered configuration.

Continuing with reference to FIGS. 20A-20C, one or more hole 2006 is disposed, optionally centrally disposed, on a first longitudinally extending side edge 2010 of part 2004. Longitudinally extending side edge 2010 extends away from axis K to define support 2014. One or more hole 2006 passes through a surface 2012 of support 2014 through to an inner compartment 2022. The outer surface 2018 of support 2014 can optionally comprise but does not have to comprises a transparent window 2024. Indeed, in some embodiments, compartment 2022 is hidden, that is, not readily apparent to a user upon review of clamping box 2000, particularly when clamping box 2000 is in a closed position.

Continuing with reference to FIGS. 20A-20C, post 2008 is disposed, optionally centrally disposed, on a longitudinally extending side edge 2026 of part 2002. Longitudinally extending side edge 2026 extends away from axis K to define support 2028. Post 2008 extends from a surface 2030 of support 2028. When first part 2002 is moved toward second part 2004, surface 2030 of support 2028 is moved to rest on surface 2012 of support 2014 and one or more hole 2006 and post 2008 are aligned. Post 2008 is then positioned such that one or protrusion 2008a and 2008b deforms and passes through one or hole 2006 and fits within inner compartment 2022, expanding to lock clamping box 2000. While post 2008 and one or more hole 2006 are shown outside the periphery 2032 of the interior 2034 of first part 2002 and the periphery 2036 of the interior 2038 of second part 2004, respectively, of clamping box 2000, they can be provided within the periphery 2032 of the interior 2034 of first part 2002 and the periphery 2036 of the interior 2038 of second part 2004. For example, supports 2014 and 2028 can be extend from longitudinally extending side edges 2010 and 2026, respectively, inwardly towards axis K and post 2008 and one or more hole 2006 can provided in and/or supports 2014 and 2028 in this configuration.

Thus, post 2008 is used to lock clamping box 2000. Inner compartment 2022 catches post 2008 when post 2008 or box 2000 is broken (either by hand by a user or by a key or any other unlocking or breaking mechanism, e.g unlocking mechanism 1500 shown in FIGS. 15A to 15C). By way of example and not limitation, clamping box 2000 can be opened by manipulating post 2008 by putting force or otherwise manipulating supports 2014 and 2028 such that one or sacrificial protrusions 2008a and 2008b is/are broken off post 2008 and caught in inner compartment 2022. By way of particular example, supports 2014 and 2028 are used as an anchor for a user's thumbs and/or fingers to twist clamping box 2000 open, such as via a twist between thumb and index finger of a user.

In some embodiments, post 2008 or one or more protrusions 2008a and 2008b can be a different color from clamping box 2000. As window 2024 can be transparent, post 2008 or parts thereof (e.g., one or more protrusions 2008a and 2008b) can be easily seen in compartment 2022. This makes it easy to detect tampering. This is particularly the case when post 2008 or parts thereof are a different color than clamping box 2000. Also, first part 2002 and/or second part 2004 can be configured such that tampering can be detected upon auditory observation of at least a portion of the locking mechanism, for example, post 2008 or one or more protrusion 2008a and 2008b in compartment 2022.

In alternative configurations, clamping boxes 600, 800, 1000, and 1400 as described herein above can be provided with a compartment like compartment 2022. For example, one or more protrusion 608, 808, 1008, and 1108 as described herein above, which are designed to break, can be caught in such a compartment.

In some aspects, clamping box 2000 may be 3D printed although other manufacturing techniques such as extruding, injection molding, etc., may be used. In some aspects, clamping box 2000 may be sized to fit at least a portion of a standard blood vessel line therein. For example, a 4 French or larger or smaller in size lumen (see, FIG. 9A, 902B) of a PICC line may be configured to fit within clamping box 2000. In this manner, each of the first part 2002 and the second part 2004 may be formed as hollow halves in order to receive at least a portion of a blood vessel line therein. In some aspects, either one or both of first part 2002 and second part 2004 of clamping box 2000 comprise blood vessel line openings 2016 disposed on one side surface of clamping box 2000. For example, blood vessel line openings 2016 may comprise semi-circular openings that may allow the blood vessel line to enter clamping box 2000 when the clamping box is in the locked position.

Figure 21:
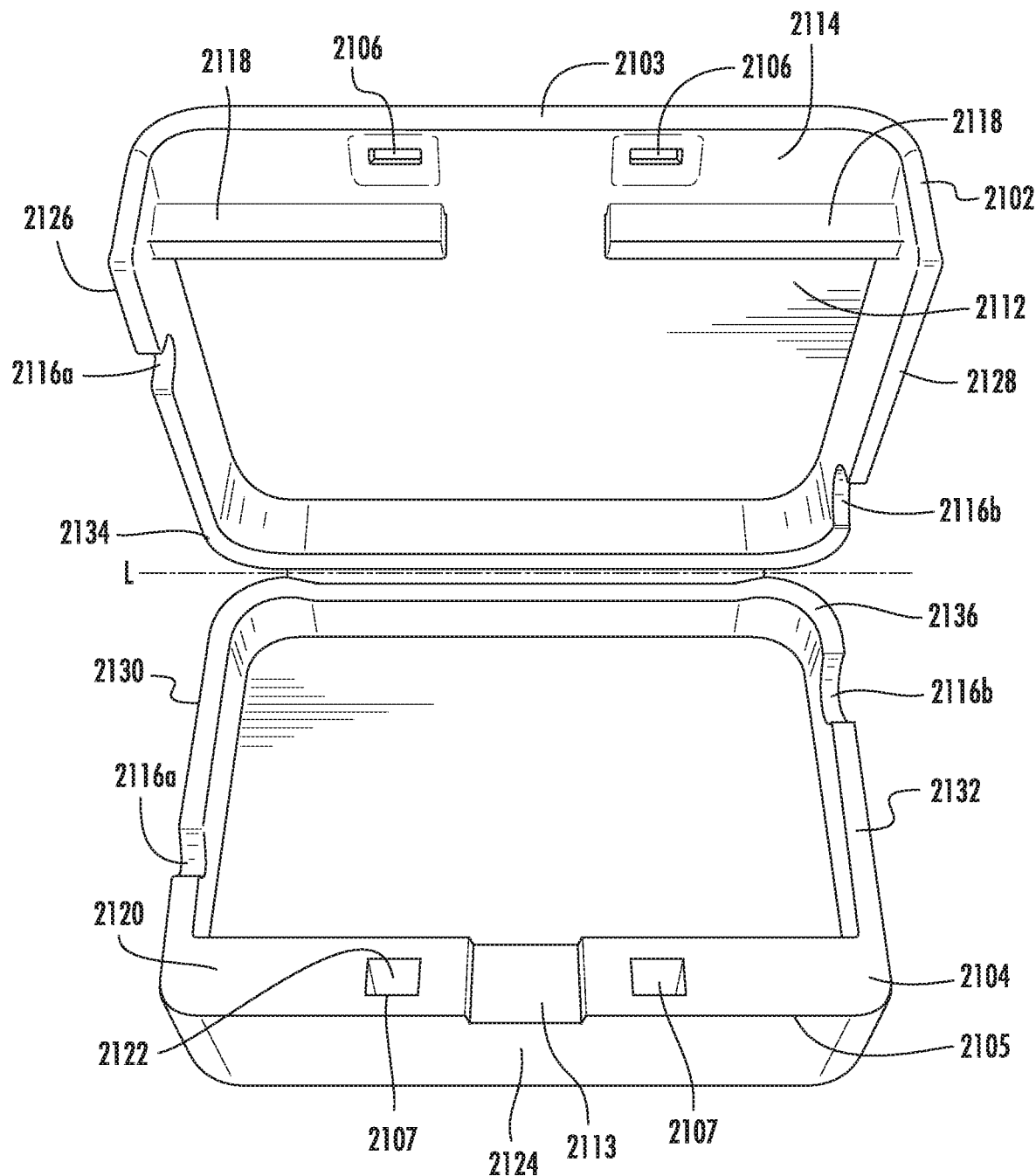
FIG. 21 a perspective view illustrating a tenth embodiment of an enclosure apparatus according to the presently disclosed subject matter in an open or unlocked position.

Referring now to FIG. 21 yet a further embodiment of a clamping box in accordance with the presently disclosed subject matter is referred to generally at 2100. Clamping box 2100 is configured to enclose at least a portion of an object, such as one or more blood vessel lines therein, although clamping box 2100 may be configured to enclose two or more blood vessel lines (e.g., two, three, four, etc.,). In some aspects, either one or both of first part 2102 and second part 2104 of clamping box 2100 comprise openings 2116a and 2116b disposed on opposing side surfaces of clamping box 2100. For example, openings 2116a and 2116b may comprise semi-circular openings that may allow a blood vessel line to enter and exit clamping box 2100 when the clamping box is in the closed or locked position. Openings 2116a and 2116b are positioned on sides 2126 and 2128, respectively, of first part 2012 and sides 2130 and 2132, respectively, of second part 2104 of clamping box 2100 in a manner such that openings 2116a and 2116b are not aligned with each other, e.g. not coaxial with each other or diagonally arranged with respect to each other.

Clamping box 2100 can comprise first part 2102 and second part 2104 that are adapted to be rotated about a pivot axis L towards or away from each other to move between locked or closed positions and unlocked or open positions. Pivot axis L is defined between a side 2134 of first part 2012 and a side 2136 of second part 2104 Notably, however, first part 2102 and second part 2104 may relate to one another in a manner other than pivoting. For example, a hinge, screw, spring, and/or any other mechanism may allow one or more part of clamping box 2100 to move relative to one another in order to enclose an object such as a blood vessel line within clamping box 2100. Regardless, first part 2102 and second part 2104 may be manipulated into a closed or locked position and an open or unlocked position. For example, first part 2102 and the second part 2104 may pivot along pivot axis L into a first or unlocked position where the first part 2102 and the second part 2104 are not in direct contact along second longitudinally extending side edges, where the second longitudinally extending side edges are disposed opposite the first longitudinally extending side edges. In another example, the first part 2102 and the second part 2104 may pivot along pivot axis L into a second or locked position where the first part 2102 and the second part 2104 are in direct contact along the second longitudinally extending side edges (such as shown with in the embodiment in FIG. 16D). In some aspects, clamping box 2100 may comprise more or less than first part 2102 and second part 2104, each of which may be manipulated into locked and/or unlocked positions. For example, clamping box 2100 may comprise one part, three parts, four parts, etc.

In some aspects, clamping box 2100 may have a substantially rounded rectangular prism shape such that each of first part 2102 and second part 2104 form a rounded rectangular prism when pivoted into the locked position. Alternately, in some aspects, clamping box 2100 may have any geometric shape with some basic functionality allowing clamping box 2100 to enclose an object such as a blood vessel line within box 2100. For example, clamping box 2100 may be square, ovular, triangular, cylindrical pointed, non-uniform, etc. In other aspects, each box may be manufactured according to the measurements of an extremity of a patient so that the box contours to that extremity. For example, clamping box 2100 may be sized and shaped to conform to a patient's arm.

In some aspects, first part 2102 and second part 2104 are configured to close or lock relative to one another. A locking mechanism disposed on or through either one or both of first part 2102 and second part 2104 may be provided in order to prevent a patient and/or other user from easily gaining entry to the blood vessel line enclosed by clamping box 2100 without detection. However, the locking mechanism may be weak enough to allow for a patient and/or other user to gain entry, if the patient and/or other user is determined to do so. But the locking mechanism is configured so that if tampering does occur, it is easily and quickly detectable by medical personnel. Thus, locking mechanisms as described in FIGS. 16A-16D and in FIGS. 17A-20C can be used with clamping box 2100.

By way of example and continuing with reference to FIG. 21, one or more hole 2106 is disposed, optionally centrally disposed, on a first longitudinally extending side edge 2103 of first part 2102. One or more hole 2106 passes through an outer surface 2111 of first part 2102 through to an inner surface 2114 of first part 2102. First part 2102 further comprises supports 2118 disposed on inner surface 2114 on a side of one or more hole 2106 opposite of longitudinal side edge 2103. Supports 2118 extend from ends of first part 2102 towards the center of first part 2102 but are separated by gap 2112. One or more hole 2107 is disposed, optionally centrally disposed, on a second longitudinally extending side edge 2105 of second part 2104. One or more hole 2107 passes through an outer surface 2120 of second part 2104 to an inner compartment 2122 and the outer surface 2120 of second part 2104 also a comprises a transparent window 2124. A recess 2113 is formed centrally on side edge 2105 of second part 2104, adjacent or between one or more hole 2107. When first part 2102 is moved toward second part 2104 first longitudinally extending side edge 2103 of first part 2102 is moved to rest on surface 2120 of second longitudinally extending side edge 2105 of second part 2104, one or more hole 2106 and 2107 are aligned. Recess 2113 is also aligned with gap 2112 between supports 2118. A pin, such as pin 1601 (see FIG. 16A), is then placed in clamping box 2100 such that one or protrusion 1608 deforms and passes through holes 2106 and 2107 and fits within inner compartment 2122, expanding to lock clamping box 2100. Compartment 2122 can be hidden (for example, not readily observable by user when box 2100 is in place, or can comprise a window 2124, which can be transparent. In this latter case, box 2100 can be locked and unlocked, and tampering detected, as described elsewhere herein with respect to FIGS. 16A-16D.

In alternative configurations, clamping boxes 600, 800, 1000, and 1400 as described herein above can be provided with a compartment like compartment 2122. For example, one or more protrusion 608, 808, 1008, and 1108 as described herein above, which are designed to break, can be caught in such a compartment.

In some aspects, clamping box 2100 may be 3D printed although other manufacturing techniques such as extruding, injection molding, etc., may be used. In some aspects, clamping box 2100 may be sized to fit at least a portion of a standard blood vessel line therein. For example, a 4 French or larger or smaller in size lumen (see, FIG. 9A, 902B) of a PICC line may be configured to fit within clamping box 2100. In this manner, each of the first part 2102 and the second part 2104 may be formed as hollow halves in order to receive at least a portion of a blood vessel line therein. In some aspects, the apparatus and/or system may include a sticker configured to be applied onto a surface of the first part and the second part of the clamping box and over at least a seam formed at the surfaces of the first part and the second part of the clamping box when the clamping box is in a closed or locked position. See e.g., sticker 950 in FIG. 9B. In some aspects, the surface may be a front surface of the clamping box. Advantageously, the sticker may provide secondary verification that the apparatus has been tampered with. For example, if the sticker has been broken (see sticker parts 950a and 950b in FIGS. 9C and 9D), medical personnel may be able to quickly detect that tampering of the blood vessel enclosure has occurred. In some aspects, the sticker may be color-coded to represent a time, date, personnel in charge of blood vessel line management, etc. In some aspects, the sticker may comprise a material that may be easily applied to the front surface of the clamping box. For example, the sticker may comprise a foil sticker with an adhesive that may adhere to the surface of the box, but is capable of tearing by a predetermined amount of force. As used herein, a predetermined amount of force may correspond to enough force that is necessary to tamper with the enclosure (i.e., force needed to be exerted by a user to open the enclosure without the unlocking mechanism).

Results from Prototype Study

A prototype substantially as set forth in FIGS. 6A-6C was used in conjunction with an unlocking mechanism as set forth in FIG. 7 for testing by a group of nurses in a hospital setting. The following observations were made.

The device could not be closed again without showing evidence of it being opened.

The device did not fall off or open while in use

>90% of nurses surveyed state the device would strongly enable detection of tampering.

>85% of nurses surveyed state the device is easy to use.

>80% of nurses stated the device would deter inappropriate access to lines.

>70% of nurses stated the device very minimally impacted work flow.

>80% of nurses stated it took less than 30 sec to apply the device.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A tamper detection apparatus comprising:
a clamping box configured for enclosing at least a portion of an object in a manner that provides detection of tampering, wherein the clamping box comprises a first part and a second part attachable to one another, wherein the clamping box is configured for enclosing at least a portion of one or more ingress/egress line in a manner that provides detection of tampering, wherein the clamping box comprises one or more ingress/egress line opening disposed on one or more side surfaces;
a locking mechanism for the clamping box configured to maintain the first part of the clamping box and the second part of the clamping box in a closed position, wherein the apparatus is configured for opening or removal from the object by breaking the clamping box and/or the locking mechanism; and
a compartment in the first part or the second part of the clamping box, wherein the compartment is configured to receive at least a portion of the locking mechanism when the locking mechanism is broken; and
wherein the first part of the clamping box and the second part of the clamping box each comprise a support disposed along a side edge, wherein the supports are configured for use in opening the apparatus;
wherein opening or removal of the clamping box is detectable.

2. The apparatus of claim 1, wherein the clamping box comprises one or more opening disposed on a side surface and wherein the clamping box is closed on an opposite side surface.

3. The apparatus of claim 1, wherein the clamping box comprises an opening disposed on a side surface and an opening on an opposite side surface, wherein the openings are not coaxial with respect to each other.

4. The apparatus of claim 1, wherein the locking mechanism comprises one or more protrusion disposed on the second part configured to engage a hole disposed on the first part.

5. The apparatus of claim 1, wherein the locking mechanism comprises one or more protrusion configured to be inserted in one or more hole disposed on the first part and/or one or more hole disposed on the second part.

6. The apparatus of claim 1, wherein the first part and the second part of the clamping box have a periphery that defines an interior of the first part and the second part and the compartment is outside the periphery.

7. The apparatus of claim 1, wherein the first part and the second part of the clamping box have a periphery that defines an interior of the first part and the second part and the compartment is inside the periphery.

8. The apparatus of claim 1, wherein the first part or the second part is configured to provide visual access to the compartment, whereby tampering with the apparatus can be detected upon observation of the at least a portion of the locking mechanism in the compartment.

9. The apparatus of claim 1, wherein the first part or the second part is configured such that tampering with the apparatus can be detected upon auditory observation of the at least a portion of the locking mechanism in the compartment.

10. The apparatus of claim 1, wherein the compartment is hidden from a user's view.

11. The apparatus of claim 1, comprising an unlocking mechanism configured to break the locking mechanism of the clamping box.

12. The apparatus of claim 1, further comprising a sticker configured to be applied onto a surface of the clamping box when the clamping box is in the closed position, wherein the sticker is configured to tear upon force.

13. A tampering detection system comprising:
an object, wherein the object is one or more ingress/egress line comprising a first end and a second end and the clamping box is configured for enclosing at least a portion of the one or more ingress/egress line; and
a tamper detection apparatus comprising:
  a clamping box configured for enclosing at least a portion of an object in a manner that provides detection of tampering, wherein the clamping box comprises a first part and a second part attachable to one another, wherein the clamping box is configured for enclosing at least a portion of one or more ingress/egress line in a manner that provides detection of tampering, wherein the clamping box comprises one or ingress/egress line opening disposed on one or more side surfaces;
  a locking mechanism for the clamping box configured to maintain the first part of the clamping box and the second part of the clamping box in a closed position, wherein the apparatus is configured for opening or more removal from the object by breaking the clamping box and/or the locking mechanism;
  a compartment in the first part or the second part of the clamping box, wherein the compartment is configured to receive at least a portion of the locking mechanism when the locking mechanism is broken; and
  wherein the first part of the clamping box and the second part of the clamping box each comprise a support disposed along a side edge, wherein the supports are configured for use in opening the apparatus; wherein opening or removal of the clamping box is detectable.

14. The system of claim 13, wherein the clamping box comprises an opening disposed on a side surface and wherein the clamping box is closed on an opposite side surface.

15. The system of claim 13, wherein the clamping box comprises an opening disposed on a side surface and an opening on an opposite side surface, wherein the openings are not coaxial with respect to each other.

16. The system of claim 13, wherein the locking mechanism comprises one or more protrusion disposed on the second part configured to engage a hole disposed on the first part.

17. The system of claim 13, wherein the locking mechanism comprises one or more protrusion configured to be inserted in one or more hole disposed on the first part and/or one or more hole disposed on the second part.

18. The system of claim 13, wherein the first part and the second part of the clamping box have a periphery that defines an interior of the first part and the second part and the compartment is outside the periphery.

19. The system of claim 13, wherein the first part and the second part of the clamping box have a periphery that defines an interior of the first part and the second part and the compartment is inside the periphery.

20. The system of claim 13, wherein the first part or the second part is configured to provide visual access to the compartment, whereby tampering with the apparatus can be detected upon observation of the at least a portion of the locking mechanism in the compartment.

21. The system of claim 13, wherein the first part or the second part is configured such that tampering with the apparatus can be detected upon auditory observation of the at least a portion of the locking mechanism in the compartment.

22. The system of claim 13, comprising an unlocking mechanism configured to break the locking mechanism of the clamping box.

23. The system of claim 13, further comprising a sticker configured to be applied onto a surface of the clamping box when the clamping box is in the closed position, wherein the sticker is configured to tear upon force.

24. The system of claim 13, wherein the compartment is hidden from a user's view.

25. The system of claim 13, wherein a lumen of the ingress/egress line is configured to be positioned within the clamping box.

26. A method for detecting tampering with an object, the method comprising:
(a) positioning an object, wherein the object is one or more ingress/egress line comprising a first end and a second end and the clamping box is configured for enclosing at least a portion of the one or more ingress/egress line, in a tamper detection apparatus comprising:
  a clamping box configured for enclosing at least a portion of an object in a manner that provides detection of tampering, wherein the clamping box comprises a first part and a second part attachable to one another;
  a locking mechanism for the clamping box configured to maintain the first part of the clamping box and the second part of the clamping box in a closed position, wherein the apparatus is configured for opening or removal from the object by breaking the clamping box and/or the locking mechanism;
  a compartment in the first part or the second part of the clamping box, wherein the compartment is configured to receive at least a portion of the locking mechanism when the locking mechanism is broken; and wherein the first part of the clamping box and the second part of the clamping box each comprise a support disposed along a side edge, wherein the supports are configured for use in opening the apparatus; and (b) detecting tampering with the object by observing the clamping box.

\* \* \* \* \*